(12) United States Patent
Jain et al.

(10) Patent No.: US 12,350,292 B2
(45) Date of Patent: Jul. 8, 2025

(54) BIOACTIVE RENAL CELLS FOR THE TREATMENT OF CHRONIC KIDNEY DISEASE

(71) Applicant: ProKidney, Grand Cayman (KY)

(72) Inventors: Deepak Jain, Winston-Salem, NC (US); Timothy A. Bertram, George Town (KY)

(73) Assignee: ProKidney, Grand Cayman (KY)

( * ) Notice: Subject to any disclaimer, the term of this patent is extended or adjusted under 35 U.S.C. 154(b) by 0 days.

(21) Appl. No.: 18/435,911

(22) Filed: Feb. 7, 2024

(65) Prior Publication Data

US 2024/0316108 A1   Sep. 26, 2024

Related U.S. Application Data

(62) Division of application No. 17/404,038, filed on Aug. 17, 2021, now Pat. No. 11,931,383, which is a division of application No. 15/663,430, filed on Jul. 28, 2017, now Pat. No. 11,123,372.

(60) Provisional application No. 62/532,338, filed on Jul. 13, 2017, provisional application No. 62/368,919, filed on Jul. 29, 2016.

(51) Int. Cl.
| | |
|---|---|
| *A61K 35/22* | (2015.01) |
| *A61B 17/34* | (2006.01) |
| *A61K 9/00* | (2006.01) |
| *A61K 47/42* | (2017.01) |

(52) U.S. Cl.
CPC .......... *A61K 35/22* (2013.01); *A61B 17/3421* (2013.01); *A61K 9/0019* (2013.01); *A61K 47/42* (2013.01)

(58) Field of Classification Search
None
See application file for complete search history.

(56) References Cited

U.S. PATENT DOCUMENTS

| | | |
|---|---|---|
| 4,377,513 A | 3/1983 | Sugimoto et al. |
| 4,769,037 A | 9/1988 | Midcalf |
| 4,996,154 A | 2/1991 | Gabriels, Jr. |
| 5,085,629 A | 2/1992 | Goldberg et al. |
| 5,092,886 A | 3/1992 | Dobos-Hardy |
| 5,429,938 A | 7/1995 | Humes |
| 5,516,680 A | 5/1996 | Naughton et al. |
| 5,545,131 A | 8/1996 | Davankov |
| 5,549,674 A | 8/1996 | Humes et al. |
| 5,854,006 A | 12/1998 | Hanigan et al. |
| 5,952,226 A | 9/1999 | Aebischer et al. |

(Continued)

FOREIGN PATENT DOCUMENTS

| | | |
|---|---|---|
| CN | 1044496 A | 8/1990 |
| CN | 102271692 A | 12/2011 |

(Continued)

OTHER PUBLICATIONS

Kelley et al., Cell Transplant. 22: 1023-1039 (2013).*

(Continued)

*Primary Examiner* — Erin M. Bowers
(74) *Attorney, Agent, or Firm* — Mintz Levin Cohn Ferris Glovsky and Popeo, P.C.

(57) ABSTRACT

The present invention concerns methods of using bioactive renal cell populations to provide regenerative effects to a native kidney for the treatment of chronic kidney disease.

7 Claims, 22 Drawing Sheets

(56) References Cited

U.S. PATENT DOCUMENTS

| | | | |
|---|---|---|---|
| 5,994,127 | A | 11/1999 | Selden et al. |
| 6,060,270 | A | 5/2000 | Humes |
| 6,140,039 | A | 10/2000 | Naughton et al. |
| 6,224,893 | B1 | 5/2001 | Langer et al. |
| 6,376,244 | B1 | 4/2002 | Atala |
| 6,410,320 | B1 | 6/2002 | Humes |
| 6,548,081 | B2 | 4/2003 | Sadozai et al. |
| 6,673,339 | B1 | 1/2004 | Atala et al. |
| 6,747,002 | B2 | 6/2004 | Cheung et al. |
| 6,777,205 | B1 | 8/2004 | Carcagno et al. |
| 6,784,154 | B2 | 8/2004 | Westenfelder |
| 6,827,938 | B2 | 12/2004 | Hart et al. |
| 7,326,570 | B2 | 2/2008 | Nigam et al. |
| 7,563,822 | B2 | 7/2009 | Koizumi et al. |
| 11,123,372 | B2 | 9/2021 | Jain et al. |
| 11,931,383 | B2 | 3/2024 | Jain et al. |
| 2003/0124099 | A1 | 7/2003 | Atala |
| 2004/0167634 | A1 | 8/2004 | Atala et al. |
| 2004/0185503 | A1 | 9/2004 | Yamanouchi et al. |
| 2006/0153894 | A1 | 7/2006 | Ghabrial et al. |
| 2007/0059293 | A1 | 3/2007 | Atala |
| 2007/0078084 | A1 | 4/2007 | Kishore et al. |
| 2007/0116679 | A1 | 5/2007 | Atala |
| 2007/0128174 | A1 | 6/2007 | Kleinsek et al. |
| 2007/0184033 | A1 | 8/2007 | Sevrain et al. |
| 2007/0276507 | A1 | 11/2007 | Bertram et al. |
| 2008/0305146 | A1 | 12/2008 | Atala et al. |
| 2009/0186004 | A1 | 7/2009 | Fukui et al. |
| 2010/0104544 | A1 | 4/2010 | Atala et al. |
| 2010/0112062 | A1 | 5/2010 | Atala et al. |
| 2011/0053157 | A1 | 3/2011 | Skog et al. |
| 2011/0117162 | A1 | 5/2011 | Presnell et al. |
| 2012/0135433 | A1 | 5/2012 | Sugaya et al. |
| 2013/0330364 | A1 | 12/2013 | Basu et al. |
| 2015/0246073 | A1 | 9/2015 | Basu et al. |
| 2018/0055885 | A1 | 3/2018 | Jain et al. |
| 2021/0283182 | A1 | 9/2021 | Jain et al. |
| 2022/0031755 | A1 | 2/2022 | Jain et al. |

FOREIGN PATENT DOCUMENTS

| | | | |
|---|---|---|---|
| JP | 2014502261 A | | 1/2014 |
| JP | 2016504017 A | | 2/2016 |
| KR | 1020010026239 A | | 4/2001 |
| KR | 1020150085818 A | | 7/2015 |
| WO | 9002796 A1 | | 3/1990 |
| WO | 9012604 A1 | | 11/1990 |
| WO | 9307913 A1 | | 4/1993 |
| WO | 9511048 A2 | | 4/1995 |
| WO | 9640175 A1 | | 12/1996 |
| WO | 9748404 A1 | | 12/1997 |
| WO | 02061053 A1 | | 8/2002 |
| WO | 03043674 A1 | | 5/2003 |
| WO | 2007035843 A2 | | 3/2007 |
| WO | 2008045498 A1 | | 4/2008 |
| WO | 2008061213 A2 | | 5/2008 |
| WO | 2008066498 A1 | | 6/2008 |
| WO | 2008153970 A1 | | 12/2008 |
| WO | 2010056328 A1 | | 5/2010 |
| WO | 2010057013 A1 | | 5/2010 |
| WO | 2010057015 A1 | | 5/2010 |
| WO | 2011143499 A1 | | 11/2011 |
| WO | 2012064369 A1 | | 5/2012 |
| WO | WO 2012/064369 | * | 5/2012 |
| WO | 2014066699 A1 | | 5/2014 |
| WO | WO 2014/066699 | * | 5/2014 |
| WO | 2018002218 A1 | | 1/2018 |
| WO | 2018022108 A1 | | 2/2018 |

OTHER PUBLICATIONS

Tsagalis, Hippokratia 15(Suppl 1): 39-43 (2011).*

International Search Report and Written Opinion received for PCT Patent International Application No. PCT/US2009/064418, mailed on Jan. 19, 2010, 3 pages.

International Search Report received for PCT Patent International Application No. PCT/US2000/033891, mailed on Mar. 26, 2001, 40 pages.

International Search Report received for PCT Patent International Application No. PCT/US2009/064421, mailed on Feb. 19, 2010, 3 pages.

Aboushwareb et al. (2008) "Erythropoietin Producing Cells for Potential Cell Therapy", World Journal of Urology, 26(4):295-300.

Almeida et al. (Sep. 30, 2013) "Safety of Immunosuppressive Drugs used as Maintenance Therapy in Kidney Transplantation: A Systematic Review and Meta-analysis", Pharmaceuticals (Basel), 6(10):1170-1194.

Amann et al. (Aug. 1998) "Cardiac Remodelling in Experimental Renal Failure—an Immunohistochemical Study", Nephrology Dialysis Transplantation, 13(8):1958-1966.

Anglani et al. (May 1, 2008) "The Renal Stem Cell System in Kidney Repair and Regeneration", Frontiers in Bioscience, 13:6395-6405.

Astor et al. (May 15, 2008) "Glomerular Filtration Rate, Albuminuria, and Risk of Cardiovascular and All-Cause Mortality in the US Population", American Journal of Epidemiology, 167(10):1226-1234.

Atala et al. (Apr. 15, 2006) "Tissue-Engineered Autologous Bladders for Patients Needing Cystoplasty", The Lancet, 367(9518):1241-1246.

Basu et al. (2014) "Cell-Based Therapeutic Products: Potency Assay Development and Application", Regenerative Medicine, 9(4):497-512.

Basu et al. (May 1, 2011) "Functional Evaluation of Primary Renal Cell/biomaterial Neo-Kidney Augment Prototypes for Renal Tissue Engineering", Cell Transplantation, 20(11-12):1771-1790.

Ben-Ze'ev et al. (Apr. 1998) "Cell-Cell and Cell-Matrix Interactions Differentially Regulate the Expression of Hepatic and Cytoskeletal Genes in Primary Cultures of Rat Hepatocytes", Proceedings of the National Academy of Sciences, 85(7):2161-2165.

Brenner, B. M. (1985) "Nephron Adaptation to Renal Injury or Ablation", American Journal of Physiology, 249(3):F324-F337.

Brown et al. (2008) "Characterisation of Human Tubular Cell Monolayers as a Model of Proximal Tubular Xenobiotic Handling", Toxicology and Applied Pharmacology, 233(3):428-438.

Bruce et al. (2013) "Ex Vivo Culture and Separation of Functional Renal Cells", Methods in Molecular Biology, 1001:53-64.

Zhou et al. (Sep. 2008) "Urinary Exosomal Transcription Factors, a New Class of Biomarkers for Renal Disease", Kidney International, 74(5):613-621.

Bruce et al. (Apr. 1, 2011) "Hypoxic Exposure of Cultured Human Renal Cells Induces Mediators of Cell Migration and Attachment and Facilitates the Repair of Tubular Cell Monolayers In Vitro", Experimental Biology Meeting, Washington, DC, 25 (S1):121.6-121.6.

Bruce et al. (Nov. 16, 2015) "Selected Renal Cells Modulate Disease Progression in Rodent Models of Chronic Kidney Disease via NF-κb and TGF-β1 pathways", Regenerative Medicine, 10(7):815-839.

Canes et al. (2009) "Functional Outcomes Following Percutaneous Surgery in the Solitary Kidney", The Journal of Urology, 181(1):154-160.

Castrop, H. (2007) "Mediators of Tubuloglomerular Feedback Regulation of Glomerular Filtration: ATP and Adenosine", Acta Physiologica, 189(1):3-14.

Chade et al. (Feb. 2009) "Endothelial Progenitor Cells Restore Renal Function in Chronic Experimental Renovascular Disease", Circulation, 119(4):547-557.

Collins et al. (2003) "A Vision for the Future of Genomics Research", Nature, 422(6934): 835-847.

Daley et al. (Jan. 2003) "Realistic Prospects for Stem Cell Therapeutics", American Society of Hematology, 2003 (1):398-418.

Dhingra et al. (Oct. 2001) "Type of Vascular Access and Mortality in US Hemodialysis Patients", Kidney International, 60(4):1443-1451.

(56) References Cited

OTHER PUBLICATIONS

Ding et al. (2008) "The Bioartificial Kidney and Bioengineered Membranes in Acute Kidney Injury", Nephron Experimental Nephrology, 109(4):e118-e112.
Dobronravov et al. (2015) "Clinical Factors Associated with the Occurence of Early Stages of Chronic Kidney Disease in Patients with Diabetes Mellitus Type 1", Research Institute of Nephrology, 19(6):9-13.
Donnelly et al. (2003) "New Insights into Renal Anemia", Canadian Journal of Diabetes, 27(2):176-181.
Eliopoulos et al. (2006) "Erythropoietin Delivery by Genetically Engineered Bone Marrow Stromal Cells for Correction of Anemia in Mice with Chronic Renal Failure", Journal of the American Society of Nephrology, 17:1576-1584.
Fisher, James W. (Jan. 1, 2003) "Erythropoietin: Physiology and Pharmacology Update", Experimental Biology and Medicine, 228(1):1-14.
Fontaine et al. (Feb. 1993) "Transplantation of Genetically Altered Hepatocytes Using Cell-Polymer Constructs", Transplantation Proceedings, 25(1):1002-1004.
Yokoo et al. (2006) "Xenobiotic Kidney Organogenesis from Human Mesenchymal Stem Cells Using a Growing Rodent Embryo", Journal of the American Society of Nephrology, 17:1026-1034.
Genestie et al. (Jul. 1995) "Polarity and Transport Properties of Rabbit Kidney Proximal Tubule Cells on Collagen IV-coated Porous Membranes", American Journal of Physiology—Renal Physiology, 269(1):F22-F30.
Genheimer et al. (May 2012) "Molecular Characterization of the Regenerative Response Induced by Intrarenal Transplantation of Selected Renal Cells in a Rodent Model of Chronic Kidney Disease", Cells Tissues Organs, 196(4):374-384.
Gerstein et al. (Jul. 25, 2001) "Albuminuria and Risk of Cardiovascular Events, Death, and Heart Failure in Diabetic and Nondiabetic Individuals", JAMA, 286(4):421-426.
Go et al. (Sep. 23, 2004) "Chronic Kidney Disease and the Risks of Death, Cardiovascular Events, and Hospitalization", The New England Journal of Medicine, 351:1296-1305.
Guo et al. (Mar. 2010) "Cellular Maintenance and Repair of the Kidney", Annual Review of Physiology, 72:357-376.
Hammerman, Marc R. (2001) "Growing Kidneys", Current Opinion in Nephrology and Hypertension, 10(1):13-17.
Held et al. (Jan. 2006) "In Vivo Genetic Selection of Renal Proximal Tubules", Molecular Therapy, 13(1):49-58.
Hemmelgarn et al. (Jun. 2006) "Progression of Kidney Dysfunction in the Community-Dwelling Elderly", Kidney International, 69(12):2155-2161.
Hopkins et al. (Oct. 20, 2008) "Stem Cell Options for Kidney Disease", Journal of Pathology, 217:265-281.
Humes et al. (Oct. 2004) "Initial Clinical Results of the Bioartificial Kidney Containing Human Cells in ICU Patients with Acute Renal Failure", Kidney International, 66(4):1578-1588.
Humes et al. (1999) "Replacement of Renal Function in Uremic Animals with a Tissue-Engineered Kidney", Nature Biotechnology, 17(5):451-455.
Humphreys et al. (Mar. 6, 2008) "Intrinsic Epithelial Cells Repair the Kidney after Injury", Cell Stem Cell, 2(3):284-291.
Humphreys et al. (2008) "Mesenchymal Stem Cells in Acute Kidney Injury", Annual Review of Medicine, 59:311-325.
Tsagalis, G. (2011) "Renal Anemia: A Nephrologist's View", Hippokratia, 15(Suppl 1):39-43.
Sugimoto et al. (2006) "Bone-Marrow-Derived Stem Cells Repair Basement Membrane Collagen Defects and Reverse Genetic Kidney Disease", Proceedings of the National Academy of Sciences, 103(19):7321-7326.
Ilagan et al. "Secreted Factors from Bioactive Kidney Cells Attenuate NFκB Signaling Pathways: Implications for a Jaracrine Mechanism of Immune Regulation and Regenerative Outcomes", engion, Inc., Science & Technology, Ninston-Salem, North Carolina, USA.

Inker et al. (Jul. 5, 2012) "Estimating Glomerular Filtration Rate from Serum Creatinine and Cystatin C", The New England Journal of Medicine, 367(1):20-29.
Jarad et al. (2009) "Update on the Glomerular Filtration Barrier", Current Opinion in Nephrology and Hypertension, 18:226-232.
Jayo et al. (Jul. 2008) "Early Cellular and Stromal Responses in Regeneration Versus Repair of a Mammalian Bladder Using Autologous Cell and Biodegradable Scaffold Technologies", The Journal of Urology, 180(1):392-397.
Jayo et al. (Aug. 27, 2008) "Long-term Durability, Tissue Regeneration and Neo-Organ Growth during Skeletal Maturation with a Neo-Bladder Augmentation Construct", Regenerative Medicine, 3(5):671-682.
Jayo et al. (Jan. 2008) "Tissue Engineering and Regenerative Medicine: Role of Toxicologic Pathologists for an Emerging Medical Technology", Toxicologic Pathology, 36(1):92-96.
Jha et al. (Jul. 20, 2013) "Chronic Kidney Disease: Global Dimension and Perspectives", Lancet, 382(9888):260-272.
Joraku et al. (Feb. 2009) "In Vitro Generation of Three-dimensional Renal Structures", Methods, 47(2):129-133.
Kaufman et al. (1974) "Compensatory Adaptation of Structure and Function Following Progressive Renal Ablation", Kidney International, 6:10-17.
Keith et al. (Mar. 22, 2004) "Longitudinal Follow-up and Outcomes among a Population with Chronic Kidney Disease in a Large Managed Care Organization", Arch Internal Medicine, 164(6):659-663.
Kelley et al. (2013) "A Population of Selected Renal Cells Augments Renal Function and Extends Survival in the ZSFI Model of Progressive Diabetic Nephropathy", Cell Transplantation, 22(6):1023-1039.
Yamaleyeva et al. (2010) "Primary Human Kidney Cell Cultures Containing Erythropoietin-producing Cells Improve Renal Injury", TERMIS Conference, Orlando.
Kelley et al. (2010) "Bioactive Renal Cells Augment Renal Function in the ZSF1 Model of Diabetic Nephropathy", TERMIS Conference, Orlando, 1 page.
Stevens et al. (Jun. 8, 2006) "Assessing Kidney Function—Measured and Estimated Glomerular Filtration Rate", The New England Journal of Medicine, 354(23): 2473-2483.
Kelley et al. (2011) "Intra-Renal Transplantation of Bioactive Renal Cells Preserves Renal Functions and Extends Survival in the ZSF1 Model of Progressive Diabetic Nephropathy", American Diabetes Association (ADA) Conference.
Kelley et al. (2010) "Tubular Cell-Enriched Subpopulation of Primary Renal Cells Improves Survival and Augments Kidney Function in Rodent Model of Chronic Kidney Disease", American Journal of Physiology—Renal Physiology, 299(5):F1026-F1039.
Khan et al. (Jul. 2002) "Health Care Utilization Among Patients with Chronic Kidney Disease", Kidney International, 62(1): 229-236.
Kim et al. (Jun. 2007) "Kidney Tissue Reconstruction by Fetal Kidney Cell Transplantation: Effect of Gestation Stage of Fetal Kidney Cells", Stem Cells, 25(6):1393-1401.
Kovesdy et al. (Apr. 2006) "Association of Kidney Function with Mortality in Patients with Chronic Kidney Disease not yet on Dialysis: A Historical Prospective Cohort Study", Advances in Chronic Kidney Disease, 13(2):183-188.
Kreisberg et al. (1977) "Separation of Proximal Tubule Cells from Suspensions of Rat Kidney Cells in Density Gradients of Ficoll in Tissue Culture Medium", American Journal of Pathology, 86(3):591-602.
Kucic et al. (2008) "Mesenchymal Stromal Cells Genetically Engineered to Overexpress IGF-I Enhance Cell-Based Gene Therapy of Renal Failure-Induced Anemia", American Journal of Renal Physiology, 295:F488-F496.
Kurtz et al. (Jul. 1, 1983) "Renal Mesangial Cell Cultures as a Model for Study of Erythropoietin Production", Proceedings of the National Academy of Sciences, 80(13):4008-4011.
Levey et al. (Jun. 2005) "Definition and Classification of Chronic Kidney Disease: A Position Statement from Kidney Disease Improving Global Outcomes (KDIGO)", Kidney International, 67(6):2089-2100.

(56) References Cited

OTHER PUBLICATIONS

Levey et al. (Jul. 15, 2003) "National Kidney Foundation Practice Guidelines for Chronic Kidney Disease: Evaluation, Classification, and Stratification", Annals of Internal Medicine, 139(2):137-147.
Lin et al. (2005) "Intrarenal Cells, Not Bone Marrow-Derived Cells, are the Major Source for Regeneration in Postischemic Kidney", Journal of Clinical Investigation, 115(7):1756-1764.
Ludlow et al. (2012) "The Future of Regenerative Medicine: Urinary System", Tissue Engineering, 18(3):218-224.
Marshall et al. (Jan. 2007) "Increasing Renal Mass Improves Survival in Anephric Rats Following Metanephros Transplantation", Experimental Physiology, 92(1):263-271.
Yokoo et al. (Jun. 15, 2008) "Generation of a Transplantable Erythropoietin-Producer Derived from Human Mesenchymal Stem Cells", Transplantation, 85(11):1654-1658.
Nangaku (2006) "Chronic Hypoxia and Tubulointerstitial Injury: A Final Common Pathway to End-Stage Renal Failure", Journal of the American Society of Nephrology, 17:17-25.
National Kidney Foundation (Feb. 2002) "K/DOQI Clinical Practice Guidelines for Chronic Kidney Disease: Evaluation, Classification, and Stratification", American Journal of Kidney Diseases, 39:S1-266.
Newsome, P. (2008) "Yet Another Role for Mesenchmyal Stem Cells?", Transplantation, 85(11):1548-1549.
Ormrod et al. (1980) "Experimental Uremia: Description of a Model Producing Varying Degrees of Stable Uremia", Nephron, 26(5):249-254.
Patschan et al. (Apr. 2006) "Therapeutic Use of Stem and Endothelial Progenitor Cells in Acute Renal Injury: çaira", Current Opinion in Pharmacology, 6(2):176-183.
Platt et al. (Aug. 1952) "Experimental Renal Failure", Clinical Science, 11(3):217-231.
Plotkin et al. (2006) "Mesenchymal Cells from Adult Kidney Support Angiogenesis and Differentiate into Multiple Interstitial Cell Types Including Erythropoietin-producing Fibroblasts", American Journal of Physiology, 291:F902-F912.
Postma et al. (Oct. 2009) "The Economic Benefits of Preventing End-Stage Renal Disease in Patients with Type 2 Diabetes Mellitus", Nephrology Dialysis Transplantation, 24(10): 2975-2983.
Powe et al. (Mar. 2009) "Public Health Surveillance of CKD: Principles, Steps, and Challenges", American Journal of Kidney Diseases, 53(Suppl 3):S37-S45.
Stenvinkel et al. (Jul. 16, 2016) "Implantation of Autologous Selected Renal Cells in Diabetic Chronic Kidney Disease Stages 3 and 4-Clinical Experience of a "First in Human" Study", Kidney International Reports, 1(3):105-113.
Presnell et al. (Mar. 2011) "Isolation, Characterization, and Expansion Methods for Defined Primary Renal Cell Populations from Rodent, Canine, and Human Normal and Diseased Kidneys", Tissue Engineering Part C Methods, 17(3):261-273.
Prodromidi et al. (2006) "Bone Marrow-Derived Cells Contribute to Podocyte Regeneration and Amelioration of Renal Disease in a Mouse Model of Alport Syndrome", Stem Cells, 24:2448-2455.
Quiroga et al. (2015) "Present and Future in the Treatment of Diabetic Kidney Disease", Journal of Diabetes Research, 2015(801348):13 pages.
Rangel et al. (Aug. 2013) "C-Kit(+) Cells Isolated From Developing Kidneys are a Novel Population of Stem Cells With Regenerative Potential", Stem Cell, 31(8):1644-1656.
Rinsch et al. (2002) "Delivery of Erythropoietin by Encapsulated Myoblasts in a Genetic Model of Severe Anemia", Kidney International, 62:1395-1401.
Rossert et al. (2003) "Anemia Management and the Delay of Chronic Renal Failure Progression", Journal of the American Society of Nephrology, 14:S173-S177.
Rudikoff et al. (1982) "Single Amino Acid Substitition Altering Antigen-Binding Specificity", Proceedings of the National Academy of Sciences, 79(6):1979-1983.
Satchell et al. (2006) "Conditionally Immortalized Human Glomerular Endothelial Cells Expressing Fenestrations in Response to VEGF", Kidney International, 69:1633-1640.
Shaw et al. (Jan. 2010) "Global Estimates of the Prevalence of Diabetes for 2010 and 2030", Diabetes Research and Clinical Practice, 87(1):4-14.
Stenvinkel, Peter (Nov. 2010) "Chronic Kidney Disease: a Public Health Priority and Harbinger of Premature Cardiovascular Disease", Journal of Internal Medicine, 268(5):456-467.

\* cited by examiner

EFFECT #2
REDUCED RATE OF eGFR DECLINE
GLOMERULAR FILTRATION RATE (ML/MIN/1.73M3)

*Patients treated with ACT had slower rates of kidney function decline. Just a single low dose allowed their kidneys to filter blood better.*

Before ACT
-6.1

After ACT
-3.0

BIOACTIVE RENAL CELLS FOR THE TREATMENT OF CHRONIC KIDNEY DISEASE

CROSS-REFERENCE TO RELATED APPLICATIONS

This application is a divisional of U.S. patent application Ser. No. 17/404,038, filed Aug. 17, 2021, which is a divisional of U.S. patent application Ser. No. 15/663,430, filed Jul. 28, 2017 and issued as U.S. Pat. No. 11,123,372 on Sep. 21, 2021, which claims the benefit of priority to U.S. Provisional Patent Application No. 62/532,338, filed Jul. 13, 2017 and U.S. Provisional Patent Application No. 62/368,919, filed Jul. 29, 2016, the disclosures of which are incorporated by reference herein in their entirety, including any drawings.

FIELD OF THE INVENTION

The present invention relates to methods of treating a subject with chronic kidney disease using bioactive renal cell populations, and methods of providing regenerative effects to a native kidney using selected renal cell populations.

BACKGROUND OF THE INVENTION

Chronic kidney disease (CKD) is characterized by progressive nephropathy that, without therapeutic intervention, will worsen; ultimately the patient may reach end stage renal disease (ESRD). Prevalence data from the U.S. to Europe show that approximately 10% of the general population have stage 1-3 CKD (ERA, 2009; USRDS, 2011; Jha et al. Chronic kidney disease: global dimension and perspectives. Lancet. 2013; 382:260-72). Worldwide, the incidence and prevalence of CKD and ESRD are increasing while therapeutic outcomes remain poor (Shaw et al. Global estimates of the prevalence of diabetes for 2010 and 2030. Diabetes Res Clin Pract. 2010; 87:4-14). The greatest cause of ESRD is diabetes mellitus (Postma and de Zeeuw, 2009), and the incidence of CKD continues to increase, primarily due to the increases in the incidence of type 2 diabetes (Postma and de Zeeuw, 2009). CKD is often accompanied by adverse outcomes owing to underlying comorbidities and/or risk factors including hypertension and renovascular disease (Khan et al., 2002; Stenvinkel P. Chronic kidney disease—a public health priority and harbinger of premature cardiovascular disease J Intern med. 2010; 268:456-67). Due to serious comorbidities, patients with CKD are 5-11 times more likely to suffer premature death than survive to progress to ESRD (Collins et al., 2003; Smith et al., 2004). In order to survive, ESRD patients require renal replacement therapy (dialysis or transplantation). Preventing or delaying adverse outcomes of CKD by intervening early-on in the disease is the primary strategy in CKD management. Unfortunately, early therapeutic approaches to prevent disease progression have not been successful.

As CKD is characterized by low kidney cell proliferation and loss of regenerative processes (Messier and Leblond. Cell proliferation and migration as revealed by radiography after injection of thymidine-H3 into male rats and mice. Am J Anat. 1960; 106:247-85) maladaptive responses and fibrosis lead to progression of CKD. While standard of care therapies, such as strict glycemic control and blockade of the renin-angiotensin-aldosterone axis slow progression of diabetic nephropathy, they do not arrest or reverse it. A number of novel treatment strategies, such as antiproteinuric treatments, inhibitor of sodium-glucose co-transporter 2, antifibrotic agents, endothelin receptor antagonists, or transcription factors may slow or arrest progression of diabetic kidney disease (Quiroga et al. Present and future in the treatment of diabetic kidney disease. J Diabetes Res. 2015; 2015:801348). In addition, renal cell-based therapy have attracted recent interest as regeneration of tissues and organs is now within the technological reach of modern medicine (Ludlow et al. The Future of Regenerative Medicine: Urinary System. Tissue Engineering. 2012; 18:218-24).

New treatment paradigms involving tissue engineering and cellular-based applications have been described that provide substantial and durable augmentation of kidney functions, slow progression of disease and improve quality of life in this patient population. These next-generation regenerative medicine technologies provide isolated renal cells as a therapeutic option for chronic kidney disease (CKD). Presnell et al. WO/2010/056328 and Ilagan et al. PCT/US2011/036347 describe isolated bioactive renal cells, and methods of isolating and culturing the same, as well as methods of treatment with the cell populations. Injection of these bioactive renal cells into recipient kidneys has resulted in significant improvement in animal survival and kidney function, as evidenced for example by urine concentration and filtration functions, in nonclinical studies.

SUMMARY OF THE INVENTION

The invention relates generally to methods of treating CKD patients with a therapeutic composition composed of bioactive renal cells formulated in a biomaterial that provides stabilization and/or improvement and/or regeneration of kidney function.

In one aspect, the invention concerns a method for the treatment of CKD, wherein the method comprises injecting into the renal cortex of at least one kidney of a patient having chronic kidney disease a therapeutically effective amount of a composition comprising a bioactive renal cell population (BRC). In one or more embodiments, the injection is performed using a minimally invasive procedure such as percutaneous, laparoscopic or intravascular procedures. In another embodiment, a guiding cannula inserted percutaneously is used to puncture the kidney capsule prior to injection of the composition into the kidney of the patient.

The composition may be administered as a single injection or multiple injections over a specified time period. In one embodiment, the composition is administered with a minimum of one injection in one kidney. In another embodiment, the composition is administered as two or more injections. The first and second injections may be administered at any time up to 3 months apart, any time up to 6 months apart or at annual intervals. In one embodiment, the second injections is administered any time up to 3 years after the 1$^{st}$ injection. The composition may also be administered as one, two or more injections in one or both kidneys. In one embodiment, the composition is administered to subjects who contemporaneously receive standard-of-care treatment for CKD prior to receiving injections of NKA. In another embodiment, the two or more injections do not result in adverse immunogenic effects. In one embodiment, the composition is injected into one kidney of the patient. In another embodiment, the composition is injected into both kidneys of the patient. In yet another embodiment, single or multiple entry points may be used to inject the composition into the kidney of the patient. In yet another embodiment, the injection is into the renal parenchyma. In one embodiment, the patient receives a therapeutic dose at any given injection site. In a further embodiment, the patient receives a dose of $1$-$9 \times 10^6$ SRC/g KWest at any given injection site.

In some embodiments, the patient with CKD is further diagnosed as having type 2 diabetes mellitus. The underlying cause of the CKD may be diabetic nephropathy in these patients. In one embodiment, the patient's CKD is defined by an estimated glomerular filtration rate (eGFR) in the range of 15 to 60 mL/min. In another embodiment, the patient with CKD exhibits microalbuminuria may be defined by a urinary albumin-creatinine ratio (UACR) ≥30 mg/g or urine albumin excretion ≥30 mg/day on 24 hour urine collection.

In all embodiments, the patient's kidney function is improved as a result of the treatment. In one embodiment, the improved kidney function is demonstrated by a reduction in the rate of decline or increase in estimated glomerular filtration rate (eGFR). In another embodiment, the improved kidney function is demonstrated by reduction in total serum creatinine or the rate of increase in serum creatine (sCr). In one other embodiment, the improved kidney function is demonstrated by improved renal cortical thickness. The improved kidney function may be demonstrated by structural and functional alterations. In some additional embodiments, the improved kidney function is demonstrated by improvement in one or more of the factors in Table 5. In yet another embodiment, the improved kidney size and/or structure is determined by renal imaging. The method of renal imaging may be selected from among the technologies including ultrasound, MRI, and renal scintigraphy. In certain embodiments, the improved renal function is superior to the prior state of kidney structure or function.

In one aspect, the bioactive renal cell population is obtained from isolation and expansion of renal cells from kidney tissue under culturing conditions that enrich for cells capable of kidney regeneration. In another embodiment, the bioactive renal cell population is a selected renal cell (SRC) population obtained after density gradient separation of the expanded renal cells. In a particular embodiment, the SRC exhibit a buoyant density greater than approximately 1.0419 g/mL. In one embodiment, the BRC or SRC contains a greater percentage of one or more cell populations and lacks or is deficient in one or more other cell populations, as compared to a starting kidney cell population.

In one embodiment, the BRC or SRC are derived from a native autologous or allogeneic kidney sample. In another embodiment, the BRC or SRC are derived from a non-autologous kidney sample. In one or more of these embodiments, the sample may be obtained by kidney biopsy.

In another aspect of the invention, the BRC or SRC are formulated in a biomaterial. In one embodiment, the biomaterial comprises a gelatin-based hydrogel.

DETAILED DESCRIPTION OF THE INVENTION

Figure 1:
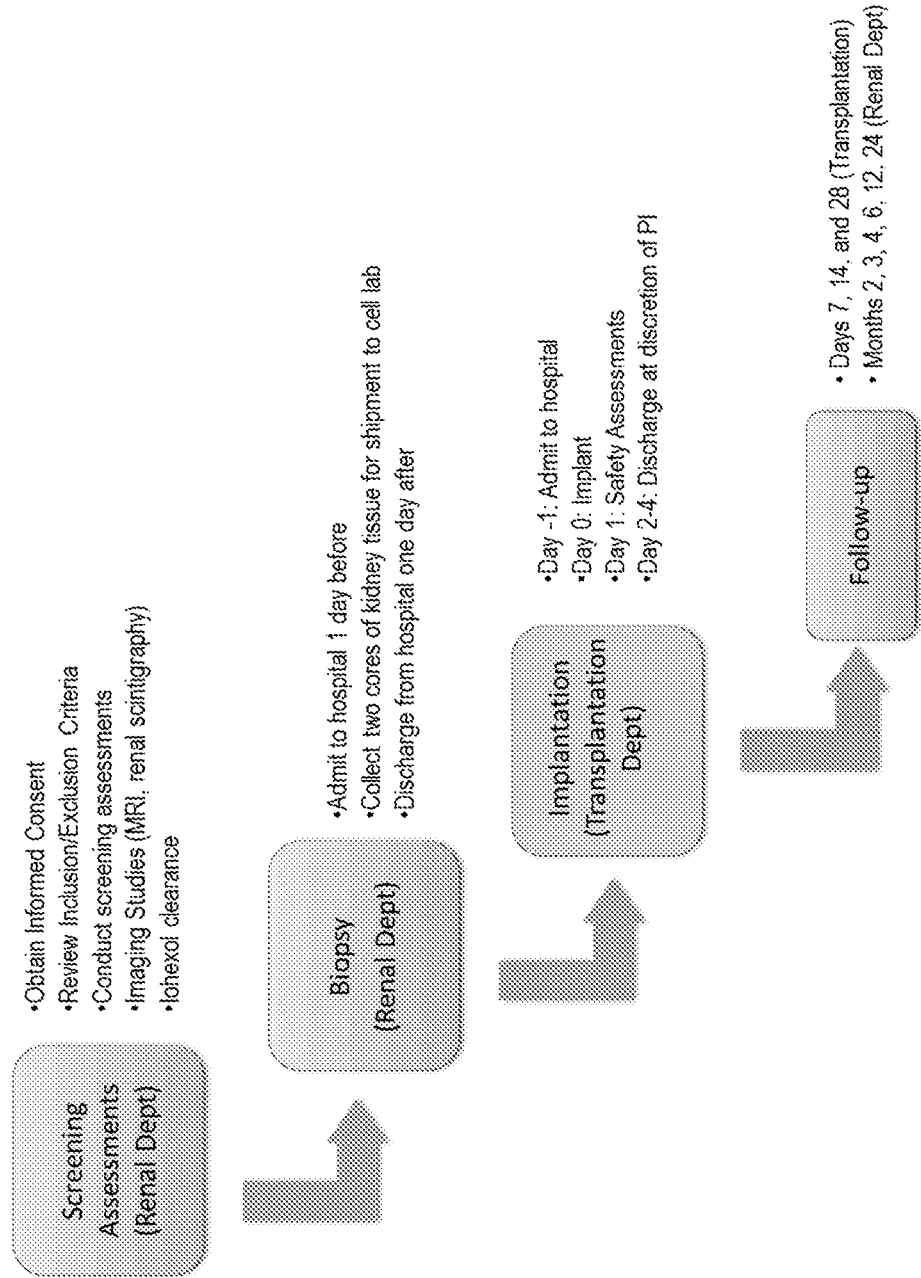
FIG. 1 depicts a simplified flow schedule of the clinical protocol used in the PHASE I study.

Reference will now be made in detail to certain embodiments of the invention. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described.

All references cited throughout the disclosure are expressly incorporated by reference herein in their entirety. In the event that one or more of the incorporated literature, patents, and similar materials differs from or contradicts this application, including but not limited to defined terms, term usage, described techniques, or the like, this application controls.

Definitions

Unless defined otherwise, technical and scientific terms used herein have the same meaning as commonly understood by one of ordinary skill in the art to which this invention belongs. Principles of Tissue Engineering, 3rd Ed. (Edited by R Lanza, R Langer, & J Vacanti), 2007 provides one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described.

The words "comprise," "comprising," "include," "including," and "includes" when used in this specification and claims are intended to specify the presence of stated features, integers, components, or steps, but they do not preclude the presence or addition of one or more other features, integers, components, steps, or groups thereof.

The term "cell population" as used herein refers to a number of cells obtained by isolation directly from a suitable tissue source, usually from a mammal. For example, a cell population may comprise populations of kidney cells, and admixtures thereof. The isolated cell population may be subsequently cultured in vitro. Those of ordinary skill in the art will appreciate that various methods for isolating and culturing cell populations for use with the present invention and various numbers of cells in a cell population that are suitable for use in the present invention. A cell population may be an unfractionated, heterogeneous cell population or an enriched homogeneous cell population derived from an organ or tissue, e.g., the kidney. For example, a heterogeneous cell population may be isolated from a tissue biopsy or from whole organ tissue. Alternatively, the heterogeneous cell population may be derived from in vitro cultures of mammalian cells, established from tissue biopsies or whole organ tissue. An unfractionated heterogeneous cell population may also be referred to as a non-enriched cell population. In one embodiment, the cell populations contain bioactive cells. Homogenous cell populations comprise a greater proportion of cells of the same cell type, sharing a common phenotype, or having similar physical properties, as compared to an unfractionated, heterogeneous cell population. For example, a homogeneous cell population may be isolated, extracted, or enriched from heterogeneous kidney cell population. In one embodiment, a homogeneous cell population is obtained as a cell fraction using density gradient separation of a heterogeneous cell suspension.

As used herein, the term "bioactive" means "possessing biological activity," such as a pharmacological or a therapeutic activity. In one embodiment, the bioactivity is enhancement of renal function and/or effect on renal homeostasis. In certain embodiments, the biological activity is, without limitation, analgesic; antiviral; anti-inflammatory; antineoplastic; immune stimulating; immune modulating; enhancement of cell viability, antioxidation, oxygen carrier, cell recruitment, cell attachment, immunosuppressant, angiogenesis, wound healing activity, or any combination thereof.

The term "bioactive renal cells" or "BRC" as used herein refers to renal cells having one or more of the following properties: capability to enhance renal functions, capability to affect (improve) renal homeostasis, and capability to promote healing, repair and/or regeneration of renal tissue or kidney. These cells may include functional tubular cells (based on improvements in creatinine excretion and protein retention), glomerular cells (based on improvement in protein retention), vascular cells and other cells of the corticomedullary junction. Bioactive renal cells (BRC) are obtained from isolation and expansion of renal cells from kidney tissue using methods that select for bioactive cells. In one embodiment, the bioactive renal cells have a regenerative effect on the kidney.

The term "selected renal cells" or "SRC" as used herein refers to cells obtained from isolation and expansion of bioactive renal cells (as hereinabove defined) from a suitable renal tissue source, wherein the SRC contains a greater percentage of one or more cell populations and lacks or is deficient in one or more other cell populations, as compared to a starting kidney cell population. SRCs are isolated populations of kidney cells, or admixtures thereof, enriched for specific bioactive components or cell types and/or depleted of specific inactive or undesired components or cell types for use in the treatment of kidney disease, i.e., providing stabilization and/or improvement and/or regeneration of kidney function. SRCs provide superior therapeutic and regenerative outcomes as compared with the starting population. In one embodiment, SRCs are obtained from the patient's renal cortical tissue via a kidney biopsy and selected by density gradient separation of the expanded renal cells. SRCs are composed primarily of renal tubular cells. Other parenchymal (vascular) and stromal (collecting duct) cells may be sparsely present in the isolated preparation. In one embodiment, the selected renal cells (SRCs) have a regenerative effect on the kidney.

The term "native organ" shall mean the organ of a living subject. The subject may be healthy or unhealthy. An unhealthy subject may have a disease associated with that particular organ.

The term "native kidney" shall mean the kidney of a living subject. The subject may be healthy or unhealthy. An unhealthy subject may have a kidney disease.

The term "regenerative effect" shall mean an effect which provides a benefit to a native organ, such as the kidney. The effect may include, without limitation, a reduction in the degree of injury to a native organ or an improvement in, restoration of, or stabilization of a native organ function or structure. Renal injury may be in the form of fibrosis, inflammation, glomerular hypertrophy, atrophy, etc. and related to a disease associated with the native organ in the subject.

The term "admixture" as used herein in the context of a cell population refers to a combination of two or more isolated, enriched cell population phenotypes derived from an unfractionated, heterogeneous cell population. According to certain embodiments, the cell populations of the present invention are renal cell populations.

An "enriched" cell population or preparation refers to a cell population derived from a starting organ cell population (e.g., an unfractionated, heterogeneous cell population) that contains a greater percentage of a specific cell type than the percentage of that cell type in the starting population. For example, a starting kidney cell population can be enriched for a first, a second, a third, a fourth, a fifth, and so on, cell population of interest. As used herein, the terms "cell population", "cell preparation" and "cell phenotype" are used interchangeably.

The term "hypoxic" culture conditions as used herein refers to culture conditions in which cells are subjected to a reduction in available oxygen levels in the culture system relative to standard culture conditions in which cells are cultured at atmospheric oxygen levels (about 21%). Non-hypoxic conditions are referred to herein as normal or normoxic culture conditions.

The term "oxygen-tunable" as used herein refers to the ability of cells to modulate gene expression (up or down) based on the amount of oxygen available to the cells. "Hypoxia-inducible" refers to the upregulation of gene expression in response to a reduction in oxygen tension (regardless of the pre-induction or starting oxygen tension).

The term "biomaterial" as used herein refers to a natural or synthetic biocompatible material that is suitable for introduction into living tissue supporting the selected bioactive cells in a viable state. A natural biomaterial is a material that is made by or originates from a living system. Synthetic biomaterials are materials which are not made by or do not originate from a living system. The biomaterials disclosed herein may be a combination of natural and synthetic biocompatible materials. As used herein, biomaterials include, for example, polymeric matrices and scaffolds. Those of ordinary skill in the art will appreciate that the biomaterial(s) may be configured in various forms, for example, as porous foam, gels, liquids, beads, solids, and may comprise one or more natural or synthetic biocompatible materials. In one embodiment, the biomaterial is the liquid form of a solution that is capable of becoming a hydrogel.

The term "kidney disease" as used herein refers to disorders associated with any stage or degree of acute or chronic renal failure that results in a loss of the kidney's ability to perform the function of blood filtration and elimination of excess fluid, electrolytes, and wastes from the blood. Kidney disease also includes endocrine dysfunctions such as anemia (erythropoietin-deficiency), and mineral imbalance (Vitamin D deficiency). Kidney disease may originate in the kidney or may be secondary to a variety of conditions, including (but not limited to) heart failure, hypertension, diabetes, autoimmune disease, or liver disease. Kidney disease may be a condition of chronic renal failure that develops after an acute injury to the kidney. For example, injury to the kidney by ischemia and/or exposure to toxicants may cause acute renal failure; incomplete recovery after acute kidney injury may lead to the development of chronic renal failure.

The term "treatment" refers to both therapeutic treatment and prophylactic or preventative measures for kidney disease, anemia, tubular transport deficiency, or glomerular filtration deficiency wherein the object is to reverse, prevent or slow down (lessen) the targeted disorder. Those in need of treatment include those already having a kidney disease, anemia, tubular transport deficiency, or glomerular filtration deficiency as well as those prone to having a kidney disease, anemia, tubular transport deficiency, or glomerular filtration deficiency or those in whom the kidney disease, anemia, tubular transport deficiency, or glomerular filtration deficiency is to be prevented. The term "treatment" as used herein includes the stabilization and/or improvement of kidney function.

The term "in vivo contacting" as used herein refers to direct contact in vivo between products secreted by an enriched population of cells and a native organ. For example, products secreted by an enriched population of renal cells (or an admixture or construct containing renal cells/renal cell fractions) may in vivo contact a native kidney. The direct in vivo contacting may be paracrine, endocrine, or juxtacrine in nature. The products secreted may be a heterogeneous population of different products described herein.

The terms "construct" or "formulation" refer to one or more cell populations deposited on or in a surface of a scaffold or matrix made up of one or more synthetic or naturally-occurring biocompatible materials. The one or more cell populations may be coated with, deposited on, embedded in, attached to, seeded, or entrapped in a biomaterial made up of one or more synthetic or naturally-occurring biocompatible biomaterials, polymers, proteins, or peptides. The one or more cell populations may be combined with a biomaterial or scaffold or matrix in vitro or in vivo. The one or more biomaterials used to generate the construct or formulation may be selected to direct, facilitate, or permit dispersion and/or integration of the cellular components of the construct with the endogenous host tissue, or to direct, facilitate, or permit the survival, engraftment, tolerance, or functional performance of the cellular components of the construct or formulation.

The term "Neo-Kidney Augment (NKA)" refers to a bioactive cell formulation which is an injectable product composed of autologous, homologous selected renal cells (SRC) formulated in a biomaterial comprised of a gelatin-based hydrogel. The term "Advance Cell Therapy (ACT)" refers to treatment with NKA.

The term "subject" shall mean any single human subject, including a patient, eligible for treatment, who is experiencing or has experienced one or more signs, symptoms, or other indicators of a kidney disease. Such subjects include without limitation subjects who are newly diagnosed or previously diagnosed and are now experiencing a recurrence or relapse, or are at risk for a kidney disease, no matter the cause. The subject may have been previously treated for a kidney disease, or not so treated.

The term "patient" refers to any single animal, more preferably a mammal (including such non-human animals as, for example, dogs, cats, horses, rabbits, zoo animals, cows, pigs, sheep, and non-human primates) for which treatment is desired. Most preferably, the patient herein is a human.

The term "sample" or "patient sample" or "biological sample" shall generally mean any biological sample obtained from a subject or patient, body fluid, body tissue, cell line, tissue culture, or other source. The term includes tissue biopsies such as, for example, kidney biopsies. The term includes cultured cells such as, for example, cultured mammalian kidney cells. Methods for obtaining tissue biopsies and cultured cells from mammals are well known in the art. If the term "sample" is used alone, it shall still mean that the "sample" is a "biological sample" or "patient sample", i.e., the terms are used interchangeably.

The term "test sample" refers to a sample from a subject that has been treated by a method of the present invention. The test sample may originate from various sources in the mammalian subject including, without limitation, blood, semen, serum, urine, bone marrow, mucosa, tissue, etc.

The term "control" or "control sample" refers a negative or positive control in which a negative or positive result is expected to help correlate a result in the test sample. Controls that are suitable for the present invention include, without limitation, a sample known to exhibit indicators characteristic of normal kidney function, a sample obtained from a subject known not to have kidney disease, and a sample obtained from a subject known to have kidney disease. In addition, the control may be a sample obtained from a subject prior to being treated by a method of the present invention. An additional suitable control may be a test sample obtained from a subject known to have any type or stage of kidney disease, and a sample from a subject known not to have any type or stage of kidney disease. A control may be a normal healthy matched control. Those of skill in the art will appreciate other controls suitable for use in the present invention.

"Regeneration prognosis", "regenerative prognosis", or "prognostic for regeneration" generally refers to a forecast or prediction of the probable regenerative course or outcome of the administration or implantation of a cell population, admixture or construct described herein. For a regeneration prognosis, the forecast or prediction may be informed by one or more of the following: improvement of a functional organ (e.g., the kidney) after implantation or administration, development of a functional kidney after implantation or administration, development of improved kidney function or capacity after implantation or administration, and expression of certain markers by the native kidney following implantation or administration.

"Regenerated organ" refers to a native organ after implantation or administration of a cell population, admixture, or construct as described herein. The regenerated organ is characterized by various indicators including, without limitation, development of function or capacity in the native organ, improvement of function or capacity in the native organ, and the expression of certain markers in the native organ. Those of ordinary skill in the art will appreciate that other indicators may be suitable for characterizing a regenerated organ.

"Regenerated kidney" refers to a native kidney after implantation or administration of a cell population, admixture, or construct as described herein. The regenerated kidney is characterized by various indicators including, without limitation, development of function or capacity in the native kidney, improvement of function or capacity in the native kidney, and the expression of certain markers in the native kidney. Those of ordinary skill in the art will appreciate that other indicators may be suitable for characterizing a regenerated kidney.

The term "hydrogel" is used herein to refer to a substance formed when an organic polymer (natural or synthetic) is cross-linked via covalent, ionic, or hydrogen bonds to create a three-dimensional open-lattice structure which entraps water molecules to form a gel. Examples of materials which can be used to form a hydrogel include polysaccharides such as alginate, polyphosphazines, and polyacrylates, which are crosslinked tonically, or block copolymers such as Pluronics™ or Tetronics™, polyethylene oxide-polypropylene glycol block copolymers which are crosslinked by temperature or pH, respectively. The hydrogel used herein is preferably a biodegradable gelatin-based hydrogel.

An "adverse event" is any unfavorable and unintended sign, symptom, or disease temporally associated with the use of an investigational (medicinal) product or other protocol-imposed intervention, regardless of attribution; and includes: AEs not previously observed in the patient that emerge during the protocol-specified AE reporting period, including signs or symptoms associated with chronic kidney disease that were not present before the AE reporting period; complications that occur as a result of protocol-mandated interventions (e.g., invasive procedures such as biopsies); or preexisting medical conditions (other than the condition being studied) judged by the investigator to have worsened in severity or frequency or changed in character during the protocol-specified AE reporting period.

An adverse event is classified as a "Serious Adverse Events" (SAE) if it meets the following criteria: results in death (i.e., the AE actually causes or leads to death); life threatening (i.e., the AE, in the view of the investigator, places the patient at immediate risk of death, but not including an AE that, had it occurred in a more severe form, might have caused death); requires or prolongs inpatient hospitalization; results in persistent or significant disability/incapacity (i.e., the AE results in substantial disruption of the patient's ability to conduct normal life functions); results in a congenital anomaly/birth defect in a neonate/infant born to a mother exposed to the investigational product; or is considered a significant medical event by the investigator based on medical judgment (e.g., may jeopardize the patient or may require medical/surgical intervention to prevent one of the outcomes listed above). All AEs that do not meet any of the criteria for serious are regarded as non-serious AEs. The terms "severe" and "serious" are not synonymous. Severity (or intensity) refers to the grade of a specific AE, e.g., mild (Grade 1), moderate (Grade 2), or severe (Grade 3) myocardial infarction. "Serious" is a regulatory definition (see previous definition) and is based on patient or event outcome or action criteria usually associated with events that pose a threat to a patient's life or functioning. Seriousness (not severity) serves as the guide for defining regulatory reporting obligations from the Sponsor to applicable regulatory authorities. Severity and seriousness should be independently assessed when recording AEs and SAEs on the eCRF Cell Populations As described above, BRCs are an isolated population of regenerative renal cells naturally involved in renal repair and regeneration. In one embodiment, BRCs are obtained from renal cells isolated from kidney tissue by enzymatic digestion and expanded using standard cell culture techniques. In one embodiment, the cell culture medium is designed to expand bioactive renal cells with regenerative capacity. In one other embodiment, the cell culture medium does not contain any differentiation factors. In another embodiment, the expanded heterogeneous mixtures of renal cells are cultured in hypoxic conditions to further enrich the composition of cells with regenerative capacity. Without wishing to be bound by theory, this may be due to one or more of the following phenomena: 1) selective survival, death, or proliferation of specific cellular components during the hypoxic culture period; 2) alterations in cell granularity and/or size in response to the hypoxic culture, thereby effecting alterations in buoyant density and subsequent localization during density gradient separation; and 3) alterations in cell gene/protein expression in response to the hypoxic culture period, thereby resulting in differential characteristics of the cells within the isolated and expanded population.

The expanded bioactive renal cells may be further subjected to density gradient separation to obtain the SRC. Specifically, density gradient centrifugation is used to separate harvested renal cell populations based on cell buoyant density. In one embodiment, the SRC are generated by using, in part, the OPTIPREP (Axis-Shield) density gradient medium, comprising 60% nonionic iodinated compound iodixanol in water. One of skill in the art, however, will recognize that any density gradient or other means, e.g., immunological separation using cell surface markers known in the art, comprising necessary features for isolating the cell populations of the instant invention may be used in accordance with the invention. In one embodiment, the cellular fraction exhibiting buoyant density greater than approximately 1.0419 g/mL is collected after centrifugation as a distinct pellet. In another embodiment, cells maintaining a buoyant density of less than 1.0419 g/mL are excluded and discarded.

The therapeutic compositions, and formulations thereof, of the present invention may contain isolated, heterogeneous populations of kidney cells, and admixtures thereof, enriched for specific bioactive components or cell types and/or depleted of specific inactive or undesired components or cell types for use in the treatment of kidney disease, i.e., providing stabilization and/or improvement and/or regeneration of kidney function and/or structure, were previously described in Presnell et al. U.S. 2011-0117162 and Ilagan et al. PCT/US2011/036347, the entire contents of which are incorporated herein by reference. The compositions may contain isolated renal cell fractions that lack cellular components as compared to a healthy individual yet retain therapeutic properties, i.e., provide stabilization and/or improvement and/or regeneration of kidney function. The cell populations, cell fractions, and/or admixtures of cells described herein may be derived from healthy individuals, individuals with a kidney disease, or subjects as described herein.

The present invention contemplates therapeutic compositions of selected renal cell populations that are to be administered to target organs or tissue in a subject in need. A bioactive selected renal cell population generally refers to a cell population potentially having therapeutic properties upon administration to a subject. For example, upon administration to a subject in need, a bioactive renal cell population can provide stabilization and/or improvement and/or repair and/or regeneration of kidney function in the subject. The therapeutic properties may include a repair or regenerative effect.

In one embodiment, the source of cells is the same as the intended target organ or tissue. For example, BRCs and/or SRCs may be sourced from the kidney to be used in a formulation to be administered to the kidney. In one embodiment, the cell populations are derived from a kidney biopsy. In another embodiment, the cell populations are derived from whole kidney tissue. In one other embodiment, the cell populations are derived from in vitro cultures of mammalian kidney cells, established from kidney biopsies or whole kidney tissue. In certain embodiments, the BRCs and/or SRCs comprise heterogeneous mixtures or fractions of bioactive renal cells. The BRCs and/or SRCs may be derived from or are themselves renal cell fractions from healthy individuals. In addition, the present invention provides renal cell fractions obtained from an unhealthy individual that may lack certain cellular components when compared to the corresponding renal cell fractions of a healthy individual, yet still retain therapeutic properties. The present invention also provides therapeutically-active cell populations lacking cellular components compared to a healthy individual, which cell populations can be, in one embodiment, isolated and expanded from autologous sources in various disease states.

In one embodiment, the SRCs are obtained from isolation and expansion of renal cells from a patient's renal cortical tissue via a kidney biopsy. Renal cells are isolated from the kidney tissue by enzymatic digestion, expanded using standard cell culture techniques, and selected by density gradient centrifugation from the expanded renal cells. In this embodiment, SRC are composed primarily of renal epithelial cells which are known for their regenerative potential. Other parenchymal (vascular) and stromal cells may be sparsely present in the autologous SRC population.

As described herein, the present invention is based, in part, on the surprising finding that certain subfractions of a heterogeneous population of renal cells, enriched for bioactive components and depleted of inactive or undesired components, provide superior therapeutic and regenerative outcomes than the starting population.

Renal cell isolation and expansion provides a mixture of renal cell types including renal epithelial cells and stromal cells. As noted above, SRC are obtained by density gradient separation of the expanded renal cells. The primary cell type in the density gradient separated SRC population is of tubular epithelial phenotype. The characteristics of SRC obtained from expanded renal cells is evaluated using multipronged approach. Cell morphology, growth kinetics and cell viability are monitored during the renal cell expansion process. SRC buoyant density and viability is characterized by density gradient and Trypan Blue exclusion. SRC phenotype is characterized by flow cytometry and SRC function is demonstrated by expression of VEGF and KIM-1. Cell function of SRC, pre-formulation, can also be evaluated by measuring the activity of two specific enzymes; GGT (γ-glutamyl transpeptidase) and LAP (leucine aminopeptidase), found in kidney proximal tubules.

Although selected renal cell compositions are described herein, the present invention contemplates compositions containing a variety of other active agents. Other suitable active agents include, without limitation, cellular aggregates, acellular biomaterials, secreted products from bioactive cells, large and small molecule therapeutics, as well as combinations thereof. For example, one type of bioactive cells may be combined with biomaterial-based microcarriers with or without therapeutic molecules or another type of bioactive cells, unattached cells may be combined with acellular particles.

Biomaterials

A variety of biomaterials may be combined with an active agent to provide the therapeutic formulations of the present invention. The biomaterials may be in any suitable shape (e.g., beads) or form (e.g., liquid, gel, etc.). Suitable biomaterials in the form of polymeric matrices are described in Bertram et al. U.S. Published Application 20070276507 (incorporated herein by reference in its entirety). In one embodiment, the polymeric matrix may be a biocompatible material formed from a variety of synthetic or naturally-occurring materials including, but not limited to, open-cell polylactic acid (OPLA®), cellulose ether, cellulose, cellulosic ester, fluorinated polyethylene, phenolic, poly-4-methylpentene, polyacrylonitrile, polyamide, polyamideimide, polyacrylate, polybenzoxazole, polycarbonate, polycyanoarylether, polyester, polyestercarbonate, polyether, polyetheretherketone, polyetherimide, polyetherketone, polyethersulfone, polyethylene, polyfluoroolefin, polyimide, polyolefin, polyoxadiazole, polyphenylene oxide, polyphenylene sulfide, polypropylene, polystyrene, polysulfide, polysulfone, polytetrafluoroethylene, polythioether, polytriazole, polyurethane, polyvinyl, polyvinylidene fluoride, regenerated cellulose, silicone, urea-formaldehyde, collagens, gelatin, alginate, laminins, fibronectin, silk, elastin, alginate, hyaluronic acid, agarose, or copolymers or physical blends thereof. In a preferred embodiment, the biomaterial is a hydrogel.

Hydrogels may be formed from a variety of polymeric materials and are useful in a variety of biomedical applications. Hydrogels can be described physically as three-dimensional networks of hydrophilic polymers. Depending on the type of hydrogel, they contain varying percentages of water, but altogether do not dissolve in water. Despite their high water content, hydrogels are capable of additionally binding great volumes of liquid due to the presence of hydrophilic residues. Hydrogels swell extensively without changing their gelatinous structure. The basic physical features of hydrogel can be specifically modified, according to the properties of the polymers used and the additional special equipments of the products.

The hydrogel material preferably does not induce an inflammatory response. Examples of other materials which can be used to form a hydrogel include (a) modified alginates, (b) polysaccharides (e.g. gellan gum and carrageenans) which gel by exposure to monovalent cations, (c) polysaccharides (e.g., hyaluronic acid) that are very viscous liquids or are thixotropic and form a gel over time by the slow evolution of structure, (d) gelatin or collagen, and (e) polymeric hydrogel precursors (e.g., polyethylene oxide-polypropylene glycol block copolymers and proteins). U.S. Pat. No. 6,224,893 B1 provides a detailed description of the various polymers, and the chemical properties of such polymers, that are suitable for making hydrogels in accordance with the present invention.

In a particular embodiment, the hydrogel used to formulate the biomaterials of the present invention is gelatin-based. Gelatin is a non-toxic, biodegradable and water-soluble protein derived from collagen, which is a major component of mesenchymal tissue extracellular matrix (ECM). Gelatin retains informational signals including an arginine-glycine-aspartic acid (RGD) sequence, which promotes cell adhesion, proliferation and stem cell differentiation. A characteristic property of gelatin is that it exhibits Upper Critical Solution Temperature behavior (UCST). Above a specific temperature threshold of 40° C., gelatin can be dissolved in water by the formation of flexible, random single coils. Upon cooling, hydrogen bonding and Van der Waals interactions occur, resulting in the formation of triple helices. These collagen-like triple helices act as junction zones and thus trigger the sol-gel transition. Gelatin is widely used in pharmaceutical and medical applications.

The biomaterials described herein may also be designed or adapted to respond to certain external conditions, e.g., in vitro or in vivo. In one embodiment, the biomaterials are temperature-sensitive (e.g., either in vitro or in vivo). In another embodiment, the biomaterials are adapted to respond to exposure to enzymatic degradation (e.g., either in vitro or in vivo). The biomaterials' response to external conditions can be fine-tuned as described herein. Temperature sensitivity of the formulation described can be varied by adjusting the percentage of a biomaterial in the formulation. For example, the percentage of gelatin in a solution can be adjusted to modulate the temperature sensitivity of the gelatin in the final formulation (e.g., liquid, gel, beads, etc.). In one embodiment, the gelatin solution may be provided in PBS, DMEM, or another suitable solvent. Alternatively, biomaterials may be chemically cross-linked to provide greater resistance to enzymatic degradation. For instance, a carbodiimide crosslinker may be used to chemically cross-link gelatin beads thereby providing a reduced susceptibility to endogenous enzymes.

In one aspect, the formulations described herein incorporate biomaterials having properties which create a favorable environment for the active agent, such as bioactive renal cells, to be administered to a subject. In one embodiment, the formulation contains a first biomaterial that provides a favorable environment from the time the active agent is formulated with the biomaterial up until the point of administration to the subject. In one other embodiment, the favorable environment concerns the advantages of having bioactive cells suspended in a substantially solid state versus cells in a fluid (as described herein) prior to administration to a subject. In another embodiment, the first biomaterial is a temperature-sensitive biomaterial. The temperature-sensitive biomaterial may have (i) a substantially solid state at about 8° C. or below, and (ii) a substantially liquid state at ambient temperature or above. In one embodiment, the ambient temperature is about room temperature. The cell populations and preparations described herein may be coated with, deposited on, embedded in, attached to, seeded, suspended in, or entrapped in a temperature-sensitive biomaterial.

In another aspect, the present invention provides formulations that contain biomaterials which degrade over a period time on the order of minutes, hours, or days. This is in contrast to a large body or work focusing on the implantation of solid materials that then slowly degrade over days, weeks, or months. In one embodiment, the biomaterial has one or more of the following characteristics: biocompatibility, biodegradeable/bioresorbable, a substantially solid state prior to and during implantation into a subject, loss of structural integrity (substantially solid state) after implantation, and cytocompatible environment to support cellular viability. The biomaterial's ability to keep implanted particles spaced out during implantation enhances native tissue ingrowth. The biomaterial also facilitates implantation of solid formulations. The biomaterial provides for localization of the formulation described herein since inserted of a solid unit helps prevent the delivered materials from dispersing within the tissue during implantation. For cell-based formulations, a solid biomaterial also improves stability and viability of anchorage dependent cells compared to cells suspended in a fluid. However, the short duration of the structural integrity means that soon after implantation, the biomaterial does not provide a significant barrier to tissue ingrowth or integration of the delivered cells/materials with host tissue.

Bioactive Cell Formulations

The bioactive cell formulations described herein contain implantable constructs made from the above-referenced biomaterials having the bioactive renal cells described herein for the treatment of kidney disease in a subject in need. In one embodiment, the construct is made up of a biocompatible material or biomaterial, scaffold or matrix composed of one or more synthetic or naturally-occurring biocompatible materials and one or more cell populations or admixtures of cells described herein deposited on or embedded in a surface of the scaffold by attachment and/or entrapment. In certain embodiments, the construct is made up of a biomaterial and one or more cell populations or admixtures of cells described herein coated with, deposited on, deposited in, attached to, entrapped in, embedded in, seeded, or combined with the biomaterial component(s). Any of the cell populations described herein, including enriched cell populations or admixtures thereof, may be used in combination with a matrix to form a construct. In one embodiment, the bioactive cell formulation is made up of a biocompatible material or biomaterial and an SRC population described herein.

In one embodiment, the bioactive cell formulation is a Neo-Kidney Augment (NKA), which is an injectable product composed of autologous, homologous selected renal cells (SRC) formulated in a Biomaterial (gelatin-based hydrogel). In one aspect, autologous, homologous SRC are obtained from isolation and expansion of renal cells from the patient's renal cortical tissue via a kidney biopsy and selection by density gradient centrifugation from the expanded renal cells. SRC are composed primarily of renal epithelial cells which are well known for their regenerative potential (Humphreys et al. (2008) Intrinsic epithelial cells repair the kidney after injury. Cell Stem Cell. 2 (3): 284-91). Injection of SRC into recipient kidneys has resulted in significant improvement in animal survival, urine concentration and filtration functions in nonclinical studies. However, SRC have limited shelf life and stability. Formulation of SRC in a gelatin-based hydrogel biomaterial provides enhanced stability of the cells thus extending product shelf life, improved stability of NKA during transport and delivery of NKA into the kidney cortex for clinical utility.

In another aspect, NKA is manufactured by first obtaining renal cortical tissue from the donor/recipient using a standard-of-clinical-care kidney biopsy procedure. Renal cells are isolated from the kidney tissue by enzymatic digestion and expanded using standard cell culture techniques. Cell culture medium is designed to expand primary renal cells and does not contain any differentiation factors. Harvested renal cells are subjected to density gradient separation to obtain SRC.

One aspect of the invention further provides a formulation made up of biomaterials designed or adapted to respond to external conditions as described herein. As a result, the nature of the association of the bioactive cell population with the biomaterial in a construct will change depending upon the external conditions. For example, a cell population's association with a temperature-sensitive biomaterial varies with temperature. In one embodiment, the construct contains a bioactive renal cell population and biomaterial having a substantially solid state at about 8° C. or lower and a substantially liquid state at about ambient temperature or above, wherein the cell population is suspended in the biomaterial at about 8° C. or lower.

However, the cell population is substantially free to move throughout the volume of the biomaterial at about ambient temperature or above. Having the cell population suspended in the substantially solid phase at a lower temperature provides stability advantages for the cells, such as for anchorage-dependent cells, as compared to cells in a fluid. Moreover, having cells suspended in the substantially solid state provides one or more of the following benefits: i) prevents settling of the cells, ii) allows the cells to remain anchored to the biomaterial in a suspended state; iii) allows the cells to remain more uniformly dispersed throughout the volume of the biomaterial; iv) prevents the formation of cell aggregates; and v) provides better protection for the cells during storage and transportation of the formulation. A formulation that can retain such features leading up to the administration to a subject is advantageous at least because the overall health of the cells in the formulation will be better and a more uniform and consistent dosage of cells will be administered.

In certain embodiments, the manufacturing process for the bioactive cell formulations is designed to deliver a product in approximately four weeks from patient biopsy to product implant. Inherent patient-to-patient tissue variability poses a challenge to deliver product on a fixed implant schedule. Expanded renal cells are routinely cryopreserved during cell expansion to accommodate for this patient-dependent variation in cell expansion. Cryopreserved renal cells provide a continuing source of cells in the event that another treatment is needed (e.g., delay due to patient sickness, unforeseen process events, etc.) and to manufacture multiple doses for re-implantation, as required.

For embodiments where the bioactive cell formulation is composed of autologous, homologous cells formulated in a biomaterial (gelatin-based hydrogel), the final composition may be about $20 \times 10^6$ cells per mL to about $200 \times 10^6$ cells per mL in a gelatin solution with Dulbecco's Phosphate Buffered Saline (DPBS). In some embodiments, the number of cells per mL of product is about $20 \times 10^6$ cells per mL, about $40 \times 10^6$ cells per mL, about $60 \times 10^6$ cells per mL, about $100 \times 10^6$ cells per mL, about $120 \times 10^6$ cells per mL, about $140 \times 10^6$ cells per mL, about $160 \times 10^6$ cells per mL, about $180 \times 10^6$ cells per mL, or about $200 \times 10^6$ cells per mL. In some embodiments, the gelatin is present at about 0.5%, about 0.55%, about 0.6%, about 0.65%, about 0.7%, about 0.75%, about 0.8%, about 0.85%, about 0.9%, about 0.95% or about 1%, (w/v) in the solution. In one example, the biomaterial is a 0.88% (w/v) gelatin solution in DPBS.

In a preferred embodiment, NKA is presented in a sterile, single-use 10 ml syringe. The final volume is calculated from the concentration of $100 \times 10^6$ SRC/mL of NKA and the target dose of $3.0 \times 10^6$ SRC/g kidney weight (estimated by MRI). Therapeutic dosage may also be determined by the surgeon at the time of injection based on the patient's kidney weight.

A total number of cells may be selected for the formulation and the volume of the formulation may be adjusted to reach the proper therapeutic dosage. In some embodiments, the formulation may contain a dosage of cells to a subject that is a single dosage or a single dosage plus additional dosages. In other embodiments, the dosages may be provided by way of a construct as described herein. The therapeutically effective amount of the bioactive renal cell populations or admixtures of renal cell populations described herein can range from the maximum number of cells that is safely received by the subject to the minimum number of cells necessary for treatment of kidney disease, e.g., stabilization, reduced rate-of-decline, or improvement of one or more kidney functions.

The therapeutically effective amount of the bioactive renal cell populations or admixtures thereof described herein can also be suspended in a pharmaceutically acceptable carrier or excipient. Such a carrier includes, but is not limited to basal culture medium plus 1% serum albumin, saline, buffered saline, dextrose, water, collagen, alginate, hyaluronic acid, fibrin glue, polyethyleneglycol, polyvinylalcohol, carboxymethylcellulose and combinations thereof. The formulation should suit the mode of administration.

The bioactive renal cell preparation(s), or admixtures thereof, or compositions are formulated in accordance with routine procedures as a pharmaceutical composition adapted for administration to human beings. Typically, compositions for intravenous administration, intra-arterial administration or administration within the kidney capsule, for example, are solutions in sterile isotonic aqueous buffer. Where necessary, the composition can also include a local anesthetic to ameliorate any pain at the site of the injection. Generally, the ingredients are supplied either separately or mixed together in unit dosage form, for example, as a cryopreserved concentrate in a hermetically sealed container such as an ampoule indicating the quantity of active agent. When the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

Pharmaceutically acceptable carriers are determined in part by the particular composition being administered, as well as by the particular method used to administer the composition. Accordingly, there are a wide variety of suitable formulations of pharmaceutical compositions (sec, e.g., Alfonso R Gennaro (ed), Remington: The Science and Practice of Pharmacy, formerly Remington's Pharmaceutical Sciences 20th ed., Lippincott, Williams & Wilkins, 2003, incorporated herein by reference in its entirety). The pharmaceutical compositions are generally formulated as sterile, substantially isotonic and in full compliance with all Good Manufacturing Practice (GMP) regulations of the U.S. Food and Drug Administration.

In one aspect, the bioactive cell formulation also includes a cell viability agent. selected from the group consisting of an antioxidant, an oxygen carrier, an immunomodulatory factor, a cell recruitment factor, a cell attachment factor, an anti-inflammatory agent, an angiogenic factor, a wound healing factor, and products secreted from bioactive cells.

Methods of Use

In one aspect, the constructs and formulations of the present invention are suitable for use in the methods of use described herein. In one embodiment, the formulations of the present invention may be administered for the treatment of disease. For example, bioactive cells may be administered to a native organ as part of a formulation described herein. In one embodiment, the bioactive cells may be sourced from the native organ that is the subject of the administration or from a source that is not the target native organ.

In one embodiment, the present invention provides methods for the treatment of a kidney disease, in a subject in need with the formulations containing bioactive renal cell populations as described herein. In another embodiment, the therapeutic formulation contains a selected renal cell population or admixtures thereof. In all embodiments, the formulations are suitable for administration to a subject in need of improved kidney function.

In another aspect, the effective treatment of a kidney disease in a subject by the methods of the present invention can be observed through various indicators of kidney function. In one embodiment, the indicators of kidney function include, without limitation, serum albumin, albumin to globulin ratio (A/G ratio), serum phosphorous, serum sodium, kidney size (measurable by ultrasound), serum calcium, phosphorous:calcium ratio, serum potassium, proteinuria, urine creatinine, serum creatinine, blood nitrogen urea (BUN), cholesterol levels, triglyceride levels and glomerular filtration rate (GFR). Furthermore, several indicators of general health and well-being include, without limitation, weight gain or loss, survival, blood pressure (mean systemic blood pressure, diastolic blood pressure, or systolic blood pressure), and physical endurance performance.

In another aspect, an effective treatment with a bioactive renal cell formulation is evidenced by stabilization of one or more indicators of kidney function. The stabilization of kidney function is demonstrated by the observation of a change in an indicator in a subject treated by a method of the present invention as compared to the same indicator in a subject that has not been treated by a method of the present invention. Alternatively, the stabilization of kidney function may be demonstrated by the observation of a change in an indicator in a subject treated by a method of the present invention as compared to the same indicator in the same subject prior to treatment. The change in the first indicator may be an increase or a decrease in value. In one embodiment, the treatment provided by the present invention may include stabilization of serum creatinine levels in a subject where the BUN levels observed in the subject are lower as compared to a subject with a similar disease state who has not been treated by the methods of the present invention. In one other embodiment, the treatment may include stabilization of serum creatinine levels in a subject where the serum creatinine levels observed in the subject are lower as compared to a subject with a similar disease state who has not been treated by the methods of the present invention. In one embodiment, the stabilization of one or more of the above indicators of kidney function is the result of treatment with a selected renal cell formulation.

Those of ordinary skill in the art will appreciate that one or more additional indicators described herein or known in the art may be measured to determine the effective treatment of a kidney disease in the subject.

In another aspect, an effective treatment with a bioactive renal cell formulation is evidenced by improvement of one or more indicators of kidney function. In one embodiment, the bioactive renal cell population provides an improved level of serum creatinine). In another embodiment, the bioactive renal cell population provides an improved retention of protein in the serum. In another embodiment, the bioactive renal cell population provides improved levels of serum cholesterol and/or triglycerides. In another embodiment, the bioactive renal cell population provides an improved level of Vitamin D. In one embodiment, the bioactive renal cell population provides an improved phosphorus:calcium ratio as compared to a non-enriched cell population. In another embodiment, the bioactive renal cell population provides an improved level of hemoglobin as compared to a non-enriched cell population. In a further embodiment, the bioactive renal cell population provides an improved level of serum creatinine as compared to a non-enriched cell population. In one embodiment, the improvement of one or more of the above indicators of kidney function is the result of treatment with a selected renal cell formulation.

In another aspect, the present invention provides formulations for use in methods for the regeneration of a native kidney in a subject in need thereof. In one embodiment, the method includes the step of administering or implanting a bioactive cell population, admixture, or construct described herein to the subject. A regenerated native kidney may be characterized by a number of indicators including, without limitation, development of function or capacity in the native kidney, improvement of function or capacity in the native kidney, and the expression of certain markers in the native kidney. In one embodiment, the developed or improved function or capacity may be observed based on the various indicators of kidney function described above. In another embodiment, the regenerated kidney is characterized by differential expression of one or more stem cell markers. The stem cell marker may be one or more of the following: SRY (sex determining region Y)-box 2 (Sox2); Undifferentiated Embryonic Cell Transcription Factor (UTF1); Nodal Homolog from Mouse (NODAL); Prominin 1 (PROM1) or CD133 (CD133); CD24; and any combination thereof (see Ilagan et al. PCT/US2011/036347 incorporated herein by reference in its entirety). In another embodiment, the expression of the stem cell marker(s) is up-regulated compared to a control.

In another embodiment, the effect may be provided by the cells themselves and/or by products secreted from the cells. The regenerative effect may be characterized by one or more of the following: a reduction in epithelial-mesenchymal transition (which may be via attenuation of TGF-β signaling); a reduction in renal fibrosis; a reduction in renal inflammation; differential expression of a stem cell marker in the native kidney; migration of implanted cells and/or native cells to a site of renal injury, e.g., tubular injury, engraftment of implanted cells at a site of renal injury, e.g., tubular injury; stabilization of one or more indicators of kidney function (as described herein); restoration of erythroid homeostasis (as described herein); and any combination thereof.

As an alternative to a tissue biopsy, a regenerative outcome in the subject receiving treatment can be assessed from examination of a bodily fluid, e.g., urine. It has been discovered that microvesicles obtained from subject-derived urine sources contain certain components including, without limitation, specific proteins and miRNAs that are ultimately derived from the renal cell populations impacted by treatment with the cell populations of the present invention. These components may include factors involved in stem cell replication and differentiation, apoptosis, inflammation and immuno-modulation. A temporal analysis of microvesicle-associated miRNA/protein expression patterns allows for continuous monitoring of regenerative outcomes within the kidney of subjects receiving the cell populations, admixtures, or constructs of the present invention.

In another embodiment, the present invention provides methods of assessing whether a kidney disease (KD) patient is responsive to treatment with a therapeutic formulation. The method may include the step of determining or detecting the amount of vesicles or their luminal contents in a test sample obtained from a KD patient treated with the therapeutic, as compared to or relative to the amount of vesicles in a control sample, wherein a higher or lower amount of vesicles or their luminal contents in the test sample as compared to the amount of vesicles or their luminal contents in the control sample is indicative of the treated patient's responsiveness to treatment with the therapeutic.

These kidney-derived vesicles and/or the luminal contents of kidney derived vesicles may also be shed into the urine of a subject and may be analyzed for biomarkers indicative of regenerative outcome or treatment efficacy. The non-invasive prognostic methods may include the step of obtaining a urine sample from the subject before and/or after administration or implantation of a cell population, admixture, or construct described herein. Vesicles and other secreted products may be isolated from the urine samples using standard techniques including without limitation, centrifugation to remove unwanted debris (Zhou et al. 2008. Kidney Int. 74 (5): 613-621; Skog et al. U.S. Published Patent Application No. 20110053157, each of which is incorporated herein by reference in its entirety).

Methods and Routes of Administration

The bioactive cell formulations of the present invention can be administered alone or in combination with other bioactive components. The formulations are suitable for injection or implantation of incorporated tissue engineering elements to the interior of solid organs to regenerate tissue. In addition, the formulations are used for the injection or implantation of tissue engineering elements to the wall of hollow organs to regenerate tissue.

In one aspect, the present invention provides methods of providing a bioactive cell formulation described herein to a subject in need. In one embodiment, the source of the bioactive cell may be autologous or allogeneic, syngeneic (autogeneic or isogeneic), and any combination thereof. In instances where the source is not autologous, the methods may include the administration of an immunosuppressant agent. (see e.g. U.S. Pat. No. 7,563,822).

The treatment methods of the subject invention involve the delivery of a bioactive cell formulation described herein. In one embodiment, direct administration of cells to the site of intended benefit is preferred. A subject in need may also be treated by in vivo contacting of a native kidney with a bioactive cell formulation described herein together with products secreted from one or more enriched renal cell populations, and/or an admixture or construct containing the same. The step of in vivo contacting provides a regenerative effect to the native kidney.

A variety of means for administering compositions of selected renal cells to subjects will, in view of this specification, be apparent to those of skill in the art. Such methods include injection of the cells into a target site in a subject.

Modes of administration of the formulations include, but are not limited to, systemic, intra-renal (e.g., parenchymal), intravenous or intra-arterial injection and injection directly into the tissue at the intended site of activity. Additional modes of administration to be used in accordance with the present invention include single or multiple injection(s) via direct laparotomy, via direct laparoscopy, transabdominal, or percutaneous. Still yet additional modes of administration to be used in accordance with the present invention include, for example, retrograde and ureteropelvic infusion. Surgical means of administration include one-step procedures such as, but not limited to, partial nephrectomy and construct implantation, partial nephrectomy, partial pyelectomy, vascularization with omentum±peritoneum, multifocal biopsy needle tracks, cone or pyramidal, to cylinder, and renal pole-like replacement, as well as two-step procedures including, for example, organoid-internal bioreactor for replanting. In one embodiment, the formulations containing admixtures of cells are delivered via the same route at the same time. In another embodiment, each of the cell compositions comprising the controlled admixture are delivered separately to specific locations or via specific methodologies, either simultaneously or in a temporally-controlled manner, by one or more of the methods described herein. In one embodiment, the selected renal cells are percutaneously injected into the renal cortex of a kidney. In another embodiment, a guiding cannula is inserted percutaneously and used to puncture the kidney capsule prior to injection of the composition into the kidney.

A laparoscopic or percutaneous technique may be used to access the kidney for injection of formulated BRC or SRC population. Use of laparoscopic surgical techniques allows for direct visualization of the kidney so that any bleeding or other adverse events can be spotted during injection and addressed immediately. Use of a percutaneous approach to the kidney has been in use for over a decade, primarily for ablating intrarenal masses. These procedures insert an electrode or cryogenic needle into a defined mass in the kidney, and remain in contact for (typically) 10 to 20 minutes while the lesion is ablated. For injection of the therapeutic formulation, the percutaneous instrumentation is no larger nor more complex, and this approach offers the safety advantages of no surgery (avoiding abdominal puncture wounds and inflation with gas) and minimal immobilization time. Furthermore, the access track can have hemostatic biodegradable material left in place, to further reduce any chance of significant bleeding.

According to one embodiment of the delivery by injection, the therapeutic bioactive cell formulation is injected into the renal cortex. It is important to distribute the therapeutic formulation in the renal cortex as widely as possible, which can be achieved, for example, by entering the renal cortex at an angle allowing deposition of the therapeutic formulation in the renal cortex, distributed as widely as feasible. This could require imaging the kidney in a longitudinal or transverse approach using ultrasound guidance or with axial computed tomography (CT) imaging, depending upon individual patient characteristics. Ideally the injection will involve multiple deposits as the injection needle/cannula is gradually withdrawn. The full volume of the therapeutic formulation may be deposited at a single or multiple entry points. In one embodiment, up to two entry points may be used to deposit the full volume of therapeutic formulation into the kidney. In one embodiment, the injection may be administered to a single kidney, using one or more entry points, e.g. one or two entry points. In another embodiment, the injection is made into both kidneys, in each kidney using one or more entry point, e.g. one or two entry points.

Chronic Kidney Disease

Chronic Kidney Disease (CKD) is characterized by progressive nephropathy that without therapeutic intervention will worsen until the patient reaches end stage renal disease (ESRD). It is defined as reduced kidney function, demonstrated by decreased estimated glomerular filtration (eGFR) or evidence of kidney damage, such as increased excretion of urinary albumin. Global prevalence of CKD is estimated at 8-16%. (Jha et al. Chronic kidney disease: global dimension and perspectives. *Lancet.* 2013; 382:260-72.) CKD is associated with considerable morbidity, such as diabetes mellitus, (Postma and de Zeeuw. The economic benefits of preventing end-stage renal disease in patients with type 2 diabetes mellitus. *Nephrol Dial Transplant.* 2009; 24:2975-2983) and is often accompanied by adverse outcomes owing to underlying disease states or and/or risk factors such as hypertension and renovascular disease. (Khan et al. Health care utilization among patients with chronic kidney disease. *Kidney Int.* 2002; 62:229-236) Ninety-seven percent of patients with moderate to severe CKD have mostly asymptomatic Stage 3 disease, but even this stage of CKD bears a two-to four-fold rise in cardiovascular disease risk along with a significant increase in all-cause mortality. (Keith et al. Longitudinal follow-up and outcomes among a population with chronic kidney disease in a large managed care organization. *Arch Intern Med.* 2004; 164:659-63; Gansevoort et al. Chronic kidney disease and cardiovascular risk: epidemiology, mechanisms, and prevention. *Lancet.* 2013; 382: 339-52) Only a small proportion of patients progress to ESRD (ie, Stage 5 disease); even with costly treatments, however, patients with ESRD experience substantial morbidity and mortality. (Keith et al. Longitudinal follow-up and outcomes among a population with chronic kidney disease in a large managed care organization. *Arch Intern Med.* 2004; 164:659-63) To survive, ESRD patients require renal replacement therapy (dialysis or kidney transplantation). Preventing or delaying adverse outcomes of CKD via early intervention is the primary strategy in CKD management. (National Institute for Health and Clinical Excellence (NICE). Chronic kidney disease: early identification and management of chronic kidney disease in adults in primary and secondary care (CG182) London: NICE; 2014) Nevertheless, early treatments have been less than optimal, resulting in a significant unmet medical need for improved interventional strategies to manage CKD and delay progression to ESRD.

Progressive Staging of CKD

The major causes of CKD are diabetes and hypertension. Nearly half of all CKD cases arise from diabetes with or without hypertension. (Postma and de Zeeuw. The economic benefits of preventing end-stage renal disease in patients with type 2 diabetes mellitus. *Nephrol Dial Transplant.* 2009; 24:2975-2983; Gansevoort et al. Chronic kidney disease and cardiovascular risk: epidemiology, mechanisms, and prevention. *Lancet.* 2013; 382:339-52) The incidence of CKD continues to increase, primarily due to the increased incidence of Type 2 Diabetes Mellitus (T2DM). (Postma and de Zeeuw. *Nephrol Dial Transplant.* 2009; 24:2975-2983)

Staging and grading of kidney function is most often quantified by the estimated glomerular filtration rate (GFR), which is defined as "the volume of plasma from which a given substance is completely cleared by glomerular filtration per unit time". (Stevens et al. Assessing kidney function—Measured and estimated glomerular filtration rate. *New Engl J Med.* 2006; 354:2473-83) Creatinine clearance is the principal endogenous marker that is used to measure GFR. In February 2002, with the aim of providing a uniform definition of CKD, the Kidney Disease Outcomes Quality Initiative of the US Kidney Foundation defined CKD and the various stages of CKD (Table 1) (Levey et al. National Kidney Foundation practice guidelines for chronic kidney disease: evaluation, classification, and stratification. *Ann Int Med.* 2003; 139:137-47). For example, the threshold for CKD is 60 mL/min/1.73 m², which is less than one-half of the GFR for a normal, young adult male (120-130 mL/min/ 1.73 m²). (Levey et al. Definition and classification of chronic kidney disease: apposition statement from Kidney Disease Improving Global Outcomes (KDIGO). *Kidney Int.* 2005; 67:2089-100) Additionally, there is a heightened risk for CKD complications when the GFR is 60 ml/min/1.73 m² and lower.

Table 1 defines CKD stages according to GFR measurements, and the relative prevalence and clinical action taken at each stage. (National Kidney Foundation, 2002. KDOQI clinical practice guidelines for chronic kidney disease: evaluation, classification, and stratification. *Am J Kidney Dis.* 39: S1-266) The initial stage of diabetic nephropathy (Stage 1) occurs over a period of several years and is characterized by microalbuminuria (30-300 mg/24 hr) followed by macroalbuminuria (>300 mg/24 hr). As the ability of the kidney to filter blood waste products declines, serum creatinine rises. With increasing kidney damage (Stages 2-4), rising blood pressure further exacerbates kidney disease. When the kidneys cease to function entirely (Stage 5 [ESRD]), renal replacement therapy (dialysis or transplantation) is required.

TABLE 1

Summary of Classification and Prevalence Estimates for CKD

| Stage* | Description | GFR (mL/min/1.73 m²) |
|---|---|---|
| 1 | Kidney damage with normal or increased GFR | ≥90 |
| 2 | Kidney damage with mild decrease in GFR | 60-89 |
| 3 | Moderate decrease in GFR | 30-59 |
| 4 | Severe decrease in GFR | 15-29 |
| 5 | Kidney failure | <15 (or dialysis) |

*Source: National Kidney Foundation, 2002. National Kidney Foundation. 2002. KDOQI clinical practice guidelines for chronic kidney disease: evaluation, classification, and stratification. *Am J Kidney Dis.* 39:S1-266.

All-cause mortality rates were shown to increase as GFR declined; mortality rates were highest at Stages 4-5 of CKD. (Go et al. Chronic kidney disease and the risks of death, cardiovascular events, and hospitalization. *N Engl J Med.* 2004; 351:1296-305; Astor et al. Glomerular filtration rate, albuminuria, and risk of cardiovascular and all-cause mortality in the US population. *Am J Epidemiol.* 2008; 167: 1226-34; Kovesdy et al. Association of kidney function with mortality in patients with chronic kidney disease not yet on dialysis: a historical prospective cohort study. *Adv Chronic Kidney Dis.* 2006; 13:183-88) Populations defined as having an eGFR <60 mL/min/1.73 m² consistently exhibited a higher mortality rate than comparator groups where there was no evidence of CKD.

Standard-of-Care in CKD

Treatment of patients with CKD is focused on slowing progression and preparing for kidney failure/replacement. For many patients, CKD occurs as part of a complex comorbidity cluster, especially with cardiovascular disease and T2DM.

Increased risk of cardiovascular disease can be a complication of CKD or an independent comorbidity associated with T2DM. (Gerstein et al. Albuminuria and risk of cardiovascular events, death, and heart failure in diabetic and nondiabetic individuals. *JAMA.* 2001; 286:421-26) Collectively, the aim is to lower cardiovascular risk and prevent or slow the progression of kidney failure via administration of: 1) angiotensin converting enzyme inhibitors (ACEI) and/or angiotensin receptor blockers (ARB) to decrease proteinuria and control hypertension; 2) insulin and anti-diabetic agents for glycemic control (eg, reduced serum hemoglobin $A_{1c}$); and, 3) statin therapy to counter dyslipidemia.

When a patient reaches ESRD, renal replacement therapy (ie, dialysis or transplantation) is indicated. The vast majority of Stage 5 patients receive hemodialysis. (Dhingra et al. Type of vascular access and mortality in US hemodialysis patients. *Kidney Int.* 2001; 60:1443-51) Dialysis replaces about 5-15% of kidney function, depending on the intensity and frequency of use; dialysis also helps to restore fluid and electrolyte balance when kidneys fail. However, the life-expectancy of an ESRD patient initiating hemodialysis is only 4-5 years. (US Renal Data System. 2012 Annual data report: Atlas of chronic kidney disease and end-stage renal disease in the US. National Institutes of Health, National Institute of Diabetes and Digestive and Kidney Diseases, Bethesda, MD) Additionally, hemodialysis has been associated with multiple, serious complications as well as interference with quality of life, such as the need to undergo dialysis up to three times per week. Although kidney transplantation remains the most effective form of therapy at this time; there is a chronic shortage of organs. If a patient is able to secure a kidney for transplantation, long-term immunosuppressive therapy is required to prevent rejection. Use of these regimens results in a higher incidence of infection and, over the long term, some types of cancer. (Almeida et al. Safety of immunosuppressive drugs used as maintenance therapy in kidney transplantation: a systematic review and meta-analysis. *Pharmaceuticals (Basel)*. 2013; 6:1170-94) Taken together, there is a critical medical need for improved therapies for CKD which could dramatically slow the progression of disease and significantly delay the need for renal transplantation.

Therapeutic Product

The Neo Kidney Augment™ (NKA) is being developed based on extensive scientific evaluation of its biologically active component known as SRC (ie, homologous, autologous selected renal cells). This cell population is naturally involved in renal repair and regeneration. (Bruce et al. Selected renal cells modulate disease progression in rodent models of chronic kidney disease via NF-κB and TGF-β1 pathways. *Regen Med.* 2015; 10:815-39; Bruce et al. Exposure of cultured human renal cells induces mediators of cell migration and attachment and facilitates the repair of tubular cell monolayers in vitro. Experimental Biology Meeting, Washington, DC, 2011; Genheimer et al. Molecular characterization of the regenerative response induced by intrarenal transplantation of selected renal cells in a rodent model of chronic kidney disease. *Cells Tissues Organs.* 2012; 196: 374-84; Ilagan et al. Exosomes derived from primary renal cells contain microRNAs that can potentially drive therapeutically-relevant outcomes in models of chronic kidney disease. TERMIS Conference, Orlando, FL, 2010; Ilagan et al. Secreted factors from bioactive kidney cells attenuate NF-kappa-B. TERMIS Conference, Orlando, FL, 2010; Ilagan et al. Characterization of primary adult canine renal cells (CRC) in a three-dimensional (3D) culture system permissive for ex vivo nephrogenesis. KIDSTEM Conference, Liverpool, UK, 2009; Kelley et al. A population of selected renal cells augments renal function and extends survival in the ZSF-1 model of progressive diabetic nephropathy. *Cell Transplant.* 2013; 22:1023-39; Kelley et al. Intra-renal transplantation of bioactive renal cells preserves renal functions and extends survival in the ZSF-I model of progressive diabetic nephropathy. ADA Conference, San Diego, CA, 2011; Kelley et al. Bioactive renal cells augment kidney function in a rodent model of chronic kidney disease. ISCT Conference, Philadelphia, PA, 2010; Kelley et al. Enhanced renal cell function in dynamic 3D culture system. KIDSTEM Conference, Liverpool, UK, 2008; Kelley et al. Bioactive renal cells augment renal function in the ZSF-1 model of diabetic nephropathy. TERMIS Conference, Orlando, FL, 2010; Presnell et al. Isolation, characterization, and expansion (ice) methods for defined primary renal cell populations from rodent, canine, and human normal and diseased kidneys. *Tissue Engineering Part C Methods.* 2010; 17:261-73; Presnell et al. Isolation and characterization of bioresponsive renal cells from human and large mammal with chronic renal failure. Experimental Biology Meeting, New Orleans, LA, 2009; Wallace et al. Quantitative ex vivo characterization of human renal cell population dynamics via high-content image-based analysis (hca). ISCT Conference, Philadelphia, PA, 2010; Yamaleyeva et al. Primary human kidney cell cultures containing erythropoietin-producing cells improve renal injury. TERMIS Conference, Orlando, FL, 2010) Therapeutic intervention with NKA is intended to improve renal function in subjects with CKD and T2DM and delay the need for renal dialysis or transplantation which, based on the current standard-of-care, is inevitable for ESRD.

NKA is made from expanded autologous selected renal cells (SRC) obtained from each individual subject's kidney biopsy. To manufacture NKA, kidney biopsy tissue from each enrolled subject will be processed to have renal cells expanded and SRC selected. SRC will be formulated in a gelatin based hydrogel at a concentration of $100 \times 10^6$ cells/mL, packaged in a 10 mL syringe, and shipped to the clinical site for use.

Treatment Regimen

Therapeutic Dose Selection

The appropriate cell implantation dosage in humans can be determined from existing information relating to either the activity of the cells or extrapolated from dosing studies conducted in preclinical studies. Multiple animal studies conducted using a wide range of doses (3-15 million cells per gram of kidney tissue injected), and extended periods of time post-treatment (up to one year) have demonstrated the ability of NKA to positively affect renal outcomes in different models of renal insufficiency and disease. From in vitro culture and in vivo animal experiments, the amount of cells can be quantified and used in calculating an appropriate dosage of implanted material. Additionally, the patient can be monitored to determine if additional implantation can be made or implanted material reduced accordingly.

In one embodiment, NKA is presented in a sterile, single-use syringe. The final volume is calculated from the concentration of $100 \times 10^6$ SRC/mL of NKA and the target dose of $3.0 \times 10^6$ SRC/g kidney weight (estimated by MRI). As described in the literature, volume measurements of the kidney in mLs obtained by different methods are approximately 92-97% of dry weight measurements in grams obtained by measuring isolated organs trimmed of perirenal fat. Therefore, as a conservative estimation, doses of NKA will be calculated using a conversion of 1 g equals 1 mL. Using this ratio represents the safest approach as it guarantees patients will not receive doses higher than corresponding doses in animal studies. Dosage will be determined by the surgeon at the time of injection based on the patient's kidney weight. The maximum volume for any patient will be 8.0 mL; that is, if any subject has a left kidney with a calculated weight ≥259 g, then that subject will receive 8 mL of NKA.

Number of Treatments

Expanded renal cells can be cryopreserved during cell expansion to accommodate for patient-dependent variation in cell expansion. Cryopreserved renal cells provide a continuing source of cells to manufacture multiple doses of the bioactive cell formulation for re-injection and in the event that another treatment is needed (e.g., delay due to patient sickness, unforeseen process events, etc.).

In one embodiment, the BRC or SRC are administered as a single treatment into one kidney. In another embodiment, the BRC or SRC are administered as a single treatment with injections into both kidneys. In another embodiment, the BRC or SRC are administered as repeated or multiple injections into one or both kidneys. In yet another embodiment, the first and second injections are administered at least 3 months apart, at least 6 months apart, or at least one year apart. In still yet another embodiment, the BRC or SRC are administered over more than 2 injections.

The following examples are offered for illustrative purposes only, and are not intended to limit the scope of the present invention in any way.

EXAMPLES

Example 1—Phase I, Open-Label Safety and Delivery Optimization Study of an Autologous Neo-Kidney Augment (NKA) in Patients with Chronic Kidney Disease (TNG-CL010)

A first-in-human (FIH) clinical trial was initiated at the Karolinska University Hospital Huddinge in Stockholm, Sweden and the University of North Carolina. The trial was a Phase 1, open-label, safety and injection optimization study of NKA injected into patients with CKD. NKA was manufactured from SRC obtained from a patient's biopsy, formulated with gelatin biomaterial, and injected back into the patient's left kidney. The primary objective of the study was to assess the safety and optimal injection of NKA injected at one site in a recipient kidney as measured by procedure and/or product related adverse events (AEs) through 12 months post-injection. The secondary objective of the study was to assess changes in renal function over a 12 month period following injection as measured by laboratory assessments. Each patient's baseline rate of disease progression was used as the control to monitor for adverse changes in the rate of disease progression following injection.

Materials and Methods Treatment Protocol
Patients

Seven adult type-2 diabetic CKD stage 3-4 patients at the Department of Renal Medicine, Karolinska University Hospital, Stockholm, Sweden (n=6) and Department of Renal Medicine, University of North Carolina at Chapel Hill, USA (n=1) were recruited for the study. The study was approved by the regional committees of ethics in Stockholm and Chapel Hill and adhered to the statutes of the Declaration of Helsinki. All patients provided written consent of participation.

In brief, adult (age 53-70 years) type-2 diabetic patients with GFR of 15-50 ml/min and clinical course compatible with diabetic nephropathy, ongoing ACEi/ARB treatment and a kidney size >10 cm (cortical thickness >5 mm) were eligible for inclusion. Patients who satisfied the eligibility criteria and signed informed consent entered a screening phase including full physical examination, electrocardiograms and laboratory assessments (hematology, serum chemistry and urinalysis). In addition, an MRI was performed to assess kidney volume and cortex thickness. Renal scintigraphy was performed to assess split kidney function. Eligible patients underwent a kidney biopsy according to the standard clinical procedure (two cores) to obtain the cells for implantation. The study protocol is depicted in FIG. 1.

Preparation of Neo-Kidney Augment (NKA)

Briefly, biopsies were dissociated enzymatically in a buffer containing 4.0 units/mL dispase (Stem Cell Technologies, Inc., Vancouver, BC, Canada) and 300 units/mL collagenase IV (Worthington Biochemical, Lakewood, NJ, USA). Red blood cells and debris were removed by centrifugation through 15% iodixanol (Optiprep®, Axis Shield, Norton, MA, USA). Primary renal cells were seeded onto tissue culture treated polystyrene plates (NUNC, Rochester, NY, USA) and cultured in 50:50 media, a 1:1 mixture of high glucose Dulbecco's Modified Eagle Medium (DMEM)+Keratinocyte Serum Free Medium (KSFM) containing 5% Fetal Bovine Serum (FBS), 1×ITS (insulin/transferrin/sodium selenite medium supplement), and antibiotic/antimycotic (all from Invitrogen, Carlsbad, CA, USA). Prior to post-culture cell separation, primary renal cell cultures were transferred from atmospheric oxygen conditions (21%) to a more physiologically relevant low-oxygen (2%) environment for 24 hours, to improve cell separation efficiency. Separation of primary renal cell cultures, prepared as 75×106 cells in 2 mL unsupplemented KSFM (uKSFM), was performed by centrifugation through a four-step iodixanol (OptiPrep; 60% w/v in uKSFM) density gradient layered specifically for rodent (16%, 13%, 11%, and 7%) in 15 mL conical polypropylene tubes and centrifuged at 800 g for 20 min at room temperature. After centrifugation all bands were washed 3 times with sterile phosphate buffered saline (PBS) prior to use.

Combining bioactive renal cells that exhibit a buoyant density greater than approximately 1.0419 g/mL from the density gradient centrifugation step, produced therapeutically bioactive SRCs. The preparation of selected renal cells from patient biopsies is also described, for example, in Kelley et al. (Am J Physiol Renal Physiol 2010; 299: F1026-39), Kelley et al. (Cell Transplant 2013; 22:1023-39), Bruce et al. (Methods Mol Biol. 2013; 1001:53-64) and Basu et al. (Cell Transplant. 2011; 20:1171-901). Cell suspensions (100 □L) were loaded into a 10 cc syringe mixed with gelatin-based hydrogel biomaterial to formulate the NKA product.

Cell viability is measured at each culture passage and during NKA formulation (Trypan Blue Exclusion). Assays of cell phenotype and potency are performed on the final NKA product as previously described (Basu and Ludlow. Regen Med 2014; 9:497-512). All procedures are conducted in compliance with current Good Manufacturing Practices (cGMP) under the guidance of FDA and MPA QP.

Implantation Procedure

In the Swedish cases (patient #1-6) a Pfannenstiel incision was made and a hand-assist device placed in the wound (Gelport©, Applied Medical Resources Corporation). Moving the peritoneum medially by blunt manual dissection created a retroperitoneal space (Wadström J. Transplantation. 2005; 80:1060-8). The medio-anterior portion of Gerota's fascia of the left kidney was opened to expose the peri-renal fatty tissue, which was abundant in all cases. The fatty tissue was removed to expose the kidney capsule, essentially all of the medial and lateral aspects as well as almost the entire convex/lateral part of the kidney. The extensive dissection allowed to position the kidney in alignment with the injecting needle and to visualize if there was any penetration or leakage of the injected material. From the left iliac fossa a guiding cannula was inserted transcutaneously to puncture the kidney capsule at the lower pole. An 18 G needle was thereafter inserted through the guiding cannula into the renal cortex along the convex longitudinal axis of the kidney. Two mL of NKA was deposited at 4, 3, 2 and 1 cm from the puncture of the capsule over a 10-15 minute time period (total 8 mL). The needle was kept in place 5 minutes to promote haemostasis. No per-operative bleeding and only minimal amounts of NKA (<1 mL) was seen backing out of the puncture hole in any of the procedures. The wound was not drained and the abdominal wall was closed with a running suture. The US patient (#7)

underwent robot-assisted laparoscopic renal cell implantation in the left renal cortex. Dosing of NKA was determined by estimated kidney weight (the maximum volume for any patient was 8 mL, which all subjects received).

MR Imaging

MRI was performed before implantation (<30 days) and 3 and 6 months after using a 1.5-T MR unit (Siemens Magnetom Aera, Siemens AEG, Erlangen, Germany). Cortical thickness was measured in the dorsal part of the upper pole of the kidney using a 4 mm thick axial T2Haste image. Kidney volume was quantified by manual segmentation using a dataset of breath hold 2.5 mm thick VIBE images obtained without fat saturation.

Renal Scintigraphy

Kidney function was evaluated in the supine position 3 hours after intravenous injection of 50 MBq $^{99m}$Tc-DMSA (CIS bio international, Gif sur Yvette Cedex, France). An anterior and posterior acquisition with a preset time of 20 minutes using a double headed gamma camera (Symbia T16 SPECT/CT, Siemens, Erlangen, Germany) equipped with low-energy high-resolution collimator, 256×256 matrix. Differential renal function was assessed using region-of-interest drawings including entire kidney with a geometrical mean calculated from both projections.

Biochemical and Other Analyses

Analyses of high-sensitivity C-reactive protein (hsCRP), creatinine, cystatin C, iohexol clearance, haemoglobin, albumin, Ca, $PO_4$, and albumin-creatinine ratio (ACR) were performed with validated routine methods at the certified Clinical Laboratory of Karolinska University Hospital, Stockholm, Sweden and Chapel Hill, North Carolina, USA.

Statistical Analyses

Data are expressed as mean±SEM. Statistical significance was set at the level of p <0.05.

Results

Estimated Glomerular Filtration Rate (eGFR)

The cohort of patients injected with NKA underwent a pre-injection assessment of the progress of their kidney disease and were consistent with a Hemmelgarn Moderate Group decline in eGFR of 5-10 ml/min/1.73 m³ (see e.g. Hemmelgarn et al, Kid Intern; 2006, which shows the division of community-dwelling elderly patients in 5 groups based on the rate of change in mean eGFR).

Figure 2:
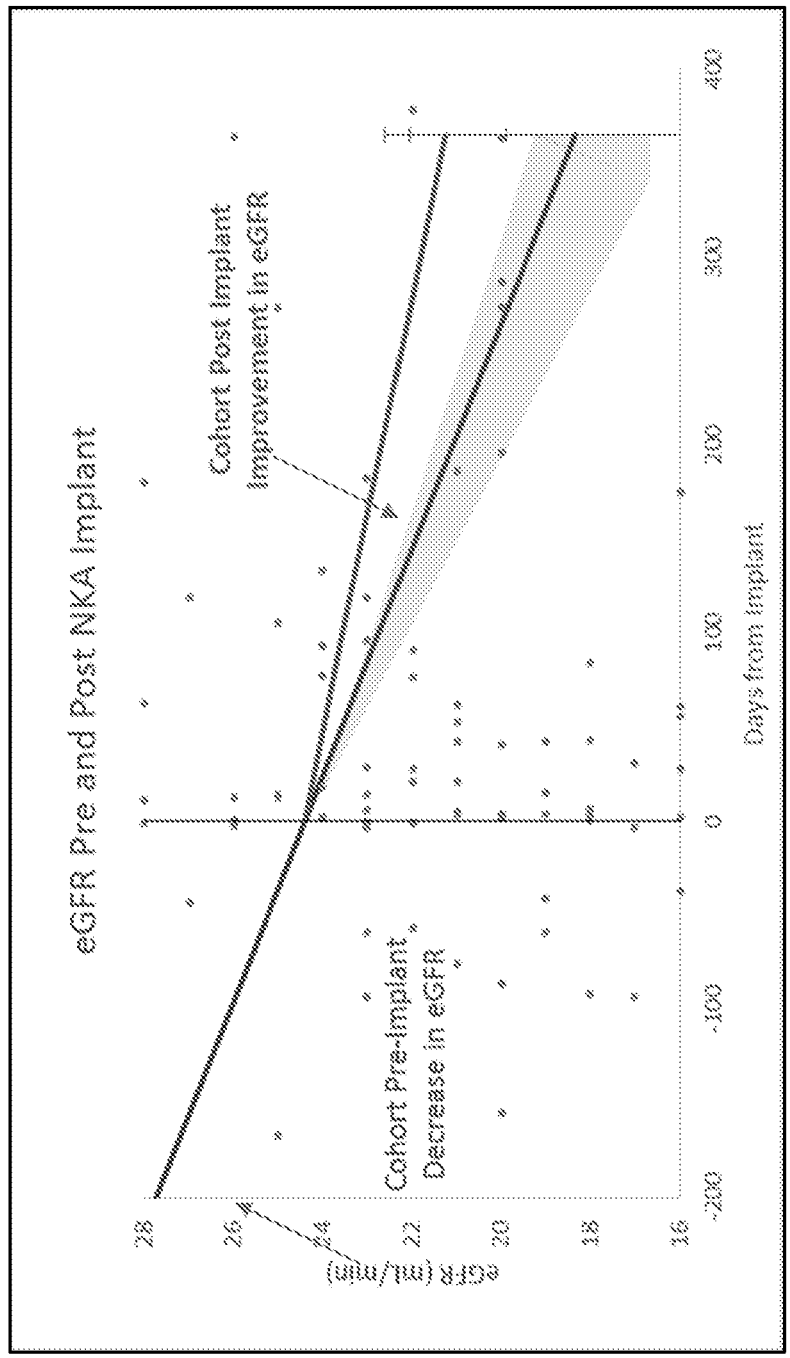
FIG. 2 depicts the estimated glomerular filtration rate pre- and post-NKA injection of the entire cohort.
Figure 3B:
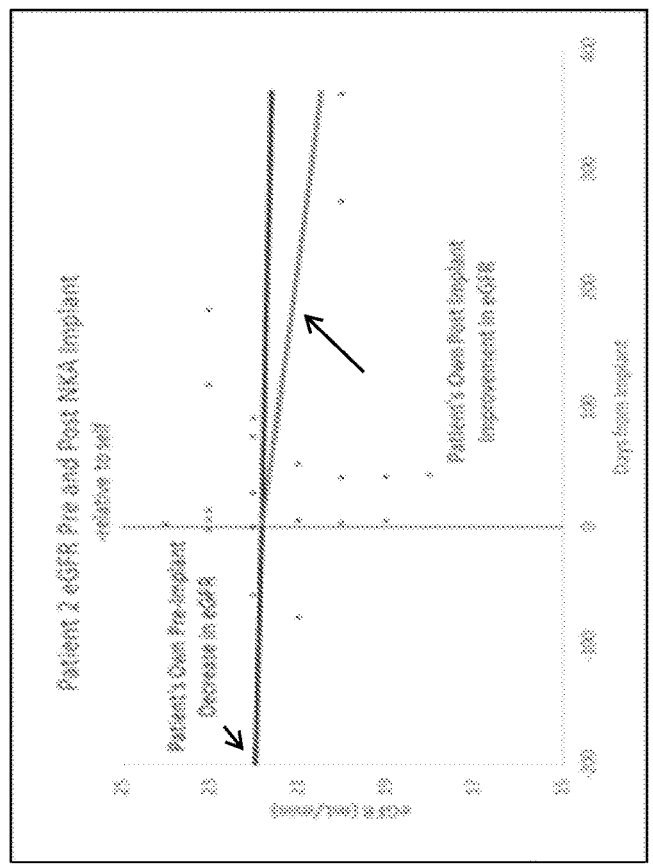
FIGS. 3A-3G shows individual changes in the estimated glomerular filtration rate.
Figure 3A:
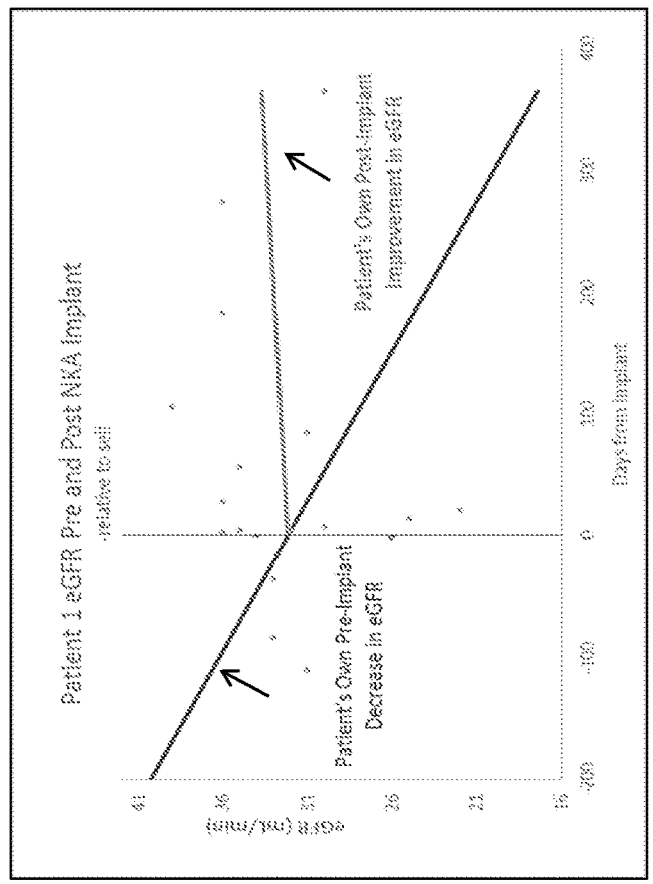
Figure 3D:
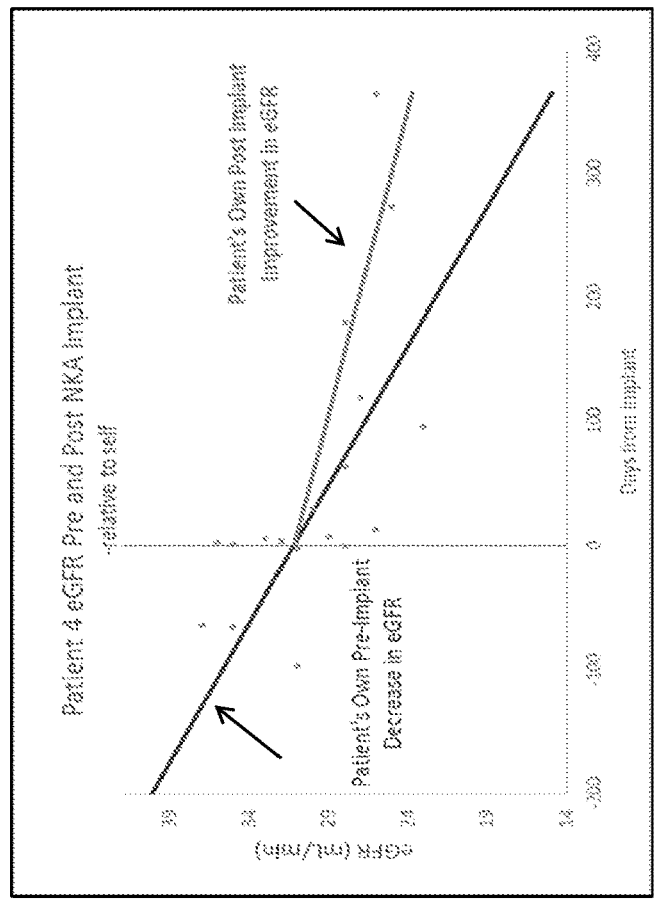
Figure 3C:
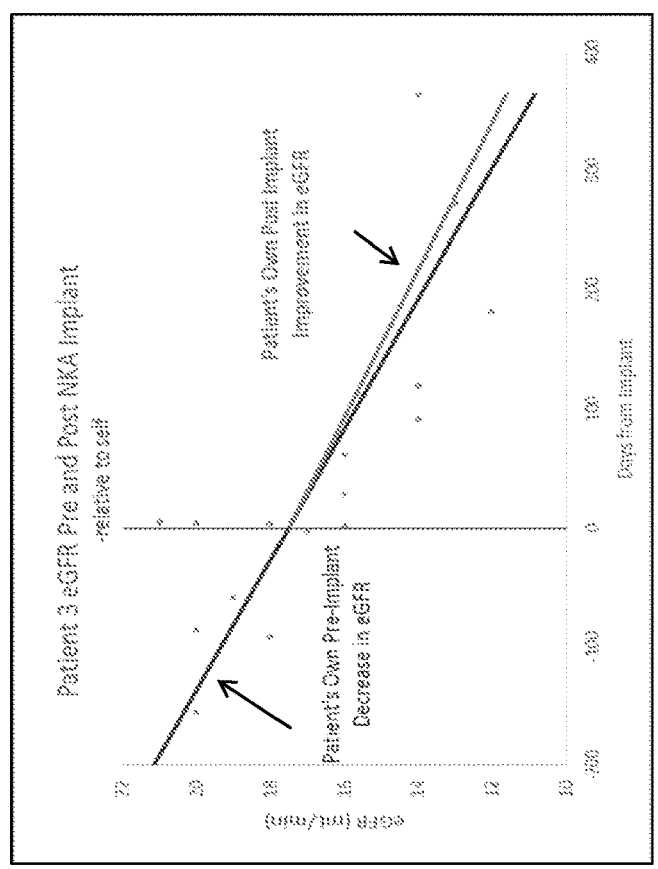
Figure 3F:
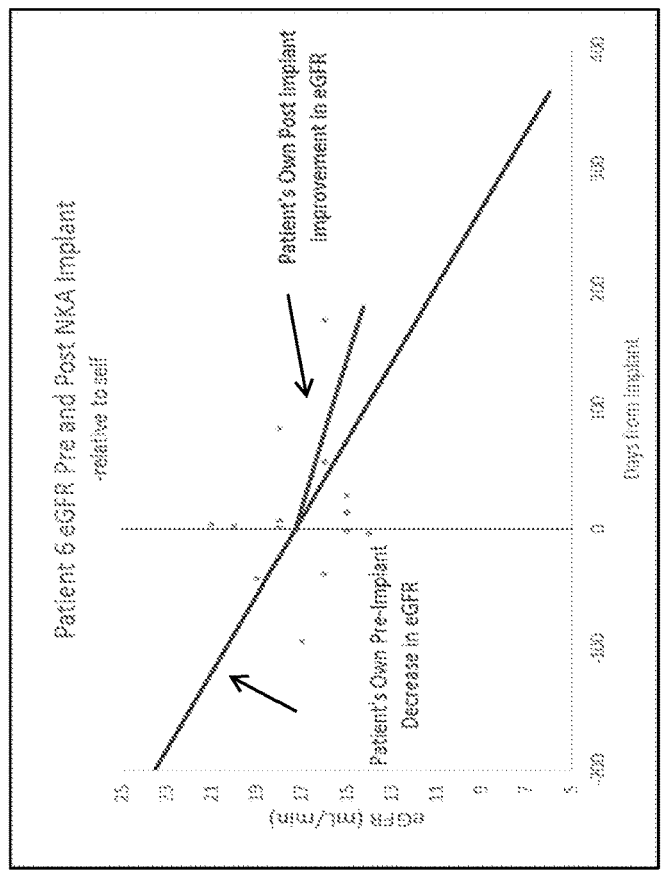
Figure 3E:
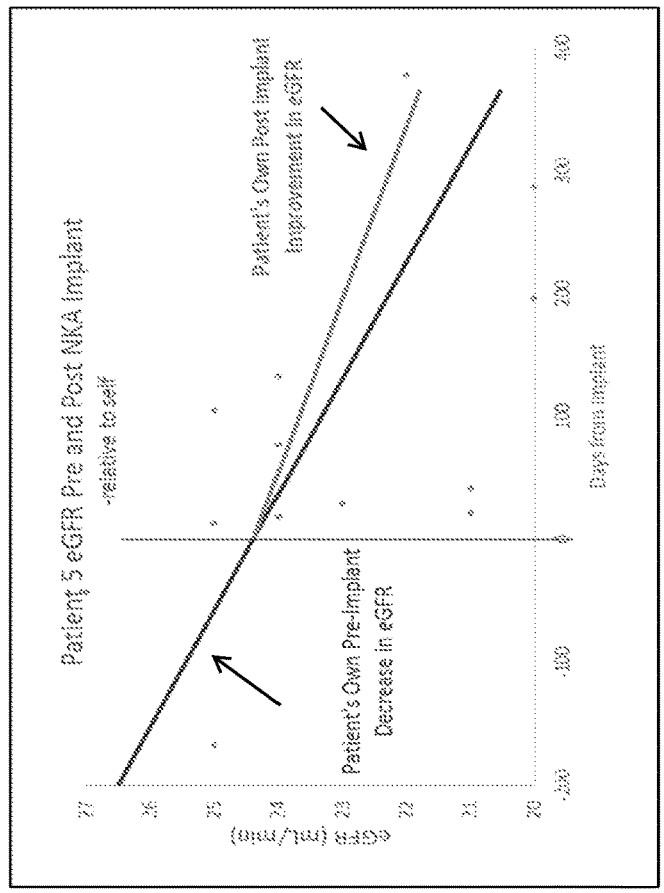
Figure 3G:
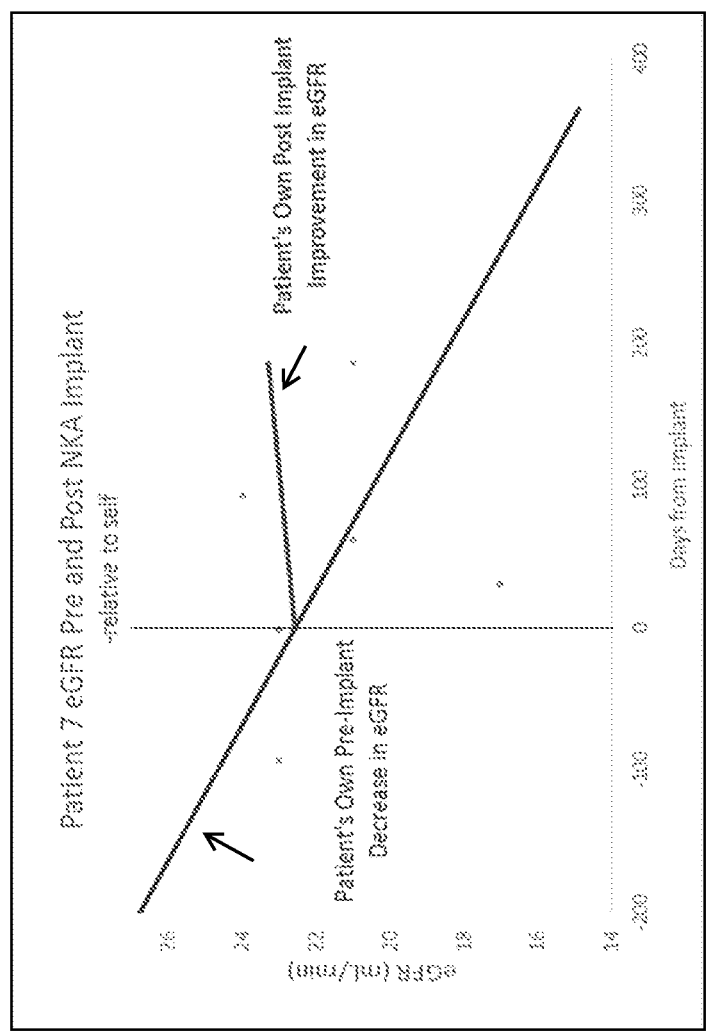

Pre-injection information from this patient cohort indicated that their average decline in eGFR was 6.1 ml/min/year (FIG. 2). Post NKA administration, eGFR decline for the combined group of 7 patients (6 patients from the Swedish study and 1 patient from the American study) was −3.1 ml/min/year (FIG. 2). The average post-injection rate-of-decline for eGFR in the cohort is shown by the green line and the shaded blue area represents the range of eGFR for the Hemmelgarn group of community-dwelling elderly patients with moderately severe CKD 3b/4 with an annual decline of 5-10 ml/min/year (shaded area in FIG. 2).

The eGFR changes for individual patients' post-injection of NKA along with the patient's individual pre-injection decline demonstrated that 6 of 7 patients had a reduction in the rate of decline in eGFR over the period patients were on study (FIG. 3). The annual rate of eGFR decline pre and post injection for each patient is shown in the Table 2.

TABLE 2

Change in Estimated Glomerular Filtration Rate by Patient

| Patient # | Change in eGFR (mL/min/year) | |
|---|---|---|
| | Pre-NKA | Post-NKA |
| Patient 1 | −14.8 | 1.5 |
| Patient 2 | −0.2 | −1.3 |
| Patient 3 | −6.7 | −5.9 |
| Patient 4 | −16.3 | −7.5 |
| Patient 5 | −3.9 | −2.6 |
| Patient 6 | −11.4 | −5.9 |
| Patient 7 | −7.7 | 1.4 |

In summary, 6 of the 7 patients had a reduction in the rate (slope) of eGFR decline after NKA injection. The pre-injection rate-of-decline in eGFR for the NKA cohort was 6.1 ml/min/year, consistent with Hemmelgarn's study of community-dwelling elderly patients.

Figure 4:
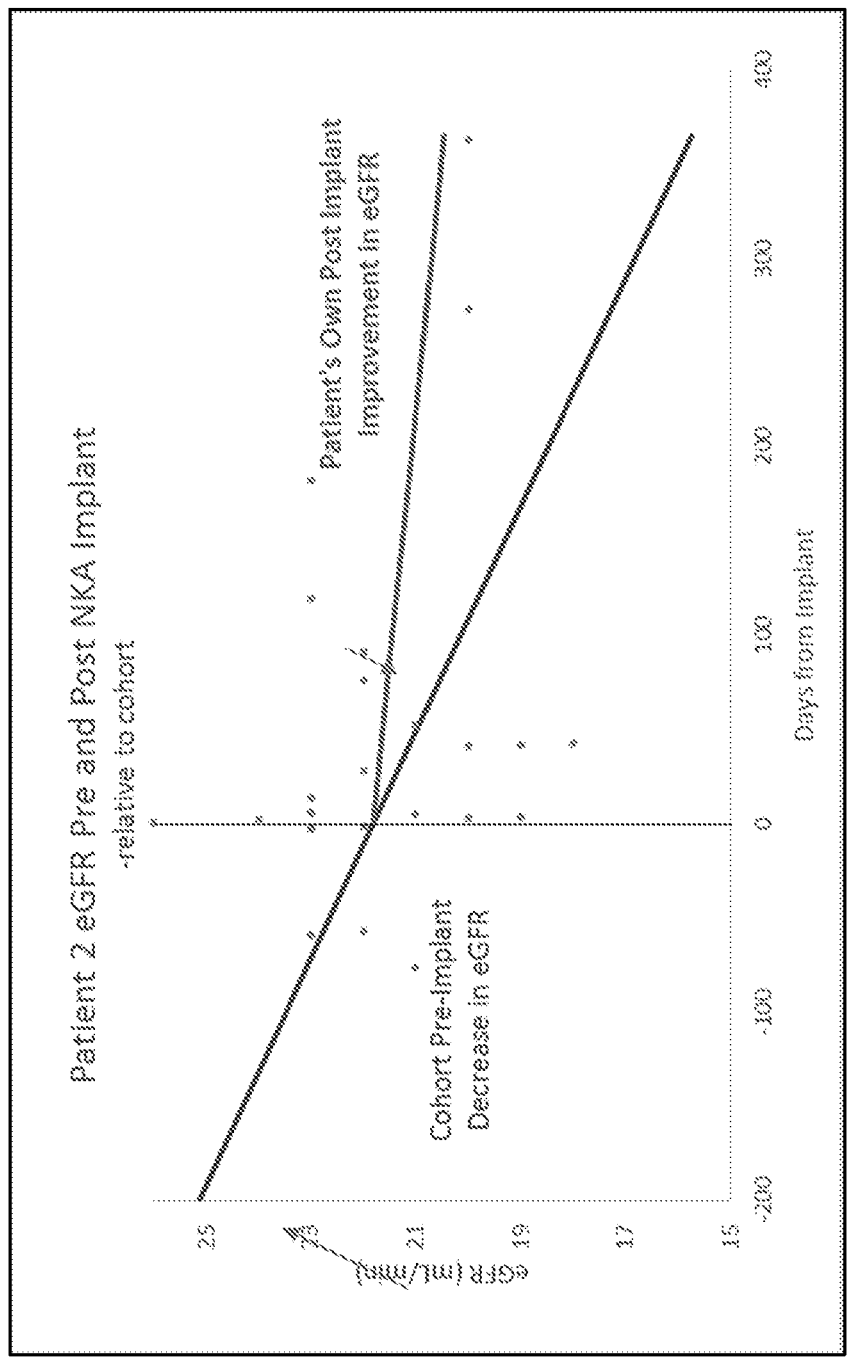
FIG. 4 depicts the estimated glomerular filtration rate pre- and post-NKA injection of patient #2.

Patient #2 continued at approximately the same rate of decline as observed during the pre-injection period. Over the short period of eGFR sampling prior to NKA injection in this patient, his eGFR measurements varied over a range of ±3 ml/min/1.73 m3. When this patient's eGFR was compared to the overall cohort of 7 patients, changes in his eGFR followed a similar pattern for post-injection as others in the study cohort (FIG. 4). Additionally, this patient's serum creatinine increase was attenuated suggesting a potential stabilization of progression for CKD (see section on sCr below).

Figure 5:
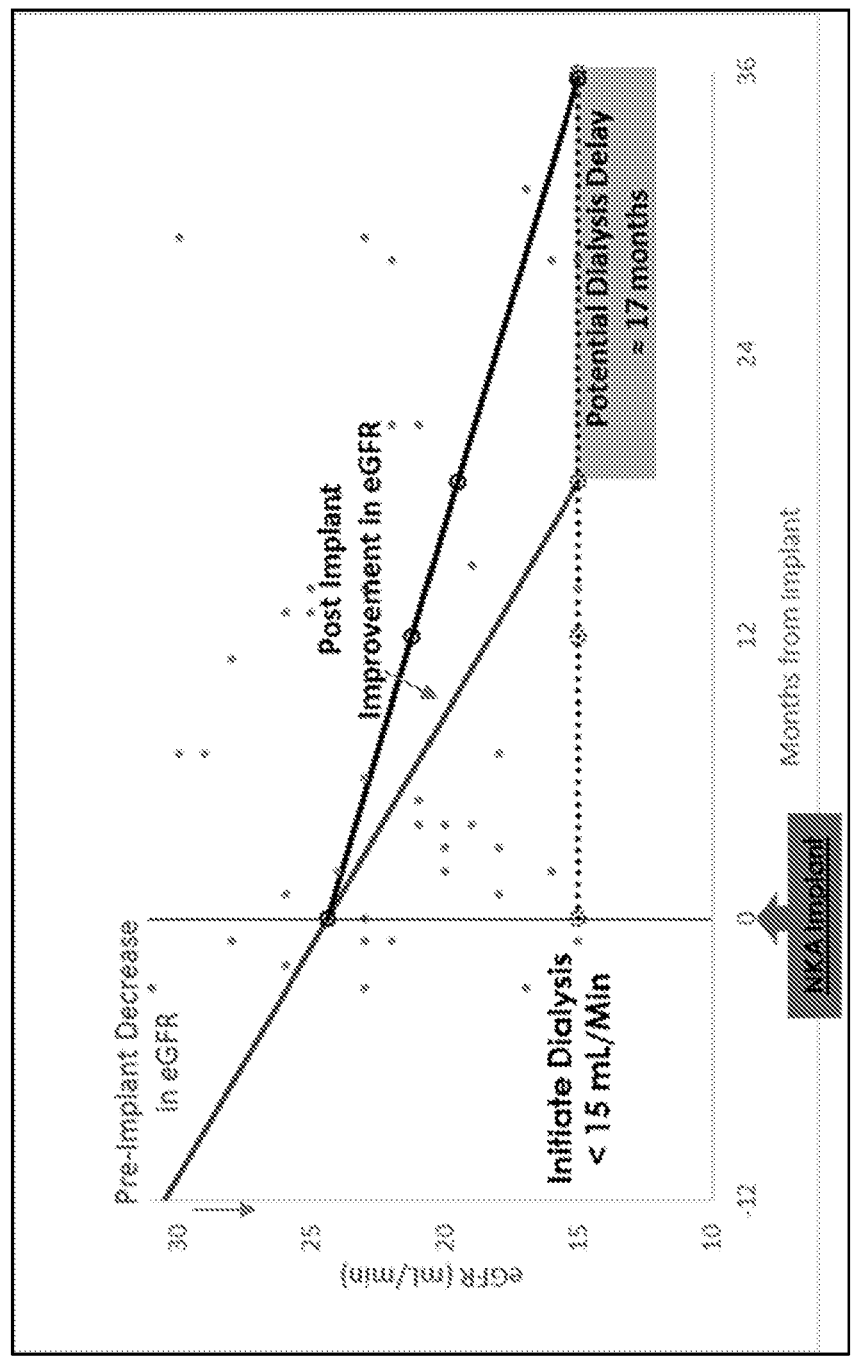
FIG. 5 depicts the rate of decline of renal function pre- and post-NKA injection with imputed delay in dialysis.

The Phase I Clinical Trials with NKA were conducted using doses of NKA that were considered likely to be sub-therapeutic, to evaluate the effects of NKA when injected into a single kidney in a small cohort of elderly diabetic pre-dialysis patients with CKD 3b/4. In a diabetic animal model of aggressive chronic kidney disease, the optimal outcomes of delaying death from end-stage kidney disease were obtained when animals were treated in both kidneys. In the interest of safety, in the first clinical studies of NKA, only 1 kidney was injected with NKA, and therefore a therapeutic signal was not necessarily expected. However, after monitoring the progress of CKD in this cohort of patients for ~1 year, the decline in renal function projected for this cohort was modified by a single injection of NKA into a single kidney (left). When the rates of decline of renal function pre- and post-injection are compared, the NKA injected patients have an imputed delay in dialysis of over 1.5 years (FIG. 5).

Serum Creatinine (sCr)

Figure 6:
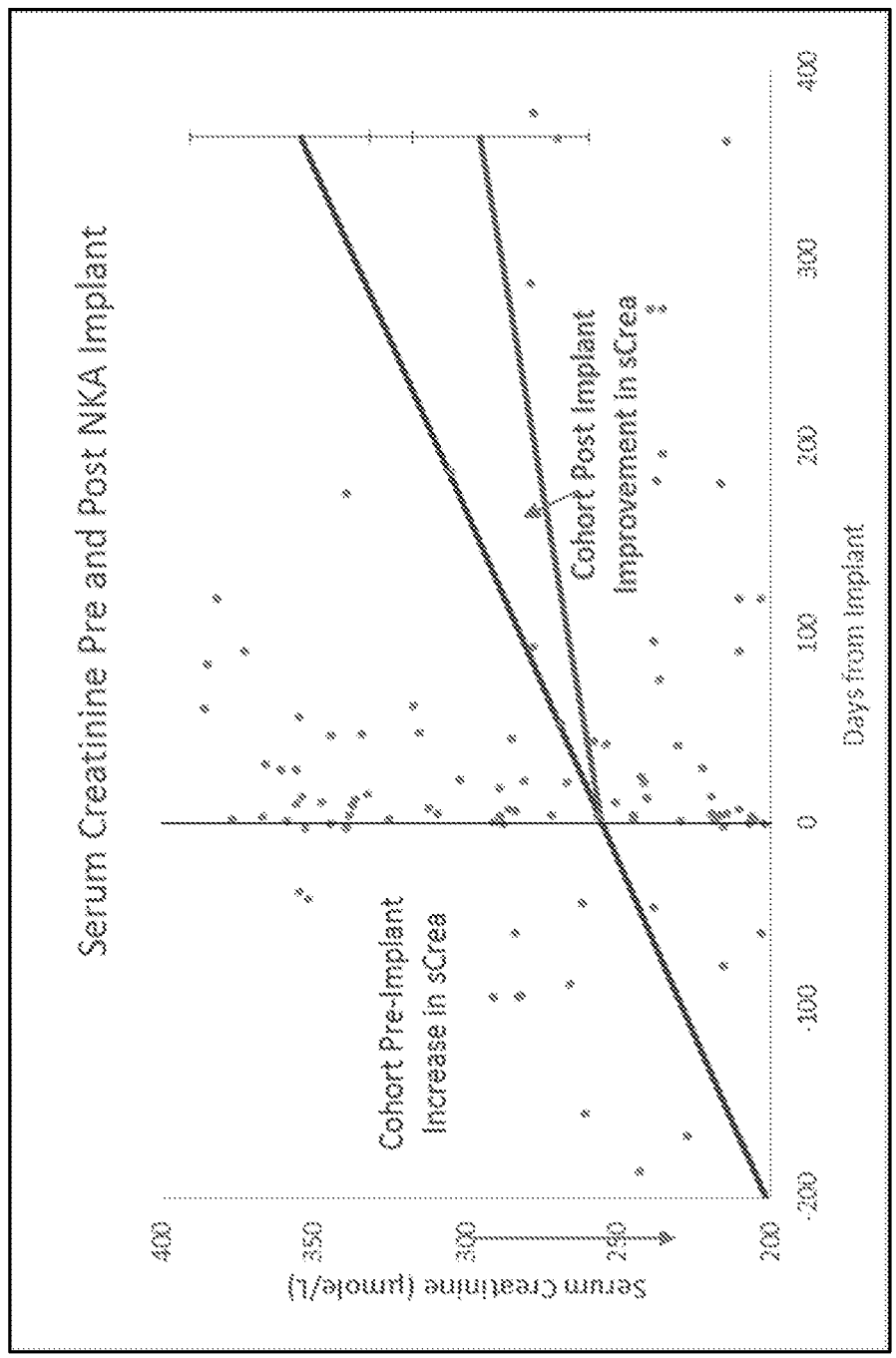
FIG. 6 depicts serum creatinine pre- and post-NKA injection of the entire cohort.
Figure 7B:
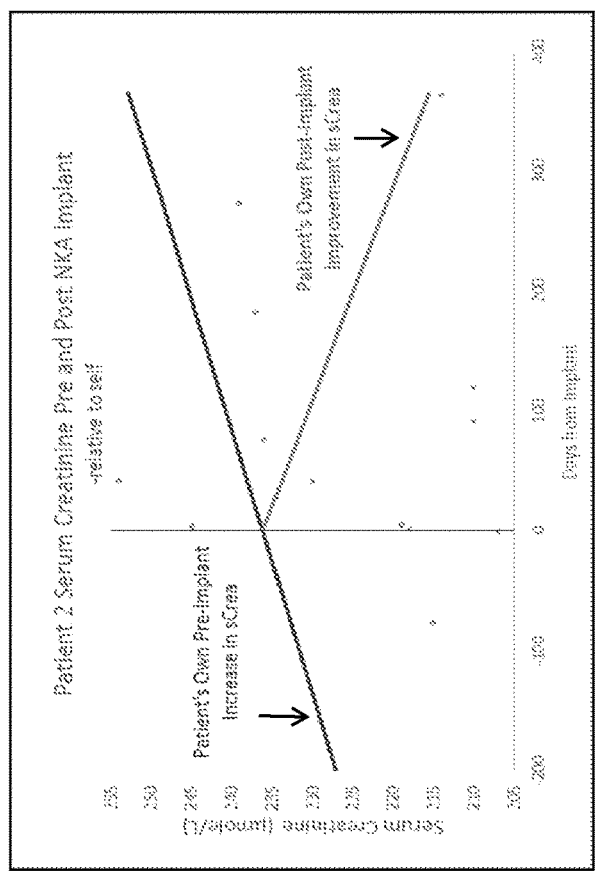
FIGS. 7A-7G shows individual changes in serum creatinine pre- and post-NKA injection
Figure 7A:
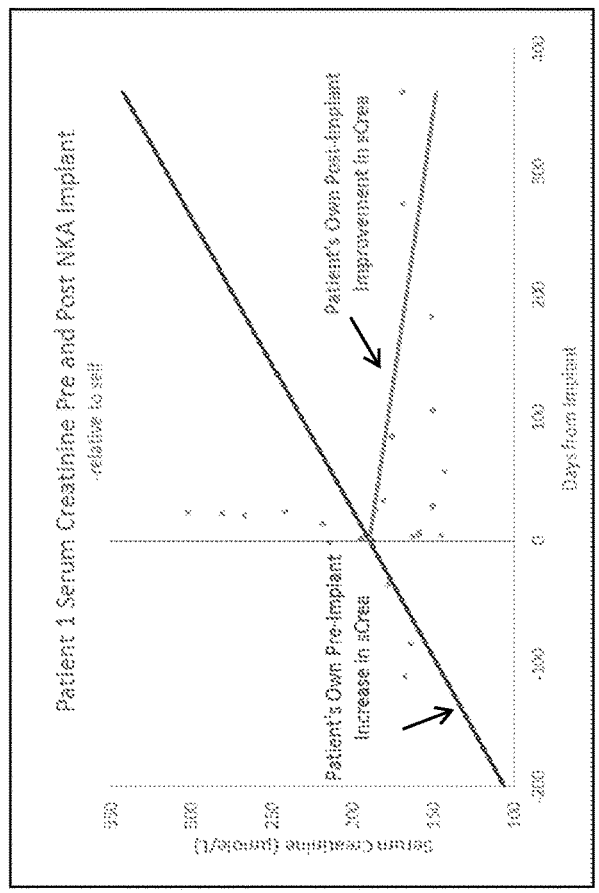
Figures 7C, 7D:
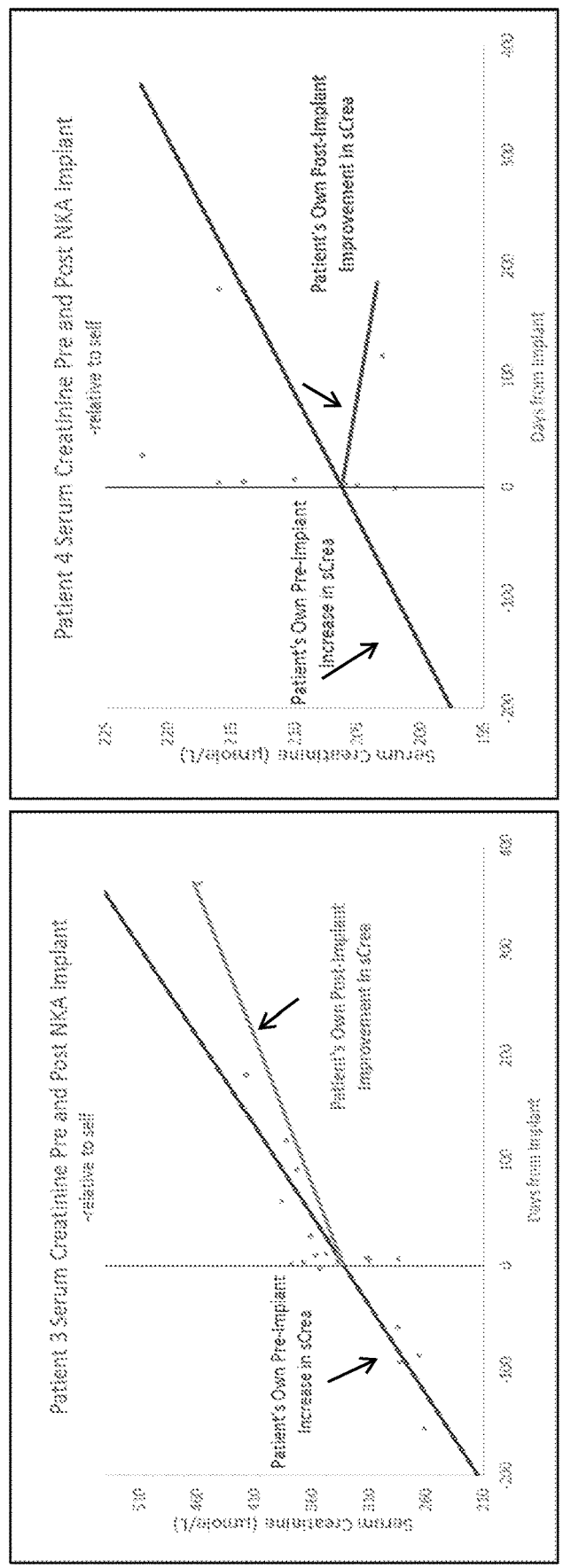
Figure 7F:
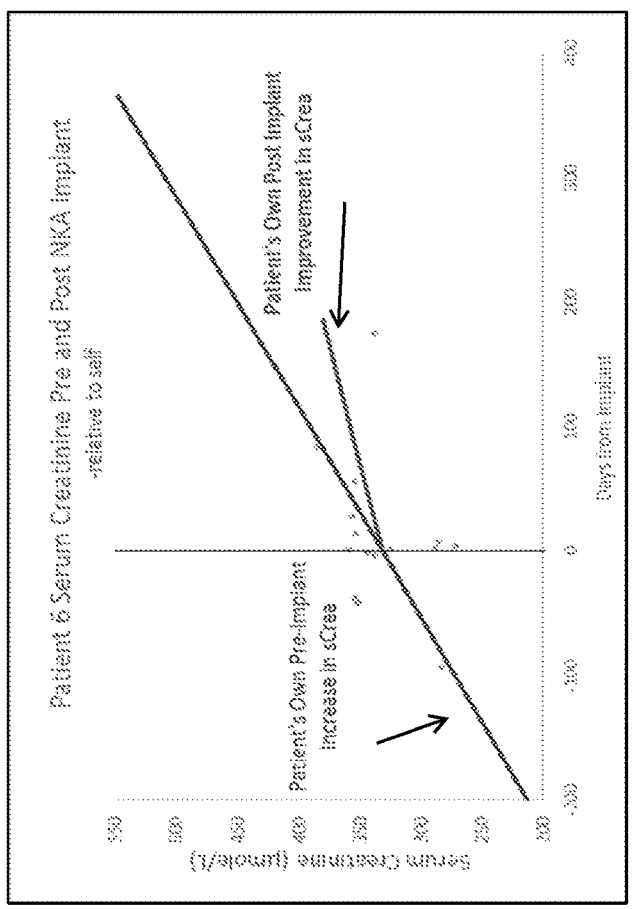
Figure 7E:
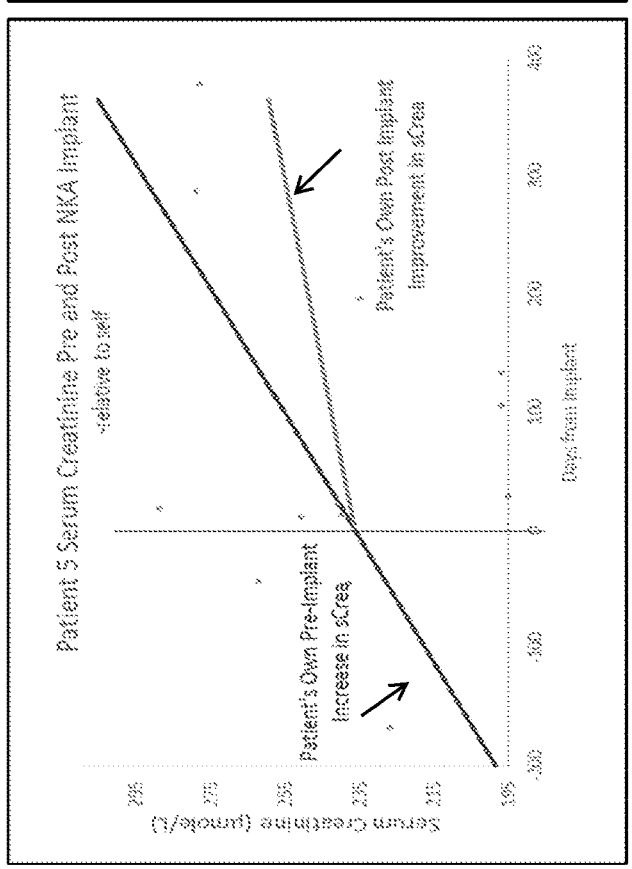
Figure 7G:
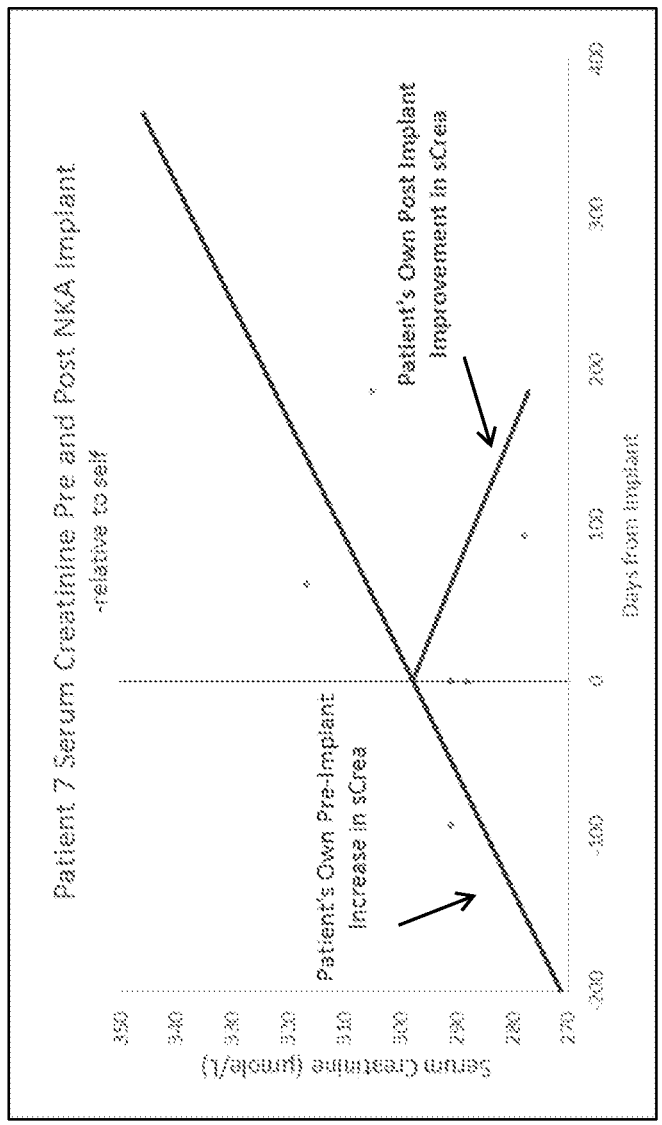

Serum creatinine levels for the cohort of patients pre-injection showed a general increase consistent with what would be expected in diabetic patients with moderate CKD (red-line). The overall pre-injection increase in sCr for the cohort of patients was >100 μmole/L/yr. Post-injection the cohort of patients had an increase <50 μmole/L/yr (green line). The overall trends in SCr before and after injection are shown in FIG. 6. Individual patient serum creatinine changes, post-injection of NKA (green) along with the patient's individual pre-injection decline are shown in FIG. 7. The annual rates of increase of serum creatinine before and after NKA injection for each patient are shown in Table 3.

TABLE 3

Change in Serum Creatinine by Patient

| PT # | Change in sCr (μmole/L/year) | |
|---|---|---|
| | Pre-NKA | Post-NKA |
| Patient 1 | 153 | −41 |
| Patient 2 | 17 | −21 |
| Patient 3 | 214 | 200 |
| Patient 4 | 16 | −39 |
| Patient 5 | 69 | 23 |
| Patient 6 | 216 | 95 |
| Patient 7 | 48 | −40 |

In summary, after NKA injection, all patients had a reduction in their individual rate of increase for sCr compared to the rate of sCr increase that had been observed in the pre-injection period. This change was consistent for each patient and supports the effects observed for eGFR in the after NKA injection period.

Example 2—Phase II, Open-Label Safety and Efficacy Study of an Autologous Neo-Kidney Augment (NKA) in Patients with Type 2 Diabetes and Chronic Kidney Disease (RMCL-001)

Therapeutic Product

NKA is made from expanded autologous selected renal cell population (SRC) obtained from the patient's kidney biopsy as described in Example 1. To manufacture NKA, kidney biopsy tissue from each enrolled patient were processed to have renal cells expanded and SRC selected. SRC will be formulated in a gelatin based hydrogel at a concentration of $100 \times 10^6$ cells/mL, packaged in a 10 mL syringe, and shipped to the clinical site for use (see example 1).

Study Objectives

Primary Objective: The primary objective of the study is to assess the safety and efficacy of NKA injected in one recipient kidney and determine if two injections of NKA provide stabilization of renal function.

Primary Safety Outcome Measures: procedure and/or product related adverse events (AE's) through 12 months following the initial NKA injection.

Primary Efficacy Outcome Measures: serial measurement of serum creatinine and estimation of GFR through 6 months following the second cell injection Secondary Objective: The secondary objective of the study is to assess the safety and tolerability of NKA administration by assessing renal-specific adverse events over a 12 month period following a patient's first NKA injection.

Secondary Safety and Tolerability Outcome Measures: renal-specific laboratory assessments through 12 months following the last NKA injection under this protocol, whether first or second.

Exploratory Objective: Exploratory objectives of the study are designed to assess the impact of NKA on renal function over a 12 month period following the initial NKA injection.

Exploratory Outcome Measures: clinical diagnostic and laboratory assessments of renal structure and function (including eGFR, serum creatinine, and proteinuria) to assess changes in the rate of progression of renal disease; and effect of method of injection on these parameters.

Exploratory quality of life outcome measure will be the Kidney Disease Quality of Life survey obtained at baseline and at 1, 3, 6, 7, 9, 12, 15, 18, 30, and 42 months after a patient's first NKA injection.

Study Design

Multi-center, prospective, open-label, single-group study. All enrolled subjects will be treated with up to two injections of NKA at least 6 months apart.

Randomization

Open-label, non-randomized.

Control Group

Each subject will serve as his or her own control; the patient's previous medical history, which must include a minimum 6 month period of observation of renal function, will serve as the comparator for rate of progression of renal insufficiency.

Sample Size

Up to 30 subjects will be injected with NKA. As this is a Phase II safety and efficacy study, robust statistical analysis will not be performed. Therefore, the sample size proposed for this study is a size typical for the active treatment group in Phase II studies, allowing for identification of safety outcomes and early efficacy in a limited population.

Study Population

Male or female patients 30 to 70 years of age with Type 2 diabetes mellitus and CKD with eGFR between 20 and 50 mL/min/1.73 m². An enrolled patient should have sufficient historical clinical data to determine his or her individual rate of CKD disease progression.

Inclusion Criteria: Unless otherwise noted, inclusion criteria must be met at Screening and prior to injection.

1. Male and female subjects, age 30 to 70 years on the date of informed consent.
2. Patients with type 2 diabetes mellitus (T2DM).
3. Patients with a well-established diagnosis of diabetic nephropathy as the underlying cause of their renal disease.
4. At screening, patients not previously injected with NKA with CKD defined as a GFR of 20-50 mL/min/1.73 m² inclusive. Patients previously treated with a single NKA injection with eGFR 15 to 60 mL/min may also enroll in this clinical trial.
5. Microalbuminuria that cannot be explained by an alternative diagnosis. Microalbuminuria is defined as urinary albumin-creatinine ratio (UACR) ≥30 mg/g or urine albumin excretion ≥30 mg/day on 24 hour urine collection.
6. Prior to biopsy, systolic blood pressure between 105 and 140 mmHg (inclusive) and diastolic blood pressure ≤90 mmHg.
7. Ongoing and stable treatment with ACEI or ARB initiated at least 8 weeks prior to enrollment. Treatment must be stable for the 6 weeks immediately prior to injection. Stable treatment is defined as dose adjustment to no less than ½ of the current dosage and no more than 2× the current dosage over the 6 week period immediately prior to injection; dose interruptions of up to 7 days due to medical necessity are allowed. Patients who are intolerant to ACEI or ARBs may be included as long as they have stable BP within the acceptable limits.
8. Minimum of 2 measurements of eGFR or sCr taken at least 3 months apart (prior to screening) and within the previous 12 months to define the rate of progression of CKD. The patient should have sufficient historical data to provide a reasonable estimate of the rate of progression of CKD as determined following consultation with the Medical Monitor (to insure sufficient data is available). In addition, the rate of progression of CKD must be consistent over time. There is no defined rate of progression that is required to qualify for inclusion.
9. Willing and able to refrain from use of NSAIDs (including aspirin) and clopidogrel, prasugrel, or other platelet inhibitors peri-procedure (i.e., before and after both the biopsy and injection). The wash-out period before and after each procedure should be 7 days. Willing and able to refrain from use of fish oil and dipryridamole for 7 days before and 7 days after each procedure.
10. Willing and able to cooperate with all aspects of the study.
11. Willing and able to give signed informed consent.

Exclusion Criteria: Patients may not be enrolled if they meet any of the exclusion criteria listed below. Criteria should be assessed at Screening and before injection unless noted otherwise.
1. Type 1 diabetes mellitus (DM).
2. History of a renal transplant.
3. HbA1c >10% at Screening. Patients with HbA1c >8% at the time of screening should be offered diabetic teaching and advised to consult their primary physicians for further diabetic management.
4. Hemoglobin levels <9 g/dL prior to injection. Hemoglobin levels should be measured within 48 hours before the procedure or per site standard practice.
5. Known allergy to kanamycin or structurally similar aminoglycoside antibiotics (as kanamycin is used during manufacture of NKA).
6. Abnormal coagulation status as measured by APTT, INR, and/or platelet count at Screening.
7. Not a good candidate for the injection procedure (based on the assessment of the surgeon who will be performing the injection) including patients who are morbidly obese, have excessive fat surrounding the kidney, have BMI >45, or who are otherwise at excessive risk for serious complications.
8. Clinically significant infection requiring parenteral antibiotics within 6 weeks of injection.
9. Patients with small kidneys (average size <9 cm) or only one kidney, as assessed by MRI or renal US at screening or if previously done within 1 year of screening.
10. Patients with a rapid decline in renal function over the last 3 months prior to injection or acute kidney injury.
11. Patients with any of the following conditions prior to injection: renal tumors, polycystic kidney disease, renal cysts or other anatomic abnormalities that would interfere with injection procedure (e.g., cysts in the pathway of the injection), hydronephrosis, skin infection over proposed injection sites, or evidence of a urinary tract infection.
12. Female subjects who are pregnant, lactating (breast feeding) or planning a pregnancy during the course of the study, or who are of child bearing potential and not using a highly effective method of birth control (including sexual abstinence). A highly effective method of birth control is defined as one that results in a low failure rate (i.e. less than 1 percent per year) when used consistently and correctly, such as implants, injectables, combined oral contraceptives, some intrauterine devices (IUDs), sexual abstinence, or a vasectomized partner. Subjects must be willing to continue birth control methods throughout the course of the study.
13. History of cancer within the past 3 years (excluding non-melanoma skin cancer and carcinoma in situ of the cervix).
14. Life expectancy of less than 2 years.
15. Any contraindication or known anaphylactic or severe systemic reaction to either human blood products or materials of animal (bovine, porcine) origin or anesthetic agents.
16. Positive for Human Immunodeficiency Virus (HIV), Hepatitis B Virus (HBV), or Hepatitis C Virus (HCV) assessed at the Screening Visit.
17. Subjects with active tuberculosis (TB) requiring treatment in the past 3 years.
18. Immunocompromised subjects or patients receiving immunosuppressive agents (including patients treated for chronic glomerulonephritis) within 3 months of injection. [Note: inhaled corticosteroids and chronic low-dose corticosteroids [≤7.5 mg per day] are permitted as are brief pulsed corticosteroids for intermittent symptoms (e.g. asthma).]
19. Subjects with uncontrolled diabetes (defined as metabolically unstable by the PI), or with incapacitating cardiac and/or pulmonary disorders.
20. History of active alcohol and/or drug abuse that in the investigator's assessment would impair the subject's ability to comply with the protocol.
21. Patients with clinically significant hepatic disease (ALT or AST >3.0×ULN) at Screening.
22. Patients with bleeding disorders that would, in the opinion of the Investigator, interfere with the performance of study procedures; patients taking coumarins (e.g. Warfarin) or other anticoagulants (e.g. enoxaparin or direct thrombin inhibitors).
23. Any circumstance in which the investigator deems participation in the study is not in the subject's best interest.
24. Use of any investigational product within 3 months of the injection without receiving prior written consent of the Medical Monitor.

Study Duration

Initially designed as 18 months NKA injections follow up followed by 24 month long term follow up for a total study duration of 42 months. Subsequently followed patients past protocol out to 4 years.

Study Enrollment

Up to 30 subjects undergoing NKA injection will be enrolled into the study. Patients who have received a single injection of NKA under previous research protocols may enroll in this clinical trial to receive a single additional injection. Patients who have never received an NKA injection may enroll in this clinical trial for up to a total of two (2) NKA injections, temporally spaced at least 6 months apart. All biopsies are to be taken from a single kidney, and all NKA injections are to be given into the kidney that was biopsied. Patients who complete screening procedures satisfying all I/E criteria will be enrolled into the study immediately prior to the injection. Patients who do not meet all criteria before injection will be considered screen failures. Once a patient has been injected, the patient will have completed treatment and every effort should be made to ensure the patient completes all follow-up visits. Injection dates for the first 3 patients receiving their second NKA injection will be staggered by a minimum of 3 week intervals to allow for assessment of acute adverse events and other safety parameters by the DSMB. Subsequent second injections will continue to be staggered so as to occur no less than 3 weeks apart, but individual DMSB review will not be required. At the completion of the follow-up visits, patients will continue in a long-term follow-up study. Patients will be followed for a total of 36 months following the last NKA injection under this protocol, whether the first or second injection.

Investigational Plan

Screening: Subjects who satisfy eligibility criteria may be entered into the study. Subjects must have sufficient historical data on renal function to allow for determination of the rate of progression of renal disease prior to injection (Inclusion Criterion 8). Screening procedures will include a full physical examination, electrocardiogram, and laboratory assessments (hematology, serum chemistry, and urinalysis). In addition, an MRI will be performed to assess kidney volume using site standard practices.

Biopsy: Patients not previously enrolled in a Phase 1 trial will require a renal biopsy to obtain the cells for injection. The biopsy specimens obtained from patients previously enrolled in a Phase 1 trial and maintained in a frozen state will be used to generate the second quantum of NKA to be injected under this protocol, if sufficient cells are available after thawing. If the number of cells obtained after thawing the frozen biopsy specimens is insufficient, the patient may need to have an additional biopsy procedure completed for this study.

Injection: Ten to 14 days before the scheduled injection date, subjects will report to the clinic for verification of final eligibility criteria. In addition, a renal scintigraphy study will be performed to obtain a baseline assessment of split kidney function. Subjects who meet appropriate I/E criteria will be admitted to the hospital/clinical research unit early in the morning on the day of scheduled injection (Day 0). NKA will be injected into the biopsied kidney, using one of two available options: (1) a laparoscopic approach; or (2) a percutaneous approach. The laparoscopic method may utilize robotic assistance to stabilize the kidney while the injection is performed with laparoscopic viewing; while the percutaneous method will employ a standardized technique such as utilized in the ablation of renal masses by radiofrequency or cryogenic methods. Subjects will remain hospitalized for a minimum of 2 nights and up to 4 nights following a laparoscopic injection (or until any procedure- or product-related AE's have resolved or stabilized). Patients may be discharged the same day following a percutaneous injection without complications. An ultrasound study will be performed on Day 1 to verify the lack of subclinical adverse effects for both approaches.

It is anticipated that all patients will be planned to receive 2 injections under this protocol, in order to allow dose-finding and to understand the duration of effect. Under certain circumstances a patient or investigator may decide to postpone or withhold the second dose. In general, if there appears to be any untoward safety risk, in situations including rapid deterioration of renal function, the development of uncontrolled diabetes, or the development of uncontrolled hypertension, or if there is the intercurrent development of a malignancy, the patient should not receive the second dose.

Second injections under this protocol will be staggered so that single injections in different patients occur no less than 3 weeks apart. The DSMB will review the clinical data regarding each of the first 3 second injections under this protocol, and will consult with the Sponsor before the $2^{nd}$, $3^{rd}$, and $4^{th}$ second injections are made. Subsequent second injections will continue to be staggered so as to occur no less than 3 weeks apart, but individual DMSB review will not be required.

No staggering will be required for first NKA injections under this protocol.

Post-Injection Follow-up: Subjects will return to the clinic for follow-up safety assessments on Days 7, 14, and 28 post-injection and at 2, 3, and 6 months post-injection. At 6 months post-injection, post-treatment MRI and renal scintigraphy studies will be conducted. After patients complete the 6 month efficacy visit, they will be considered for a second NKA injection. Patients receiving a second dose will follow the same follow up visits that occurred after first injection. Patients 6 month post first injection visit will serve as the patients 14 to 10 day pre-second injection visit. Patients will return for their second injection and return to the clinic for follow up safety assessments on Days 7, 14, and 28 post-injection and at 2, 3, and 6 months post-injection Patients will be followed up to 18 months in the post follow up phase with 6 months after first NKA injection and 12 months after second NKA injection. Refer to the time and events schedule on page 14 for additional post follow up time points.

Long Term Follow-up: Patients will be followed for safety and efficacy for 24 months after the 18 month initial follow up period. Telephone contact will be made 24 and 36 months after the last NKA injection, and visits will be made at 30 and 42 months after the last NKA injection.

NKA Dose

Kidney weight of the target/recipient kidney will be estimated from the results of the MRI taken during Screening. Using the preclinical studies as a guideline, the dose of NKA for this study is $3\times10^6$ cells/g estimated kidney weight (g $KW^{est}$). Since the concentration of SRC per mL of NKA is $100\times10^6$ cells/mL, the dosing volume would be 3 mL for each 100 g or 6 mL for a 200 g kidney. Based on this dosing paradigm, the following doses of NKA would be administered (Table 4):

TABLE 4

| Estimated Kidney Weight (g $KW^{est}$) | | Dose | SRC Delivered |
|---|---|---|---|
| Median Weight (g) | Weight Range (g) | Volume (mL) | (cell number; ×106) |
| 100 | 95-108 | 3 | 300 |
| 117 | 109-125 | 3.5 | 350 |
| 133 | 126-41 | 4 | 400 |
| 150 | 142-158 | 4.5 | 450 |
| 167 | 159-175 | 5 | 500 |
| 183 | 176-191 | 5.5 | 550 |
| 200 | 192-208 | 6 | 600 |
| 217 | 209-225 | 6.5 | 650 |
| 233 | 226-241 | 7 | 700 |
| 250 | 242-258 | 7.5 | 750 |
|  | >259 | 8 | 800 |

Safety Monitoring

While unforeseen adverse effects may occur, the greatest recognized risk to subjects enrolled into the study is hemorrhage following the injection procedure. Therefore, precautions have been taken to minimize the risk of excessive bleeding. Patients with abnormal laboratory values predictive of an increased risk of bleeding will not be eligible for the study. Hemoglobin/hematocrit will be monitored a) before, b) 4 hours after, and c) the day after each procedure.

Injection

During the injection procedure, hemoglobin will be monitored on a regular basis and blood pressure will be monitored continuously using standard site practices. Immediately following laparoscopic injection, the subject will remain supine for 8 hours with regular monitoring of blood pressure/pulse and hemoglobin. The subject will remain in the hospital for 2 to 4 nights following laparoscopic injection for observation of adverse events. On Day 1 following injection, an ultrasound study will be performed to verify there are no subclinical adverse effects. If clinically warranted, an ultrasound may also be performed before discharge from the clinic to ensure no adverse events are ongoing. After an injection via the percutaneous route, the patient may be discharged the same day if that is the site's usual practice after similar procedures (i.e. percutaneous ablation), after no less than 2 hours of observation and monitoring. If product- or procedure-related AE's occurred following surgery, the patient should not be released from the hospital until the AE's have either resolved, stabilized, or returned to baseline. After a laparoscopic injection, the patient should be observed in hospital for 2 to 4 nights to assess for AEs. Following discharge, subjects will be monitored at each visit for changes in renal function including the rate of progression of renal insufficiency. Laboratory values predictive of renal function will be closely monitored. Additional imaging studies may be conducted as needed in response to adverse changes in renal function.

Analysis Methods

Figure 8:
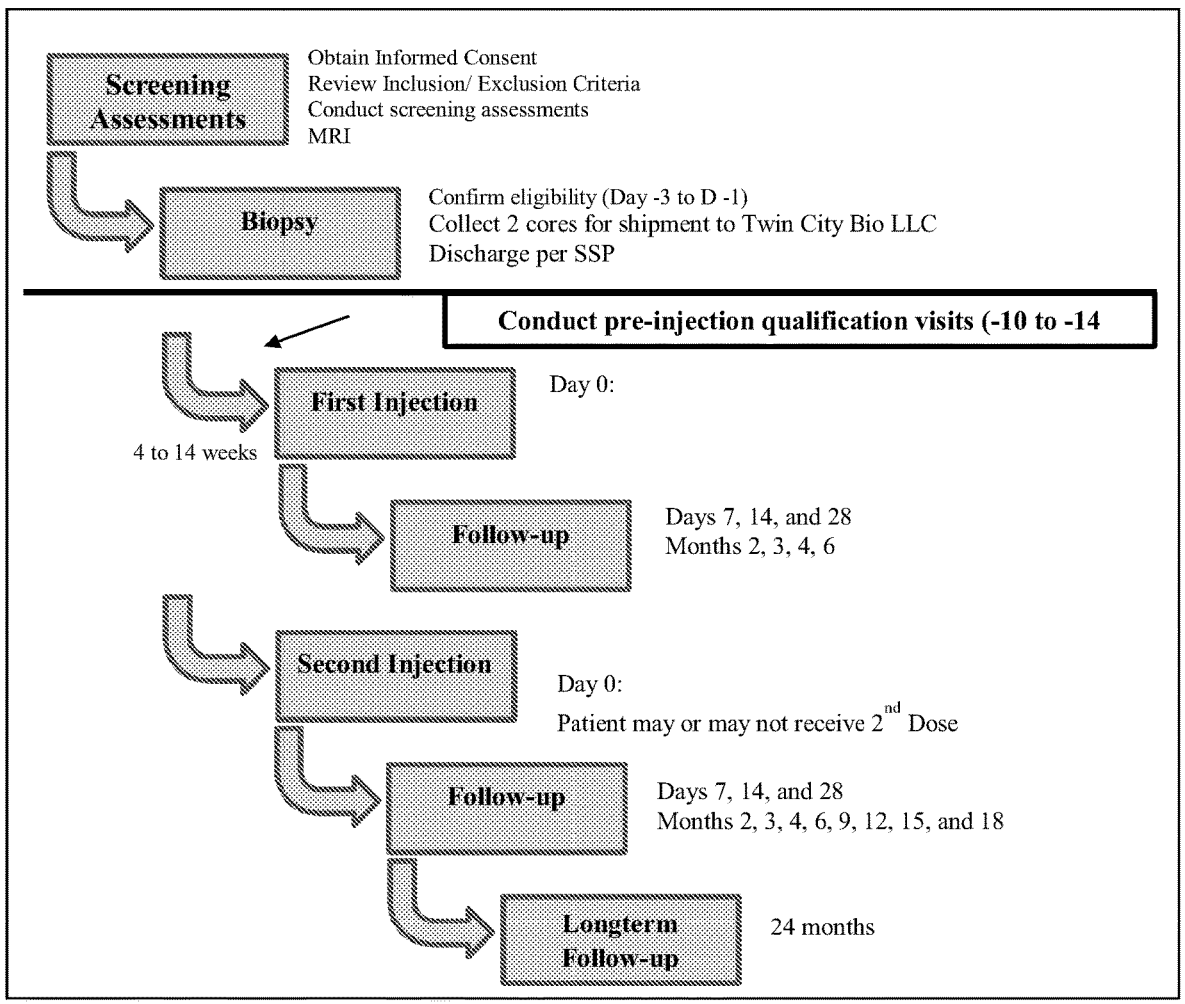
FIG. 8 depicts the study design of the PHASE II, open-label safety and efficacy study.

Up to 30 subjects will be injected with NKA. As this is a Phase II safety and early efficacy study, formal sample size calculations were not performed. The planned sample size allows for a preliminary characterization of both the safety profile and potential efficacy of the administered dose of NKA in patients with chronic kidney disease. Subgroup analyses will compare patients receiving a single injection with patients receiving two injections, and patients receiving laparoscopic injections with patients receiving percutaneous injections. The safety profile will consist primarily of an evaluation of adverse events, including events of special interest, laboratory parameters, including assessments of renal function, imaging results and vital signs. An overview of the study flow is shown in the FIG. 8.

Laboratory Assessments

Laboratory assessments are listed below in Table 5. Laboratory results will be graded using the NCI CTCAE grading scale.

TABLE 5

Laboratory Assessments

| Chemistry | Hematology |
| --- | --- |
| Standard Panel | Hemoglobin-Hb |
| Alanine Aminotransferase: ALT | Hematocrit-HCT |
| Alkaline Phosphatase: ALP | Platelets |
| Aspartate Aminotransferase: AST | RBC Count |
| Bilirubin | WBC Count |
| Creatine Kinase: CK | WBC Differential |
| Gamma-glutamyl Transferase: GGT | Coagulation Status |
| Lactate Dehydrogenase: LDH | Activated Partial Thromboplastin Time: APTT |
| Renal Analytes | |
| Albumin, serum | INR |
| Calcium, serum | Urine Chemistry |
| $CO_2$, total | Protein & Albumin |
| Creatinine, serum | Creatinine |
| Cystatin-C | Protein & Albumin: Creatinine |

TABLE 5-continued

Laboratory Assessments

| | |
| --- | --- |
| C Reactive Protein: CRP | Ratio (PCR & ACR) |
| Glucose, serum | NeutroPhase 11 Gelatinase-associated |
| Phosphorus, serum | Lipocalin (NGAL) |
| Potassium, serum | Routine Urinalysis: UA* |
| Sodium, serum | Additional Selected Analytes |
| BUN | β2-Microglobulin, serum & urine |
| Lipid Panel | Hemoglobin (Hb) A1c |
| Cholesterol | (intact) Parathyroid hormone; PTH |
| LDL | Virology |
| HDL | HIV-1, HBV, HCV |
| LDL:HDL ratio | Research (Reserve) Analytes |
| Triglycerides | Serum/plasma and urine sample Example: Fibroblast Growth Factor 23, Pentaxin 3 Pregnancy (urine) |

*Routine UA using a urine test strip (dipstick).
Microscopic analysis should only be performed if albumin, leukocytes, erythrocytes, or nitrites are positive.

eGFR: For comparison of all subjects across the study. GFR will be estimated using the CKD-EPI equation. For comparison to each subject's historical values, it may be necessary to perform a second analysis at the site laboratory used to generate the historical data.

Virology: The biopsy samples collected from the patients will be used for selection of SRC and manufacture of NKA. Therefore, the patient will be tested for viral blood-borne pathogens including HIV, HBV, and HCV.

Urine Chemistry: Over the course of the study, urine will be collected over two different time periods; 24 hour collection and spot urine. Spot urine collections will be used for urine dipstick (test stick) assessments. The times for collection of each type of sample are illustrated in the Time and Events Schedule: Laboratory Assessments. To provide a comprehensive picture of protein and albumin excretion, both total protein and albumin should be assessed in all samples as appropriate for that type of sample.

Research (Reserve) Analytes: Additional urine and serum/plasma samples will be collected, aliquotted, and stored for analysis of renal specific analytes and/or biomarkers of renal disease at a future time point. Potential analytes include fibroblast growth factor 23 (FGF23) and pentaxin 3 (PTX3). Results from these analyses will not be available, nor will they be included in the Clinical Study Report (CSR) for this study.

Pregnancy: A urine pregnancy test will be performed at the site using a test-strip. If the test is positive, then a confirmatory test will be performed at the clinical laboratory. If site practices do not accept the results of a test-strip, then a urine sample should be sent to the central laboratory for analysis.

Renal Imaging

Ultrasound

Ultrasound will be performed according to standard site procedures and will be used to assess safety during injection, prior to and following injection. An ultrasound may be conducted at other times if required for safety assessment or guidance of instrumentation during procedures. Findings from the ultrasound (e.g., resistance index, length, etc.) will be recorded on the CRF.

Magnetic Resonance Imaging

MR imaging will be performed according to site standard practices. During the site initiation visit, the MRI process will be defined for each site as dependent upon the MRI equipment in use. Generally, a 1.5-T unit should be used. Images will be used to determine kidney volume (for dosing calculations) and may be used to measure renal cortical thickness. MRI will be performed using standard sequences without injection of contrast agents. Volume measurements may be calculated, for example, using a fast 3D gradient-echo sequence, VIBE, with an acquisition time of 22 sec. and spatial resolution of 2×1.4×1.2 mm. The imaging parameters may be adjusted between patients; but the same parameters must be used for before and after images on any one patient. The specific parameters used will be recorded in the source documents and appropriate fields completed in the CRF.

Renal Scintigraphy

Renal scintigraphy has been used for a long time to measure relative kidney function. Historically, the method was performed with different radiopharmaceuticals such as dimercaptosuccinic acid labeled with Technetium-99 m (99mTc-DMSA), diethylenetriamine pentaacetic acid (99mTc-DTPA), mercaptoacetyltriglycine (99mTc-MAG3), ethylenedicysteine (99mTc-EC) and orthoiodohippurate labeled with 131-J (131J-OIH). Among these, 99mTc-DMSA, a static renal agent, is considered as the most reliable method to measure relative renal function and is the preferred agent for this study.

Renal scintigraphy using 99mTc-DMSA is being advocated as the preferred method for assessment of renal function following several types of kidney disease. Its uptake correlates with effective renal plasma flow, glomerular filtration rate and creatinine clearance. Its quantitative measurement is therefore a good index for relative renal function. Previous studies have shown that 99mTc-DMSA uptake differentiates normal from diseased kidney. If the site routinely uses a different agent, then the method should be reviewed at the site initiation visit.

The site should use their standard site procedure. Outline of an example procedure is below:

Patient should receive an intravenous injection of 50 MBq 99mTc-DMSA with imaging performed 3 hours after injection.

Patient will be placed in supine position and an acquisition of posterior view with preset time of 15 minutes, 256×256 matrix will be performed with ultra-high resolution collimator.

Differential renal function will be calculated using region-of-interest drawings.

Surgical Procedures

Biopsy

The biopsy should be collected from the left/right kidney under sterile conditions using an ultrasound or CT guided method as dictated by site standard practices. The only difference from the standard procedure may be collection of 2 tissue cores and use of a 16 gauge needle. Two biopsy renal tissue cores are needed to insure sufficient cortical tissue is collected for selection of SRC and manufacture of NKA. Likewise, a 16 gauge biopsy needle should be used to insure sufficient cortical material is collected for manufacture of NKA. If site standard practices dictate use of a 15 gauge biopsy needle, then a 15 gauge needle may be used following consultation with the Medical Monitor. In any case, it is imperative that as much cortical tissue is collected as possible. If available at the site, bedside examination of the biopsy cores may be performed to ensure sufficient cortical material is obtained.

It is important to remember that the biopsy tissue will be used to manufacture NKA, an injectable product. Therefore, the site should ensure that individuals collecting the biopsy are aware that the tissue cores must be harvested using sterile conditions so that the risk of contamination during cell expansion and selection is minimized.

Guidance on wound care and pain management following the injection procedure will be provided in the Study Reference Manual. Importantly, pain medication administered to the patient post-biopsy should selected carefully, avoiding as possible medications with nephrotoxic potential. Specialized patient care surrounding the injection will focus on minimizing potential bleeding events. The subject will remain supine for 4 hours with monitoring of hemoglobin, blood pressure, gross hematuria, abdominal/flank pain, and flank ecchymosis. In addition, the patient may be discharged the day of biopsy per site standard practice. If a subject experiences significant adverse events following the biopsy that, in the opinion of the PI would put the subject at increased risk for significant adverse effects following biopsy, then he/she will not be injected with NKA, but will be followed until resolution of the event(s) and then discontinued from the study.

Injection

NKA prepared in a sterile syringe and transported to the surgical suite will be equilibrated to 26.5±1.5° C. for a minimum of 30 minutes but not more than 120 minutes immediately prior to injection into the patient.

Patients will be injected with NKA using either: (1) a percutaneous minimally-invasive image-guided direct-needle approach, or (2) a laparoscopic technique similar to that used to deliver NKA in the canine studies and already utilized 6 or more times in the Swedish study in humans. The objective in either case is to approach at an angle allowing deposition of NKA in the renal cortex, distributed as widely as feasible. This could require imaging the kidney in a longitudinal or transverse approach, depending upon individual patient characteristics. Ideally the injection will involve multiple deposits as the injection needle/cannula is gradually withdrawn. The volume to be injected is determined by the weight of the kidney as estimated from the MRI, up to a maximum of 8 mL. For an 8 mL injection, it is anticipated that one to two mL will be deposited in 8 to 4 increments, respectively. Up to two entry points may be used to deposit the full volume of NKA into the kidney (two entry points per kidney were routinely used in all of the animal studies). NKA must be administered slowly at a rate no faster than 2 mL/min, ensuring viability of the NKA. If possible, the injection procedure will be viewed by the sponsor and actual injection of the kidney will be recorded on video for use as an educational/training tool. Prior to surgery, the site must document the specific procedural approach that will be used to access the kidney.

Percutaneous Procedure

Prior to the procedure, the operating physician will evaluate the patient, including:

a. Physical evaluation, to determine the feasibility of the procedure in general;

b. Evaluation of bleeding parameters, including coagulation panel, INR, platelets, hemoglobin, hematocrit, and other pertinent laboratory studies as indicates;

c. Review of available imaging studies, including ultrasound, MRI, and/or CT, to determine route of access, depth of kidney, and appearance of cortical-medullary junction. Mapping of potential sites of NKA cell deposition will be performed.

d. Determination of ASA class from airway assessment, medical history, allergies, and medications.

c. Interview of patient and family/supporters to discuss the procedure, its risks and possible complications, sedation, answer questions, and obtain documented informed consent.

Procedural technique: Specifically, a co-axial technique will be utilized (details below).

Image guidance: The operator will determine which kidney was biopsied, and will plan his approach to that kidney via longitudinal, transverse, or both reference planes. Imaging options during the procedure include ultrasound alone or ultrasound with complementary CT; the operator will verify and document the availability of adequate functionality, including color Doppler, measuring ability, probe frequency, and overall design.

Prior to the procedure, abnormal coagulation values will be corrected. Prophylactic antibiotics will be given intravenously according to the usual practices at the site. An initial CT scan may be ordered if necessary, for evaluation of adjacent viscera, renal location, presence of renal cysts, and for determination of the cortical-medullary junction in conjunction with ultrasound. During the procedure, moderate conscious sedation will be employed, and patient monitoring will be continuous.

NKA is targeted for injection into the kidney cortex via a needle (cannula) compatible with cells. The intent is to introduce NKA via penetration of the kidney capsule and deposit into multiple sites of the kidney cortex. Initially, the kidney capsule will be pierced using a 15-20 gauge access trocar/cannula inserted approximately 1 cm into the kidney cortex (but not advanced further into the kidney). NKA is contained in a syringe that will be attached to a blunt tipped inner needle or flexible cannula (18-26 gauge, as suitable for the access cannula). In the Phase 1 clinical study, NKA was delivered via an 18 G needle. The proposed Phase II study will utilize an 18 gauge or smaller needle (18-26 gauge) for NKA injection. The needle will be threaded inside the access cannula and advanced into the kidney, from which the NKA will be administered. Injection of the NKA will be at a rate of 1-2 ml/min. After each 1-2 minute injection, the inner needle will be retracted along the needle course within the cortex to the second site of injection; and so forth until the needle tip is at the end of the access cannula or the entire cell volume has been injected. This procedure can be used for both laparoscopic (used previously in Phase I study) and percutaneous injection of NKA. For percutaneous injection of NKA, the placement of the access cannula/trocar and needle will be performed using direct, real-time image guidance. Injection of the NKA will be monitored with ultrasound image guidance to visualize the microbubble footprint of cell deposits.

NKA injection will cease if there is imaging evidence of cell extravasation into central or peripheral renal blood vessels, the medullary portion of the kidney, or through the renal cortex and into the retroperitoneal soft tissues, or evidence of active bleeding. At this point, the needles are withdrawn. Additional renal injection sites may be chosen if NKA remains to be injected, along the same needle track, or at a new site in a different location in the kidney.

Following completion of NKA injection, the inner needle will be withdrawn and the outer cannula will remain in place for track embolization. During removal of the outer cannula (trocar), the site of the renal cortex puncture and needle track through the retroperitoneum will be embolized with absorbable gelatin particle/pledgets (e.g. Gelfoam [Pfizer]) or fibrin sealant (e.g. Tisseel [Baxter]) or other suitable agent to prevent renal bleeding.

At completion of the procedure, non-contrast CT scan or ultrasound with color Doppler evaluation will be performed to assess for puncture site cell injection and any hematoma or bleeding. For 2 to 3 hours post-procedure there will be observation in a recovery-room environment with nursing assessment and vital-sign monitoring. The patient may be discharged after that, if all indices are normal. A follow-up phone call will be conducted at 24 hours post-discharge, and follow-up in clinic will continue per protocol.

Minimally-Invasive Laparoscopic Procedure

Using the second method, the kidney will be accessed while the patient is under full anesthesia, using a robotic- or hand-assisted laparoscopic approach. (The site may choose to use HARS as described in Wadstrom et al., 2011a and 2011b, or else a standard robotically-assisted method). Using a robotic- or hand-assisted approach allows the surgeon to place the kidney in an optimal position for the injection. It also allows the surgeon to visualize and stop bleeding if this should occur. Blood pressure will be monitored continuously during surgery using standard site surgical practices.

Once the kidney is accessed, NKA will be injected at an angle that allows for deposition of NKA into the kidney cortex. The cannula should be inserted to a depth that allows for multiple depositions of NKA as the cannula is retracted from the kidney. Entry points should be off the mid line of the kidney and angled to maximize deposition of NKA into kidney cortex.

Immediately after injection, the patient will recover in a post-operative surgical recovery unit under supervision. The patient will not be taken to his/her room until all vital signs are stable. Overall, the patient will be kept in the bed for at least 8 hours with monitoring of blood pressure and pulse. The patient should be closely monitored for 24 hours by a skilled team of caregivers used to dealing with post-operative problems. If pain, fever, dramatic decreases in blood pressure/hemoglobin, or any other clinical sign/symptom indicates potential adverse reactions/events, then further physical examinations (potentially including x-rays or ultrasound investigations) must be carried out liberally and swiftly for diagnostic purposes.

In addition to standard safety measures, hemoglobin will be monitored before, 4 hours after, and then daily while hospitalized following injection. Patients will remain in the hospital for 2 to 4 nights following surgery. Patients will not be released from the hospital until procedure- and/or product-related AE's have resolved, stabilized, or returned to baseline.

Post-Procedure Evaluation of the Injection

With either procedure, if NKA leaks from the kidney during deposition, then the amount leaked should be estimated and recorded in the CRF. To prevent further leakage, the rate of injection may be slowed. As part of this protocol, injection parameters including (but not limited to) rate of injection and angle of injection may be adjusted for optimization.

Initial Results—Phase II, Open Label Safety and Efficacy Study of an Autologous NKA in Patients with Type 2 Diabetes and Chronic Kidney Disease (RMCL-001)

Patients received a 1st injection of NKA under clinical protocol TNG-CL011 (NCT02008851) and a 2nd injection of NKA approximately 2.5 years later under clinical protocol RMCL-CL001 (NCT02525263).

Figure 9:
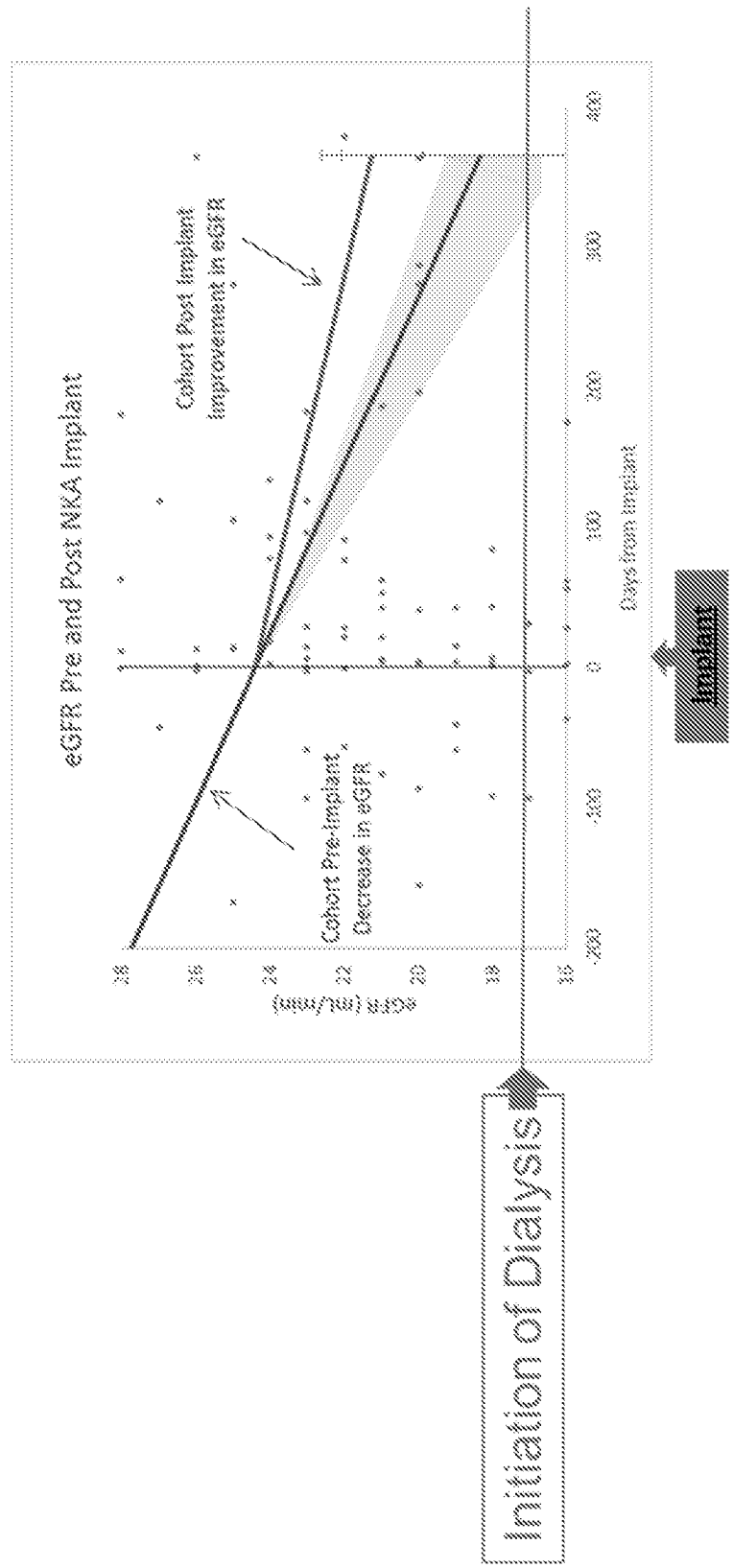
FIG. 9 depicts patient eGFR data from Phase II Clinical Study RMCL-001.

Clinical Outcomes demonstrated that in 4 of 7 patients remained dialysis free for ~4 years with stabile renal function. Pre-Implantation decline in eGFR for patient cohort was −6.1 ml/min/1.73 m3*(Red-line). (FIG. 9) NKA reduced decline in eGFR after 1 year post-implantation to –3 ml/min/1.73 m3 (Green-line). Range of kidney function decline in CKD patients and onset of dialysis (Blue zone). In summary, Population treated: patients (n=7) with pre-dialysis CKD stage 3B/4. All trial patients are commercially relevant population and served as their own controls. Pre-implantation mean eGFR=22 ml/min/1.73 m3 (CKD4). No patients had product-related adverse events. No patient received full therapeutic dose in both kidneys, just a single dose in a single kidney.

Representative metabolic measures for a patient is provided in Table 6.

TABLE 6

| Date | Visit | Height (cm) | Weight (kg) | Serum Creatinine | Cystatin C | CKDEPI | MDRD |
|---|---|---|---|---|---|---|---|
| Jul. 16, 2016 | Screen | 170.2 Cm | 120.3 | 5.95 | 3.7 | 15 | 16 |
| Jul. 20, 2016 | Re-Screen | | 115.9 | 4.95 | | 18 | 19 |
| Jul. 28, 2016 | Day –14 to –10 | | 115.9 | 5.05 | | 17 | 19 |
| Aug. 9, 2016 | Day 0 | | 113 | 6.55 | | 13 | 14 |
| Aug. 15, 2016 | Day 7 | | 112.8 | 7.68 | 3.9 | 10 | 11 |
| Aug. 19, 2016 | Day 14 | | 114.2 | 5.83 | 3.49 | 15 | 16 |
| Sep. 7, 2016 | Day 28 | | 112.2 | 5.16 | 3.2 | 17 | 18 |
| Oct. 6, 2016 | Month 2 | | 111.1 | 5.79 | | 14 | 16 |
| Nov. 4, 2016 | Month 3 | | 111.6 | 6.25 | 4.02 | 18 | 20 |
| Feb. 7, 2017 | Month 6 | | 114.6 | 7.72 | 3.91 | 14 | 16 |
| Mar. 17, 2017 | Unscheduled | | | 6.47 | | | 11 |
| Apr. 7, 2017 | End of Study | | | | | | |

Figure 10A:
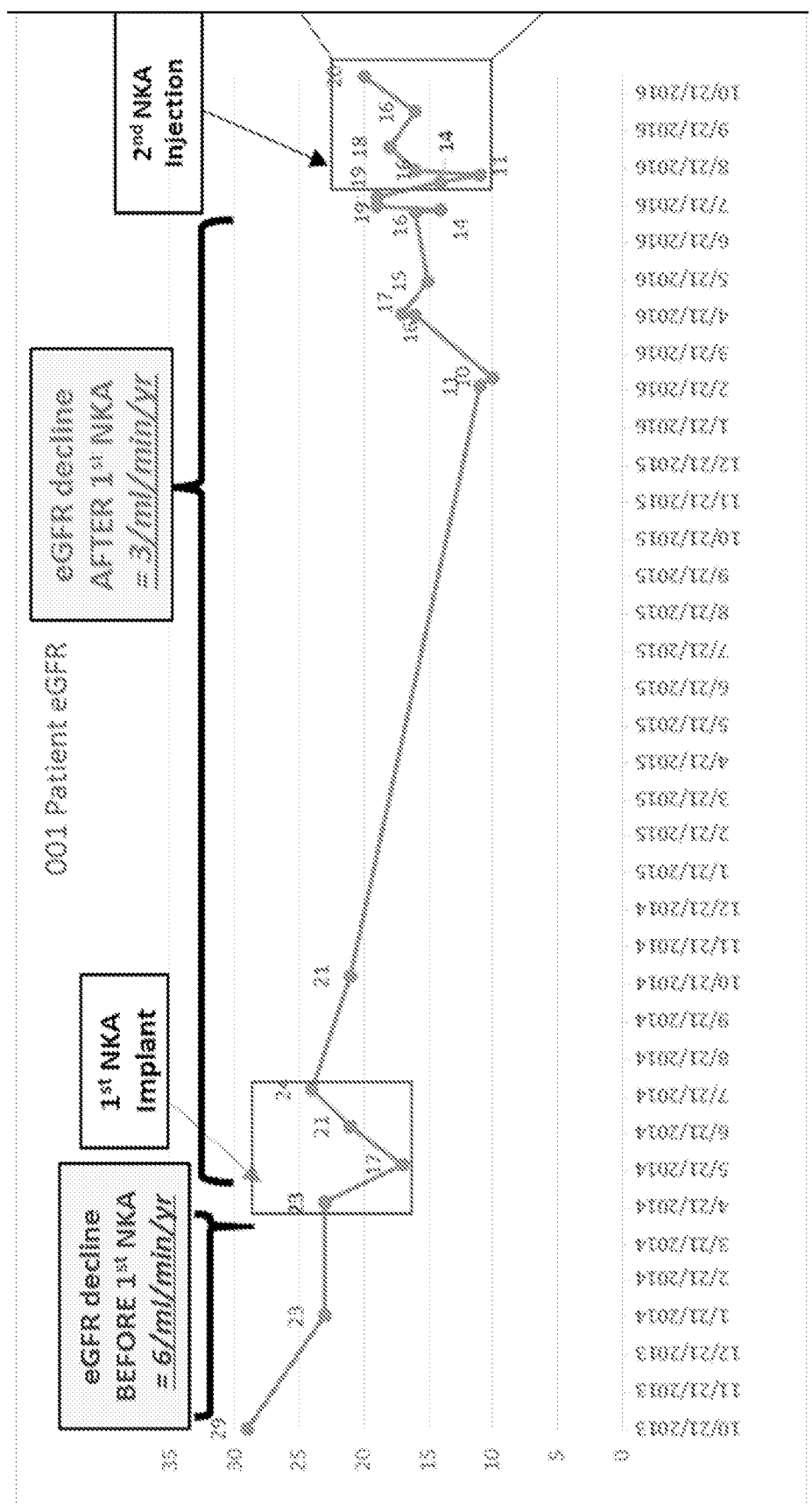
FIG. 10A &B highlight the eGFR increase and stability after 2nd NKA Injection.
Figure 10B:
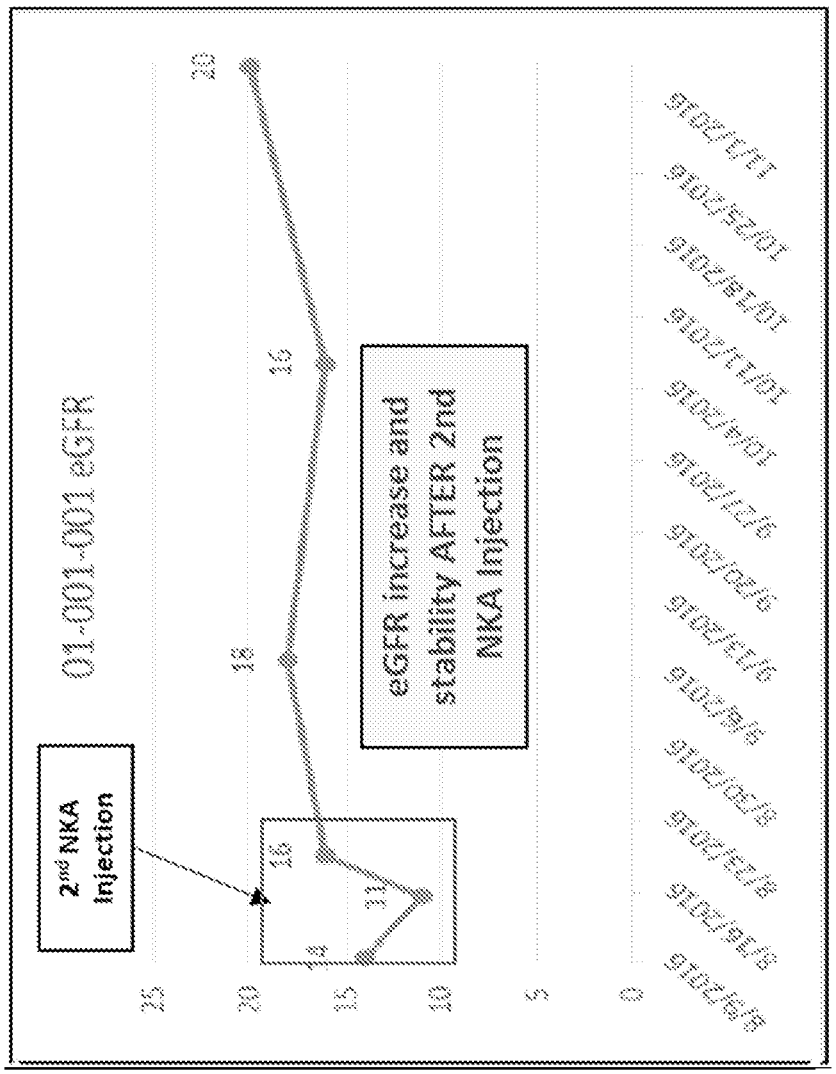

Prior to the first NKA injection, this patient suffering from Type 2 Diabetes and Chronic Kidney Disease had a rate of eGFR decline of 6/ml/min/yr. In this patient, the pre-NKA injection—CKD 4 eGFR ~20 ml/min. After receiving a first NKA injection, the rate of eGFR decline was reduced to approximately 50% to 3/ml/min/yr over a 2.5 year period (FIG. 10A). After receiving the 2nd NKA injection, the eGFR increased by approximately 50% three months post-injection, stabilized in the following 6 months of observation and rescued the patient for 8 months of dialysis-free life (FIG. 10B).

Figure 11:
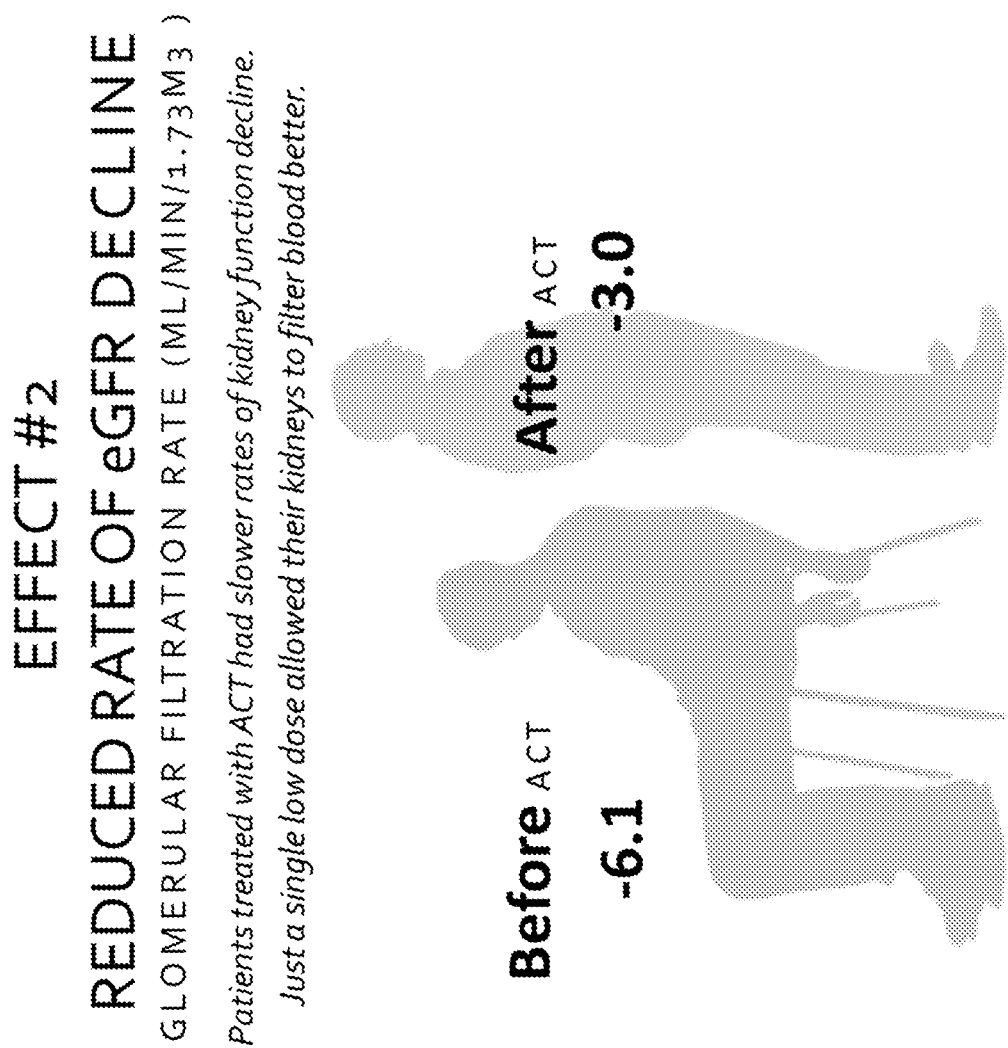
FIG. 11 illustrates the reduced rate of eGFR decline.
Figure 12:
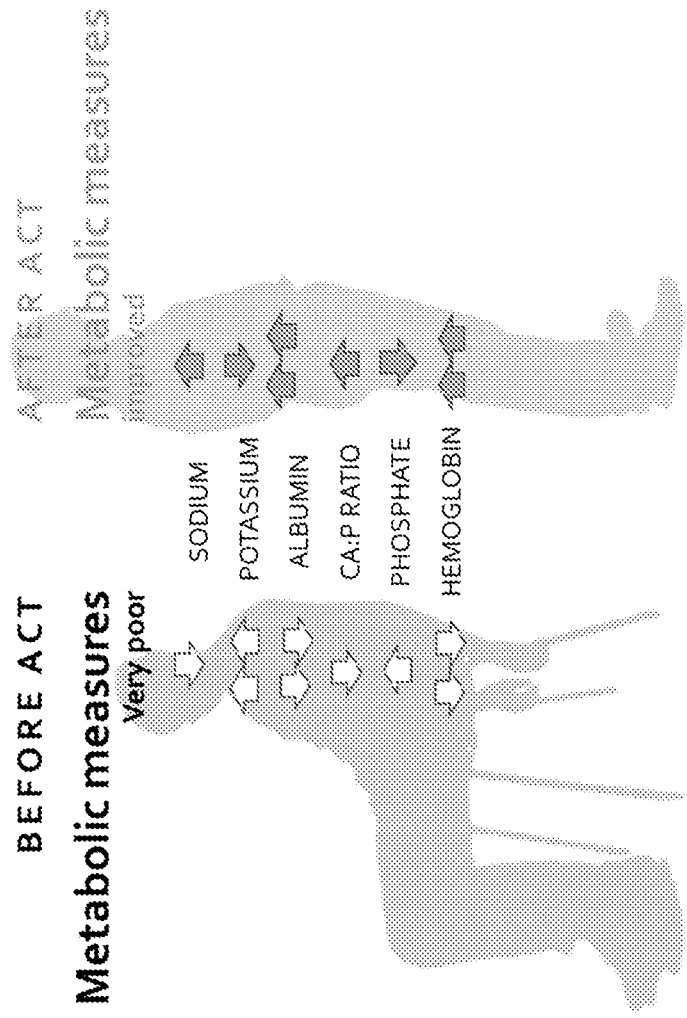
FIG. 12 illustrates the effect of Advanced Cell Therapy (ACT) on a variety of metabolic measures.

The reduced rate of eGFR decline, indicative of glomerular filtration rate, suggests that patients treated with NKA (also referred to as Advanced Cell Therapy (ACT)) had slower rates of kidney function decline. Just a single low dose allowed their kidneys to filter blood more effectively (FIG. 11). Furthermore, ACT is a therapy for co-morbidities. Patients treated with ACT were able to reduce blood pressure medication because better kidney function supports better metabolic and endocrine function (FIG. 12).

Overall, this data strongly supports the efficacy of re-injecting patients with a second NKA injection. It may also suggest re-dosing 3 months after the first dose to ensure durable impact on kidney function. Dosing both kidneys or having the ability to do multiple doses (i.e. >2) in the same kidney may further increase kidney function.

Example 3—NKA Injection for Interventional Radiology

Clinic Evaluation

For clinical evaluation prior to procedure, it is recommended to ensure adequate renal visualization, renal axis, and kidney size, presence of renal masses/cysts/para-pelvic cysts, renal cortex thickness and depth of kidneys from skin surface.

NKA Delivery

Cell suspension: Volume to be determined by pre-procedure MRI volumetric 3D evaluation.

Needle size and placement: 18 gauge (ga) diamond tip needle inserted with ultrasound (US)/computerized tomography (CT) scan guidance and needle tip advanced beneath the capsule 5-10 mm into the renal parenchyma. A 21-27 ga inner needle is advanced through outer needle into the subcapsular renal parenchyma approximately 4-5 cm distal to the tip of the trocar needle or until the tip reaches the more distal portion of the far renal subcortical tissue. Advance needle as new the subcortical capsules as possible but avoid capsule perforation.

Needle placement may encounter the lateral/medial cortex contour, and may shortening or lengthening the cell delivery depth in the cortical/subcapsular location. Ideal delivery site via the transverse plane will be in the mid to lower pole location. Needle advancement is done with US guidance to ensure proper placement and confirmed if necessary with axial CT imaging.

Figure 13:
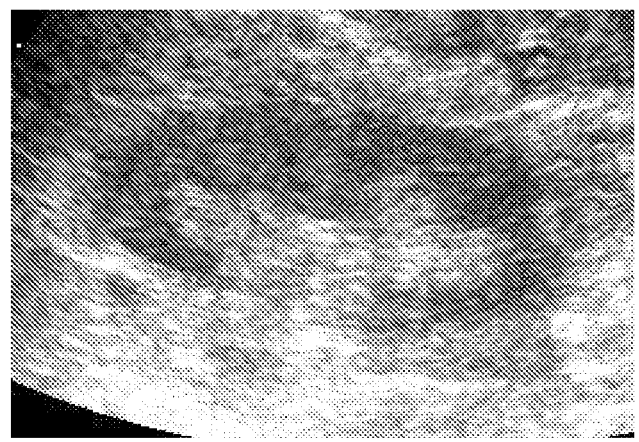
FIG. 13 is a longitudinal renal ultrasound showing a small echogenic kidney with difficult longitudinal access approach due to deep position and axis.
Figure 14:
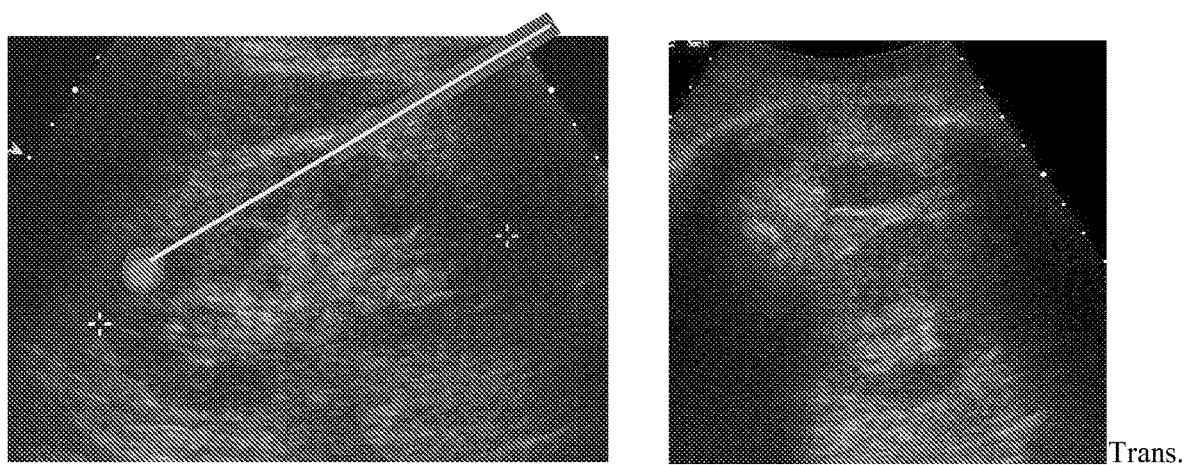
FIG. 14 is a longitudinal renal ultrasound demonstrating trajectory of outer 18 ga trocar needle (thick) and inner 25 ga injection needle (thin). Circle represent NKA injection.
Figure 15:
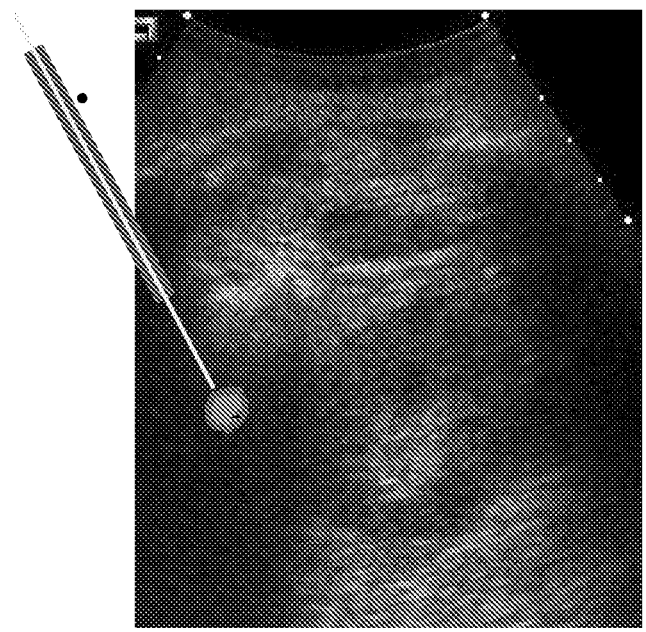
FIG. 15 shows the transvers renal ultrasound direction of trocar and inner injection needle and approximate trajectory. Circle represent NKA injection

Initial and final needle placement is confirmed with US/CT imaging and recorded. The distance from the lower pole to the needle entrance site is measured and recorded. (See FIGS. 13-15)

NKA Cell injection: The cell solution will be delivered by the study coordinator in conjunction with the preparation research pharmacy, in with a predetermined volume in a 10 ml syringe. If sterile then the syringe can be passed to the IR operator. If nonsterile, then transfer the NKA from preparation syringe to a sterile syringe. A connector tube is inserted between the syringe and needle hubs in order to allow for injection flexibility.

The needle is withdrawn 1 cm from original tip position and the stem cell injection started, injecting up to 2 ml of cell solution at the rate of 1-2 ml of cell slurry per minute under US guidance observing for echogenic dispersion of the slurry into the renal cortex tissue. A timer is recommended to monitor injection rate. The injection is then stopped and the needle withdrawn another 1 cm, followed by the second injection of up to 2 ml of cell solution. This is repeated for up to a total of 4 injections of up to 8 ml of cell solution. If the renal parenchyma does not accommodate a 4 cm injection length then the injections are stopped at the length and corresponding volume that the renal size allows. Do not inject more than 8 ml per needle puncture. At conclusion of the needle injection place small (2-4 mm diameter×10 mm length) gelfoam (Gelatin sponge, Pfizer) plug into the needle before withdrawal from needle.

If injection volumes are limited due to needle penetration into the cortex, obstruction or other constraints such that the total cell solution volume injected is less than the required injection volume based on renal size, a second renal puncture will be necessary to continue or finish the NKA delivery. Careful observation of needle withdrawal and stable position of trocar needle may require an assistant to manage US imaging and stabilize trocar needle. If incomplete delivery obtained with initial needle placement then second or third injection site will be chosen.

Under US/CT guidance, a second puncture is made with the 18 gauge trocar needle into a second location at least 2 cm superior or inferior to the first delivery site. The injection site may me along the same renal margin or the opposite side. The needle placement, US/CT needle tip confirmation, and injection method is repeated in a similar manner.

Masses: Renal cysts are avoided. If necessary, aspirate renal cyst(s) to avoid injection and collection of cells into the cyst if no other access site is available. Solid masses are avoided and solid renal mass workup initiated to include MRI or CT imaging and possible biopsy. Solid masses should be excluded prior to injection unless there is a delay between NKA preparation and injection and a new mass appears.

Injection rate time: 1-2 millimeter of cell solution per minute under US observation.

CT scan without contrast: CT scan with 5 mm thick axial slices and diagnostic quality mA from lower liver through the kidneys with localization grid placed over kidney to be injected. Select posterior or posterior-lateral approach avoiding other structures in the mid to lower pole region. Patient positioned prone or decubitus if necessary.

Sedation: Moderate conscious sedation. General anesthesia for certain situations to include ASA 4,5, difficult airway, patient request, inability to position, heart/lung/liver comorbidities or other increased anesthesia risk situations.

CT or US guidance: Needle placement along longest transverse axis from posterior or lateral by CT or US guidance of from longitudinal direction if able to address approach angle. Cell delivery to be observed with US in order to identify microbubble tract as needle is withdrawn. Length and rate of delivery into the kidney will determine the amount of cell slurry injected.

Final CT and US to be done after withdrawal to evaluate for bleeding, injection site complications to kidney and adjacent organs.

Example 4—A Phase II, Open-Label Safety and Tolerability Study of an Autologous Neo-Kidney Augment (NKA) in Patients with Type 2 Diabetes and Chronic Kidney Disease (RMCL-002 and RMCL-003)

A regenerative cell-based product, Neo-Kidney Augment (NKA), has been developed with the aim of improving renal function in subjects who have CKD and T2DM. As noted above, therapeutic intervention with NKA is intended to delay the need for renal replacement therapy (dialysis or transplant) which, based on the current standard-of-care, is inevitable for patients with end-stage CKD. The purpose of the present study is to compare the safety and efficacy of up to 2 injections of NKA given 3 months (+12 weeks) apart (maximum) in subjects who are randomized to receive their first treatment as soon as the NKA product is made available versus subjects who are randomized to undergo contemporaneous, standard-of-care treatment for CKD during the first 12-18 months prior to receiving up to 2 injections of NKA. In addition, each subject's annual rate of renal decline, based on adequate historical, clinical data from 18 months prior to the Screening Visit, will serve as a comparator to monitor the rate of progression of renal insufficiency pre- and post-randomization.

We propose that NKA treatment will reduce the rate (slope) of eGFR decline and improve renal function over the 24 month period following the last NKA injection.

Study Objectives

Primary Objective: The primary objective of the study is to assess the safety of NKA injected in one recipient kidney.

Primary Outcome/Endpoint Measures: procedure and/or product related adverse events (AEs) through 24 months post-injection.

Secondary Objective: The secondary objective of the study is to assess the safety and tolerability of NKA administration by assessing renal-specific adverse events over a 24 month period following injection.

Secondary Outcome/Endpoint Measures: renal-specific laboratory assessments through 24 months post-injection.

Exploratory Objective: Exploratory objectives of the study are designed to assess the impact of NKA on renal function over a 24 month period following injection.

Exploratory Outcome/Endpoint Measures: clinical diagnostic and laboratory assessments of renal structure and function (including eGFR, serum creatinine, and proteinuria) to assess changes in the rate of progression of renal disease.

Study Design

Multi-center, prospective, open-label, single-group study. All subjects will be treated with two NKA injections 3 months (+12 weeks) apart after biopsy.

Randomization:

Open-label, non-randomized.

Control Group

Each subject will serve as his or her own control; the patient's previous medical history, which must include a minimum 6 month period of observation of renal function, will serve as the control for rate of progression of renal insufficiency.

Sample Size

Up to 10 patients will be treated with NKA. As this is a Phase II safety study, robust statistical analysis will not be performed. Therefore, the sample size proposed for this study is a size typical for in Phase 1 studies, allowing for identification of safety outcomes in a limited population.

Study Population

Male or female patients 30 to 85 years of age with CKD and eGFR between 14 and 20 mL/min/1.73 $m^2$. Patients should have sufficient historical clinical data to determine their individual rate of CKD disease progression.

Inclusion Criteria: Unless otherwise noted, subjects must satisfy each inclusion criterion to participate in the study. Inclusion criteria will be assessed at the Screening Visit, prior to renal biopsy, and before each NKA injection unless otherwise specified.

1. The subject is male or female, 30 to 85 years of age on the date of informed consent.
2. The subject has an established diagnosis of T2DM.
3. The subject has an established diagnosis of diabetic nephropathy as the underlying cause of renal disease.
4. The subject has an established diagnosis of CKD not requiring renal dialysis, defined as having an eGFR between 14 and 20 mL/min/1.73 m² inclusive at the Screening Visit and prior to NKA injection.
5. The subject has urine albumin excretion greater than or equal to 30 mg/day.
6. The subject has blood pressure less than 140/90 at the Screening Visit, prior to renal biopsy, and prior to NKA injection(s). Note BP should not be significantly below 115/70.
7. The subject has stable blood pressure or has ongoing and stable treatment with an angiotensin-converting-enzyme inhibitor (ACEI) or an angiotensin receptor blocker (ARB) initiated at least 8 weeks prior to renal biopsy. Treatment must be stable during the 6 week period immediately prior to NKA injection. Stable treatment is defined as dose adjustment no less than one half of the current dosage and no more than 2 times the current dosage. Dose interruptions up to 7 days due to medical necessity are allowed. A subject who is intolerant to ACEI or ARBs may be included as long as he/she has stable blood pressure within the specified limits.
8. A minimum of 2 measurements of eGFR or sCr should be obtained at least 3 months apart prior to the Screening Visit or within the previous 18 months to define the rate of progression of CKD. The subject should have adequate, historical clinical data to provide a reasonable estimate of the rate of progression of CKD following consultation with the Medical Monitor (to ensure that there are sufficient data).
9. The subject is willing and able to refrain from NSAID consumption (including aspirin) as well as clopidogrel, prasugrel, or other platelet inhibitors during the period beginning 7 days before through 7 days after both the renal biopsy and NKA injection(s).
10. The subject is willing and able to refrain from consumption of fish oil and platelet aggregation inhibitors, such as dipryridamole (ie, Persantine®), during the period beginning 7 days before through 7 days after both the renal biopsy and NKA injection(s).
11. The subject is willing and able to cooperate with all aspects of the protocol.
12. The subject is willing and able to provide signed informed consent.

Exclusion Criteria: Subjects who satisfy any exclusion criterion listed below are not eligible to participate in the study. Exclusion criteria will be assessed at the Screening Visit, before renal biopsy, and before each NKA injection unless otherwise noted.
1. The subject has a history of type 1 diabetes mellitus.
2. The subject has a history of renal transplantation.
3. The subject has a serum HbA1c level greater than 10% at the Screening Visit.
4. The subject has uncontrolled diabetes (defined as metabolically unstable by the Investigator).
5. The subject has hemoglobin levels less than 9 g/dL prior to each NKA injection.
6. The subject has abnormal coagulation status as measured by activated partial thromboplastin time (APTT), prothrombin time international normalized ratio (PT INR), and/or platelet count at the Screening Visit.
7. The subject has a bleeding disorder(s) or is taking anticoagulants, such as Coumadin® (warfarin) or direct thrombin inhibitors that, in the judgment of the Investigator, would interfere with the performance of study procedures.
8. The subject has small kidneys (average size less than 9 cm) or has only one kidney, as assessed by ultrasound and/or MRI prior to renal biopsy, unless earlier radiology reports (generated within 1 year of the Screening Visit) are made available to confirm kidney size and number.
9. The subject has a known allergy or contraindication(s), or has experienced severe systemic reaction(s) to kanamycin or structurally similar aminoglycoside antibiotic(s)
10. The subject has a history of anaphylactic or severe systemic reaction(s) or contraindication(s) to human blood products or materials of animal origin (eg, bovine, porcine).
11. The subject is not a good candidate to undergo percutaneous NKA injection, in the judgment of the surgeon or physician who will perform the procedure. This includes individuals who are morbidly obese (defined as BMI greater than 45 kg/m2), have excessive fat surrounding the kidney, or who are otherwise at excessive risk for serious complications.
12. The subject has a history of severe systemic reaction(s) or any contraindication to local anesthetics or sedatives.
13. The subject has a clinically significant infection requiring parenteral antibiotics within 6 weeks of NKA injection.
14. The subject has acute kidney injury or has experienced a rapid decline in renal function during the last 3 months prior to NKA injection.
15. The subject has any of the following conditions prior to NKA injection: renal tumors, polycystic kidney disease, anatomic abnormalities that would interfere with the NKA injection procedure or evidence of a urinary tract infection.
16. The subject has incapacitating cardiac and/or pulmonary disorders.
17. The subject has a history of cancer within the past 3 years (excluding non-melanoma skin cancer and carcinoma in situ of the cervix).
18. The subject has clinically significant hepatic disease (ALT or AST greater than 3 times the upper limit of normal) as assessed at the Screening Visit.
19. The subject is positive for active infection with Hepatitis B Virus (HBV), or Hepatitis C Virus (HCV), and/or Human Immunodeficiency Virus (HIV) as assessed at the Screening Visit.
20. The subject has a history of active tuberculosis (TB) requiring treatment within the past 3 years.
21. The subject is immunocompromised or is receiving immunosuppressive agents, including individuals treated for chronic glomerulonephritis within 3 months of NKA injection. Note: inhaled corticosteroids and chronic low-dose corticosteroids (less than or equal to 7.5 mg per day) are permitted as are brief pulsed corticosteroids for intermittent symptoms (eg, asthma).
22. The subject has a life expectancy less than 2 years.
23. The female subject is pregnant, lactating (breast feeding), or planning a pregnancy during the course of the study. Or, the female subject is of child-bearing potential and is not using a highly effective method(s) of birth control, including sexual abstinence. Or, the female subject is unwilling to continue using a highly-effective method of birth control throughout the duration of the study.

Note: A highly effective method of birth control is defined as one that results in a low failure rate (ie, less than one percent per year) when used consistently and correctly, such as implants, injectables, combined oral contraceptives, some intrauterine devices IUDs, sexual abstinence, or a vasectomized partner.

24. The subject has a history of active alcohol and/or drug abuse that, in the judgment of the Investigator, would impair the subject's ability to comply with the protocol.
25. The subject's health status would, in the judgment of the Investigator, be jeopardized by participating in the study.
26. The subject has used an investigational product within 3 months prior to NKA injection without receiving written consent from the Medical Monitor.

Number of Sites

Up to 5 clinical centers will be included in the study.

Study Duration

Treatment to begin as soon as the NKA product is made available and assuming a one month interval prior to receiving the first NKA injection, and assuming a 3 month interval before receiving the second injection, plus a 24 month follow up period after the final injection, the duration of treatment would be 28 months for a series of 2 NKA injections.

Study Enrollment

Up to 10 subjects will be enrolled into the study. Patients who complete screening procedures satisfying all I/E criteria will be enrolled into the study immediately prior to the biopsy. Patients who do not meet all criteria before the biopsy is taken will be considered screen failures. Patients who have a biopsy but are not injected for whatever reason will be discontinued from the study and may be replaced. Once a patient has been injected, the patient will have completed treatment and every effort should be made to ensure the patient completes all follow-up visits.

Investigational Plan

Screening: Subjects who satisfy eligibility criteria and provide written informed consent may be entered into the study. The subject should have adequate, historical clinical data to provide a reasonable estimate of the rate of progression of CKD following consultation with the Medical Monitor. Screening procedures include a full physical exam, ECG, and laboratory assessments (hematology, clinical chemistry, and urinalysis). An ultrasound will be performed to confirm the presence of two kidneys with normal anatomic features. A MRI study will determine kidney size and volume.

Renal Biopsy: Three days or less before undergoing renal biopsy, enrolled subjects will report to the clinic and undergo an interim physical exam along with an ECG and renal MRI (if not completed during or after the Screening Visit). Laboratory tests, including renal function, hemoglobin, and a pregnancy test for females also will be performed. Eligible subjects satisfying all inclusions and exclusion criteria will be admitted to the hospital/clinical research center to undergo a kidney biopsy. A minimum of 2 tissue cores measuring at 1.5 cm a piece must be collected using a 16 gauge biopsy needle to provide sufficient material for the manufacture of NKA. Subjects who do not experience complications from the biopsy may be discharged the same day consistent with site standard practice.

NKA Injection: Ten to 14 days before the scheduled injection date, subjects will undergo an interim physical exam for ongoing verification of inclusion and exclusion criteria. Subjects also will undergo renal scintigraphy (ie, split kidney function scan) to find out what percentage each kidney contributes to total baseline kidney function. On the day of the scheduled NKA injection, eligible subjects will be admitted into the hospital/clinical research unit. After warming to liquefy the hydrogel, NKA will be injected into the same kidney that was previously biopsied using a percutaneous approach. This procedure will follow a standardized technique, such as that used in the ablation of renal masses by radiofrequency or cryogenic methods. Subjects without complications may be discharged the same day consistent with site standard practice. An ultrasound will be performed the day after injection to detect possible, subclinical AEs. It is anticipated that all subjects will receive 2 NKA injections given 3 months (+12 weeks) apart. The first and second injections will occur in the same kidney in which the biopsy was taken. Therefore only one kidney will be used for the duration of this study.

Follow-up: Subjects will complete follow-up evaluations on Days 1, 7, 14, 28 (+3 days) and Month 2 (±7 days) after the first and second NKA injections. Depending on when the second injection is administered (ie, at 3 months [+12 weeks]), subjects may undergo evaluations at 3 and 6 months after the first NKA injection. Following the final NKA injection, subjects will complete long term, follow up assessments of safety and efficacy through 6, 9, 12, 15, 18, 21, and 24 months post-treatment.

Safety Monitoring: Hemorrhage following NKA injection is a known and foreseeable risk to subjects participating in this study. Therefore, hemoglobin will be measured by the site's local laboratory at the following times: a) before, b) after procedure per site standard practice Investigational Product, Dosage and Mode of Administration Investigational Product: NKA is made from expanded autologous selected renal cells obtained from each individual subject's kidney biopsy. To manufacture NKA, biopsy tissue from each enrolled subject will have renal cells expanded and SRC selected. SRC will be formulated in a gelatin based hydrogel at a concentration of $100 \times 10^6$ cells/mL, packaged in a 10 mL syringe, and shipped to the clinical site.

Dosage: The volume of NKA to be administered will be determined by pre-procedure MRI volumetric 3D evaluation or ellipsoid formula (Length×width AP plane×width Transverse plan×0.62). Based on pre-clinical data, the dose of NKA will be $3 \times 10^6$ cells/g estimated kidney weight (g $KW^{est}$). Since the concentration of SRC per mL of NKA is $100 \times 10^6$ cells/mL, the dosing volume will be 3.0 mL for each 100 g of kidney weight. Using this dosing paradigm, the following table shows the dosing volume and number of SRC to be delivered relative to estimated kidney weight (Table 7). The maximum volume of NKA injected into the biopsied kidney will be 8.0 mL.

TABLE 7

| Estimated Kidney Weight (g $KW^{est}$) | | Dosing | SRC Delivered |
|---|---|---|---|
| Median Weight (g) | Weight Range (g) | Volume (mL) | (Number of Cells × $10^6$) |
| 100 | 95-108 | 3.0 | 300 |
| 117 | 109-125 | 3.5 | 350 |
| 133 | 126-141 | 4.0 | 400 |
| 150 | 142-158 | 4.5 | 450 |
| 167 | 159-175 | 5.0 | 500 |
| 183 | 176-191 | 5.5 | 550 |

TABLE 7-continued

| Estimated Kidney Weight (g KW$^{est}$) | | Dosing | SRC Delivered |
|---|---|---|---|
| Median Weight (g) | Weight Range (g) | Volume (mL) | (Number of Cells × 10$^6$) |
| 200 | 192-208 | 6.0 | 600 |
| 217 | 209-225 | 6.5 | 650 |
| 233 | 226-241 | 7.0 | 700 |
| 250 | 242-258 | 7.5 | 750 |
| — | >259 | 8.0 | 800 |

*Kidney weight will be estimated from the results of an MRI study performed on or after the Screening Visit until Day 0 (renal biopsy).

It is anticipated that all subjects will receive two planned NKA injections to allow dose-finding and evaluate the duration of effects. The first and second injections will occur in the same kidney in which the biopsy was taken. In some cases, a subject or the Investigator may decide to postpone or withhold the second NKA injection. For example, if there appears to be any untoward safety risk, or rapid deterioration of renal function, or the development of uncontrolled diabetes or uncontrolled hypertension, or the development a malignancy or an intercurrent infection, then the second NKA injection should not be administered.

Mode of Administration: NKA will be injected into the biopsied kidney using a percutaneous approach. The percutaneous method will employ a standardized technique (such as that utilized in the ablation of renal masses by radiofrequency or cryogenic methods).

Statistical Analysis Methods

Statistical analyses will be primarily descriptive in nature and no statistical hypothesis testing is planned for the study. Unless otherwise specified, continuous variables will be summarized by presenting the number of non-missing observations (n), mean, standard deviation, median, minimum, and maximum. Categorical variables will be summarized by presenting frequency count and percentage for each category.

Rationale for Two NKA Injections

It is anticipated that all subjects will receive two planned NKA injections to allow dose-finding and evaluate the duration of effects. The scientific rationale, based on non-clinical studies, is that the biologically active component of NKA (homologous, autologous, SRC) delays progression of experimental models of CKD by augmenting renal structure and function. (Bruce et al. Selected renal cells modulate disease progression in rodent models of chronic kidney disease via NF-κB and TGF-β1 pathways. *Regen Med.* 2015; 10:815-39; Bruce et al. Exposure of cultured human renal cells induces mediators of cell migration and attachment and facilitates the repair of tubular cell monolayers in vitro. Experimental Biology Meeting, Washington, DC, 2011; Atala et al. Tissue-engineered autologous bladders for patients needing cystoplasty. *Lancet.* 2006; 367:1241-46; Jayo et al. Long-term durability, tissue regeneration and neo-organ growth during skeletal maturation with a neo-bladder augmentation construct. *Regen Med.* 2008; 3:671-82; Jayo et al. Early cellular and stromal responses in regeneration versus repair of a mammalian bladder using autologous cell and biodegradable scaffold technologies. *J Urol.* 2008; 180:392-7; Jayo et al. Tissue engineering and regenerative medicine: role of toxicologic pathologists for an emerging medical technology. *Toxicol Pathol.* 2008; 36:92-6) As a result, the more cells that can be infused, the greater the potential improvement in renal function. The total number of cells that can be delivered into a kidney at one time is limited by the size of the kidney, however, as well as the inelasticity of the renal capsule. Consequently, it may be possible to improve therapeutic benefit by administering greater numbers of SRC via a second injection, given after cells from the first injection have become incorporated into the kidney.

Apart from increasing SRC numbers by administering 2 NKA injections into the same kidney, the duration of effects can be evaluated. The processes by which functional nephrons become disabled in kidneys with CKD may, over time, adversely affect "new" cells delivered via NKA injection. Consequently, NKA might not result in long-term, therapeutic benefit. Exploring the effects from a second NKA injection, given at an appropriate interval after the first injection, would address this question.

In the present study, subjects will be administered a second NKA injection 3 months after the first injection, with a study visit window of 12 weeks. Regardless, every attempt should be made to ensure that the second NKA injection is administered 3 months after the first injection. However, if there appears to be any untoward safety risk, or rapid deterioration of renal function, or development of uncontrolled diabetes or uncontrolled hypertension, or development of a malignancy or an intercurrent infection, then the second NKA injection should not be administered.

Safety of Two NKA Injections

To assess the safety of administering two doses of NKA into the biopsied kidney, a canine GLP toxicology study was conducted. Similar to the clinical study design, study animals (n=8) underwent renal biopsies at 4 to 6 weeks prior to baseline. Each dose was delivered into both kidneys at baseline and 3 months; animals were observed for 6 months following the baseline injection. While control animals received PBS, NKA-treated animals received a two-fold greater dose than that used in the present clinical study.

Briefly, no detrimental effects of two doses of NKA into the biopsied kidney were observed in comparison to control animals 6 months after baseline treatment. Pathological assessment showed no NKA safety-related (macroscopic or microscopic) findings in either the target organ (kidney) or non-target organs examined. No treatment-related kidney findings were noted following enhanced evaluation of 8 areas of each kidney (3 stains per area), including assessment and scoring of 150 glomeruli per kidney. All kidneys appeared normal, apart from changes related to injection site scars. There were no signs of renal insufficiency, and no indications of decreased GFR. Detailed information is provided in the Investigator's Brochure.

Laboratory Assessments

Planned clinical laboratory evaluations are listed in Table 8. Analyses will be conducted by a central laboratory, except as noted. The scheduled for collecting biological samples during the study are discussed above.

TABLE 8

Clinical Laboratory Evaluations

| Clinical Chemistry | Hematology | Urinalysis |
| --- | --- | --- |
| Alkaline phosphatase | Hematocrit | Albumin |
| ALT | Hemoglobin | β2-Microglobulin |
| AST | RBC count & indices | Creatinine |
| β2-Microglobulin | WBC count & differential | Protein |
| Bilirubin | Pregnancy | Protein & |
| Creatinine kinase | hCG (serum)- | Albumin:Creatinine |
| FSH (females only) | confirmatory | Ratio |
| GGT | Serology | NGAL |
| $HbA_{1c}$ | HBV | Standard Panel |
| LDH | HCV | pH |
| PTH (intact) | HIV | Ketones |
| Renal Analytes | Coagulation Status | Protein |
| Albumin | APTT | Blood |
| BUN | PT-INR | Glucose |
| Calcium | Platelet count | Pregnancy |
| $CO_2$, total | Lipid Panel | Microscopic analysis |
| Cystatin-C | Cholesterol | Drug Screen |
| CRP | LDL | Amphetamine |
| eGFR (calculated) | HDL | Barbiturates |
| Glucose | LDL:HDL ratio | benzodiazepines |
| Phosphorus | Triglycerides | Cocaine |
| Potassium | | Opiates |
| Sodium | | Tetrahydrocannabinol |
| | | Phencyclidine |

Abbreviations:
ALT (Alanine Aminotransferase);
APTT (Activated Partial Thromboplastin Time):
AST (Aspartate Aminotransferase);
BUN (Blood Urea Nitrogen);
CRP (C-Reactive Protein);
FSH (Follicle-Stimulating Hormone);
GGT (gamma-glutamyl transferase);
$HbA_{1c}$ (glycosylated hemoglobin);
HBV (Hepatitis B Virus);
hCG (Human Chorionic Gonadotropin);
HCV (Hepatitis C Virus);
HDL (High Density Lipoprotein);
HIV (Human Immuno-deficiency Virus);
LDL (Low Density Lipoprotein);
NGAL (Neutrophil Gelatinase-Associated Lipocalin);
iPTH (Parathyroid Hormone, intact);
PT-INR (Prothrombin Time-International Normalized Ratio).

eGFR

GFR will be estimated using the Chronic Kidney Disease Epidemiology Collaboration (CKD-EPI) equation that incorporates both serum creatinine and Cystatin C. (Inker et al. Estimating glomerular filtration rate from serum creatinine and cystatin C. *N Engl J Med.* 2012; 367:20-9)

Routine Urinalysis

Urine will be collected and analyzed via standard panel. Urine will be collected over two different time periods: 24 hour collection and "spot" urine. Spot urine collections will be used for dipstick urinalysis (test stick) assessments. The schedules for collecting each type of urine sample are shown in To provide a comprehensive picture of protein and albumin excretion, both total protein and albumin will be assessed in all samples.

Hematology

Hemorrhage following NKA injection is a known and foreseeable risk to subjects participating in this study. Therefore, hemoglobin and hematocrit will be measured by the sites local laboratory a) before, b) 4 hours after, each NKA injection and compared to baseline levels. Other bleeding parameters (eg, APTT, PTT-INR, platelets) also will be measured.

Virus Serology

The biopsy cores obtained from each subject will be used for the expansion and selection of SRC. Each subject will undergo testing for viral blood-borne pathogens, including HIV, HBV, and HCV.

Drug Screen

Consistent with Exclusion Criterion outlined above, subjects are not eligible to participate in the study if they have an " . . . active history of . . . drug abuse that, in the judgment of the Investigator, would impair the subject's ability to comply with the protocol." Therefore, subjects will undergo testing for drugs of abuse.

Pregnancy Screen

A qualitative urine pregnancy test will be performed at the site using a test-strip. If the test is positive, then a confirmatory test will be performed by the clinical laboratory. If site practices do not accept the results of a test-strip, then a urine sample should be sent to the central laboratory for analysis. Post-menopausal women with a confirmatory FSH test do not have to undergo pregnancy testing throughout the study.

Renal Imaging

Ultrasound

Renal ultrasound will be performed at the Screening Visit to verify subject eligibility (ie, no evidence of renal tumors, polycystic kidney disease, renal cysts or other anatomic abnormalities that would interfere with the NKA injection procedure) along with obtaining a baseline echogenicity reading. Ultrasound will also be performed following the in-patient renal biopsy on Day 0 and Day 1, and following the in-patient NKA injection(s) on Day 0 and Day 1 with the aim of monitoring possible, subclinical AEs. Findings from the ultrasound (eg, resistance index, length, etc.) will be recorded on the CRF. An ultrasound may be conducted at other times, in the judgment of the Investigator, if needed for additional safety evaluation(s).

Computerized Tomography

Computerized tomography (CT) may be used in conjunction with ultrasound during the NKA injection procedure, according to the usual standards of care at the investigative site.

Magnetic Resonance Imaging

An MRI study without contrast will be performed from the Screening Visit through Day −1 before renal biopsy to determine kidney size and volume. During the site initiation visit, the MRI process will be defined for each site, depending on the MRI equipment available. Generally, a 1.5-T unit should be used. MRI imaging studies will help determine kidney volume (for dosing calculations). MRI will be performed using standard sequences without injection of contrast agents. Renal volume measurements may be calculated, for example, using a fast 3D gradient-echo sequence, VIBE, with an acquisition time of 22 seconds and spatial resolution of 2×1.4×1.2 mm. Imaging parameters will be recorded in the source documents and CRF. A total of four MRIs will be performed on patients.

Renal Scintigraphy

Renal scintigraphy will be used to assess left and right kidney function using the radioactive tracer $^{99m}$Tc-dimercaptosuccinic acid (DMSA) or Te99 m MAG3 (Mercaptoacetyl triglycine). This method is considered as the most reliable for measuring renal cortical function and is the preferred agent for this clinical trial. All patients in this study will receive four renal scintigraphy studies. Renal scintigraphy will be performed before the first NKA injection, before the last NKA injection, at the 6-Month Visit after the last NKA injection, and at the EOS Visit for all patients.

Surgical Procedures
Biopsy

Renal biopsy will be performed under sterile conditions using an ultrasound- or CT-guided approach consistent with site practices. Two biopsy cores will be needed to provide sufficient material for the selection of SRC and manufacture of NKA. Likewise, a 16-gauge needle should be used to insure adequate cortical material is obtained. If required, a 15-gauge needle may be used following consultation with the Medical Monitor. Bedside examination of the biopsy cores may be performed, if available, to ensure sufficient cortical material has been obtained.

Since the biopsy tissue will be used to manufacture NKA, the site must ensure that the tissue cores are harvested using sterile conditions so that the risk of contamination during subsequent cell expansion and selection is minimized.

Guidance on wound care and pain management following the biopsy procedure will be provided in the Study Reference Manual. Briefly, the subject will remain supine for 4 hours with monitoring of hemoglobin, blood pressure, gross hematuria, abdominal/flank pain, and flank ecchymosis. As long as any biopsy-related AEs have resolved, stabilized, or returned to baseline, the subject can be discharged from the hospital on the day after the biopsy consistent with site standard practice. Importantly, any pain medication administered after the renal biopsy should be selected carefully, avoiding medications with nephrotoxic potential.

If a subject experiences significant adverse events following the biopsy that, in the opinion of the Investigator, would put the subject at increased risk for significant adverse effects following NKA injection, then he/she will not be treated with NKA but will be followed until resolution of the event(s) and then discontinuation from the study.

NKA Injection

Before performing the NKA injection, the operating physician will evaluate the subject as follows:

Perform a physical examination to determine the feasibility of the procedure.

Evaluate bleeding parameters, including coagulation panel, PTT-INR, platelets, hemoglobin, hematocrit, and other pertinent laboratory studies.

Note: Hemorrhage following NKA injection is a known and foreseeable risk to subjects participating in this study. Therefore, hemoglobin and hematocrit will be measured a) before, b) 4 hours after, and c) 24 hours after each NKA injection and compared to baseline levels.

Review imaging studies, including ultrasound, MRI, and/or CT, to determine route of access, depth of kidney, and appearance of cortical-medullary junction.

Map potential NKA cell deposition sites.

Determine classification and associated perioperative/post-operative risk according to the American Society of Anesthesiologists (ASA) with respect to airway assessment, medical history, allergies, and medications.

Interview the subject and the subject's family/supporters to discuss the procedure, its risks and possible complications. Answer questions, and obtain written informed consent.

Prophylactic antibiotics will be given intravenously according to site standard practice. An initial CT scan may be ordered, if necessary, to evaluate adjacent viscera, renal location, and the presence of renal cysts. In conjunction with ultrasound, a CT scan also may help locate the cortical-medullary junction.

NKA is targeted for injection into the kidney cortex via a needle/cannula and syringe compatible with cell delivery. The intent is to introduce NKA via penetration of the kidney capsule and deposit NKA into multiple sites of the kidney cortex. Initially, the kidney capsule will be pierced using a 15- to 20-gauge trocar/access cannula inserted approximately 1 cm into the kidney cortex.

In the Phase 1 clinical study, NKA was administered via an 18-gauge needle. The proposed Phase 2 study will utilize an 18-gauge or smaller needle for NKA delivery. The needle will be threaded inside the access cannula and advanced into the kidney, from which the NKA will be administered. Injection of the NKA will be at a rate of 1 to 2 ml/min. After each 1 to 2 minute injection, the inner needle will be retracted along the needle course within the cortex to the second site of injection, and so forth, until the needle tip reaches the end of the access cannula or until the entire NKA product has been injected. Using a percutaneous delivery approach, placement of the access cannula/trocar and delivery needle will be performed using direct, real-time imaging. Options include ultrasound alone or ultrasound with complementary CT.

During the procedure, moderate conscious sedation will be employed; vital signs will be measured continuously. NKA injection will cease if there is imaging evidence of cell extravasation into central or peripheral renal blood vessels, the medullary portion of the kidney, or through the renal cortex and into the retroperitoneal soft tissues, or evidence of active bleeding.

Following completion of the NKA injection, the inner needle will be withdrawn and the outer cannula will remain in place for track embolization. During removal of the outer cannula (trocar), the site of the renal cortex puncture and needle track through the retroperitoneum will be embolized with absorbable gelatin particle/pledgets (eg, Gelfoam® [Pfizer]) or fibrin sealant (eg, TISSEEL [Baxter]) or other suitable agent to prevent excessive renal bleeding.

Upon completion of the procedure, non-contrast CT scan or ultrasound with color Doppler evaluation will be performed to image puncture site cell injection and any hematoma or bleeding events. The subject will be monitored for 2 to 3 hours post-procedure in a recovery-room environment with nursing assessment and measurement of vital signs. Subjects who do not experience complications may be discharged the same day as NKA injection, consistent with site standard practice.

What is claimed is:

1. A method for reducing rate of decline in eGFR (estimated glomerular filtration rate) in the treatment of chronic kidney disease (CKD) in a human patient comprising an eGFR of 15 to 60 mL/min, the method comprising:
   percutaneously injecting into the renal cortex of at least one kidney of the patient having said CKD a composition, the composition comprising: (i) a selected renal cell (SRC) population and (ii) a pharmaceutically acceptable carrier or excipient,
      wherein the composition is injected at a dose comprising approximately $3.0 \times 10^6$ cells of the SRC population per gram estimated kidney weight (/gk$W^{est}$),
      wherein the SRC population:
         is derived from a kidney biopsy sample of the patient;
         exhibits a buoyant density greater than approximately 1.0419 g/mL; and
         is enriched for renal epithelial cells;
      thereby reducing rate of decline in eGFR of the human patient.

2. The method of claim 1, wherein the SRC population is derived from the kidney biopsy sample by: (i) expanding kidney cells isolated from the kidney biopsy sample; (ii) subjecting the expanded kidney cells to density gradient centrifugation; and (iii) selecting, from the density gradient centrifugation, cells exhibiting the buoyant density greater than approximately 1.0419 g/mL.

3. The method of claim 1, wherein the SRC population is derived from the kidney biopsy sample by: (i) expanding kidney cells isolated from the kidney biopsy sample; (ii) culturing the expanded cells under hypoxic conditions; (iii) subjecting the cells cultured under the hypoxic conditions to density gradient centrifugation; and (iv) selecting, from the density gradient centrifugation, cells exhibiting the buoyant density greater than approximately 1.0419 g/mL.

4. The method of claim 1, wherein the pharmaceutically acceptable carrier or excipient comprises saline, buffered saline, dextrose, or water.

5. The method of claim 2, wherein the pharmaceutically acceptable carrier or excipient comprises saline, buffered saline, dextrose, or water.

6. The method of claim 3, wherein the pharmaceutically acceptable carrier or excipient comprises saline, buffered saline, dextrose, or water.

7. The method of claim 1, wherein the renal epithelial cells comprise a tubular epithelial phenotype.

* * * * *